(12) United States Patent
Yun et al.

(10) Patent No.: US 11,331,304 B2
(45) Date of Patent: May 17, 2022

(54) YAP1 INHIBITORS AND METHODS

(71) Applicant: The Jackson Laboratory, Bar Harbor, ME (US)

(72) Inventors: Kyuson Yun, Houston, TX (US); Hai-Xiao Zhai, Bedford, MA (US)

(73) Assignee: The Jackson Laboratory, Bar Harbor, ME (US)

( * ) Notice: Subject to any disclaimer, the term of this patent is extended or adjusted under 35 U.S.C. 154(b) by 0 days.

(21) Appl. No.: 16/300,140

(22) PCT Filed: May 11, 2017

(86) PCT No.: PCT/US2017/032147
§ 371 (c)(1),
(2) Date: Nov. 9, 2018

(87) PCT Pub. No.: WO2017/197104
PCT Pub. Date: Nov. 16, 2017

(65) Prior Publication Data
US 2019/0298693 A1    Oct. 3, 2019

Related U.S. Application Data

(60) Provisional application No. 62/334,868, filed on May 11, 2016.

(51) Int. Cl.
| | | |
|---|---|---|
| A61K 31/409 | (2006.01) | |
| A61K 45/06 | (2006.01) | |
| A61P 35/00 | (2006.01) | |
| C07D 403/14 | (2006.01) | |
| C07D 487/22 | (2006.01) | |
| A61K 9/00 | (2006.01) | |

(52) U.S. Cl.
CPC .......... *A61K 31/409* (2013.01); *A61K 9/0019* (2013.01); *A61P 35/00* (2018.01); *C07D 403/14* (2013.01); *C07D 487/22* (2013.01)

(58) Field of Classification Search
CPC ...... A61K 9/0019; A61K 9/00; A61K 31/409; A61K 45/06; A61K 2300/00; A61P 35/00; C07D 487/22; C07D 403/14
See application file for complete search history.

(56) References Cited

FOREIGN PATENT DOCUMENTS

| EP | 1755676 B1 | 11/2012 |
|---|---|---|
| JP | 2008031103 A | 2/2008 |
| WO | 2006/005137 A | 1/2006 |
| WO | 2011/017809 A1 | 2/2011 |
| WO | 2015/130944 A1 | 9/2015 |

OTHER PUBLICATIONS

Chang et al., 2012, caplus an 2012:919168.*
RN 126261-98-1, registry database compound, entry date Apr. 6, 1990, 1990.*
RN149753-99-1, registry database compound, entry date Sep. 3, 1993, 1993.*
Cancer-Prevention, 2021, https://www.cancerresearchuk.org/about-cancer/causes-of-cancer/can-cancer-be-prevented-0.*
Brunner et al., "Benzoporphyrins and Acetylene-Substituted Porphyrins as Improved Photosensitizers in the Photodynamic Tumor Therapy with Porphyrin Platinum Conjugates." Monatshefte fuer Chemie, 2002, 133(5), 679-705.
Burns et al., "Syntheses of chlorins from unsymmetrically substituted iron porphyrins." Journal of the Chemical Society, Perkin Transaction 1, 1988, 3119-3131.
Chow et al., "Epigenetic States of Cells of Origin and Tumor Evolution Drive Tumor-Initiating Cell Phenotype and Tumor Heterogeneity." Cancer Research (2014), 74(17): 4864-4874.
Chrominski et al., "Protoporphyrin IX/Cobyrinate Derived Hybrids— Novel Activators of Soluble Guanylyl Cyclase." European Journal of Organic Chemistry, 2013, 2013(8), 1530-1537.
Corbett et al., "Response of transplantable tumors of mice to anthracenedione derivatives alone and in combination with clinically useful agents." Cancer Treatment Reports (1982), 66(5): 1187-1200.
Cui, Qiao-Li et al., Synthesis and catalytic application of Co(II)-3, 8-diethyl deuteroporphyrin dimethyl ester to the oxidation of cyclohexane. Chemical Journal of Chinese Universities 2011, 32(10), 2311-2315, English Abstract attached.
Fernandez et al., "YAP1 is amplified and up-regulated in hedgehog-associated medulloblastomas and mediates Sonic hedgehog-driven neural precursor proliferation." Genes and Development, 2009, 23: 2729-2741.
Hu et al., "A facile synthesis of deuteroporphyrins derivatives under ultrasound irradiation." Ultrasonics Sonochemistry, 2010 17(2), 288-291.
Iakovides et al., "Regioselective photoreduction of zinc(II) porphyrins to give chlorins." Photochemistry and Photobiology, 1991, 54(3), 335-343.
International Search Report of The International Searching Authority dated Aug. 4, 2017 from corresponding International Patent Application No. PCT/US2017/032147 filed on May 11, 2017.
Kiesel et al., "Iron-Sulfur Cluster-dependent Catalysis of Chlorophyllide a Oxidoreductase from Roseobacter denitrificans." Journal of Biological Chemistry, 2015, 290(2), 1141-1154.
Kitagishi et al., "Self-Assembly of One-and Two-Dimensional Hemoprotein Systems by Polymerization through Heme-Heme Pocket Interactions." Angewandte International Edition, Chemie, (2009) 48(7): 1271-1274.
Kitagishi et al., "Supramolecular Hemoprotein Linear Assembly by Successive interprotein Heme-Heme Pocket Interactions." Journal of the American Chemical Society, 2007, 129(34), 10326-10327.

(Continued)

*Primary Examiner* — Sun Jae Yoo
(74) *Attorney, Agent, or Firm* — Pierce Atwood LLP

(57) ABSTRACT

YAP1 inhibitors and methods of treating a subject with a cancer that include administering a YAP1 inhibitor are disclosed. Also disclosed are methods for determining responsiveness to a YAP1 inhibitor in a subject, methods for diagnosing a tumor in a subject including determining the level of YAP1 expression, compositions that include YAP1 inhibitors, and methods of using those compositions.

22 Claims, 23 Drawing Sheets

(56) References Cited

OTHER PUBLICATIONS

Liu et al., "Lipopolysaccharide Neutralizing Peptide-Porphyrin Conjugates for Effective Photoinactivation and intracellular Imaging of Gram-Negative Bacteria Strains." Bioconjugate Chemistry, 2012, 23(8), 1639-1647.

Liu-Chittenden et al., "Genetic and Pharmacological disruption of the TEAD-YAP complex suppresses the oncogenic activity of YAP." Genes and Development, 2012, 26: 1300-1305.

Northcott et al., "Subgroup-specific structural variation across 1,000 medulloblastoma genomes." Nature, 2012, 488: 49-56.

Pangka et al., "Diels-Ader Reactions of Protoporphyrin IX Dimethyl Ester with Electron-Deficient Alkynes." Journal of Organic Chemistry, 1986, 51, 1094-1100.

Sakata et al., "Synthesis of Photosynthetic model compound with a long alkyl chain and its incorporation into bovine serum albumin." Tetrahedron, 1989, 45(15), 4717-4727.

Seton-Rogers, "All eyes on YAP1." Nature Reviews Cancer, 2014, 14:514-515.

Simpson et al., "Ascorbic acid photoreductions of zinc(II) chlorophyll derivatives: access to metal-free isobacteriochlorins." Journal of the American Chemical Society, 1988, 110(9), 2854-2861.

Smith et al., "Isobacteriochlorophyll b analogs from photoreduction of metallochlorins." Journal of the American Chemical Society. 1986, 108(21), 6834-6835.

Smith et al., "Site-specific reduction of unsymmetrically substituted porphyrins to give isomerically pur chlorins." Journal of the Chemical Society, Chemical Communications, 1987, (8), 613-614.

Steinhardt et al., "Expression of Yes-Associated Protein, YAP, in Common Solid Tumors." Human Pathology, 2008, 39(11): 1582-1589.

Wan et al., "Fabrication of a Thermoresponsive Biohybrid Double Hydrophilic Block Copolymer by a Cofactor Reconstitution Approach," Macromolecular Rapid Commumications, 2010, 31(23), 2070-2076.

Written Opinion of The International Searching Authority dated Aug. 4, 2017 from corresponding International Patent. Application No. PCT/US2017/032147 filed on May 11, 2017.

* cited by examiner

PN30- tumor cells- YAP1

T17

T18

T19

T20

T21

T22

T23

T24

T25

T26

T27

T28

T29

T30

| IC50 in nM | |
|---|---|
| VP | 494 |
| T10 | 3.2 |
| T11 | 90.3 |
| T13 | 74.3 |
| T14 | 1.2 |
| T15 | 6.8 | ns
YAP1 INHIBITORS AND METHODS

REFERENCE TO RELATED APPLICATIONS

This application is a National Stage Filing under 35 U.S.C. § 371 of PCT International Application PCT/US2017/032147, filed May 11, 2017, which was published under PCT Article 21(2) in English, which claims the benefit under 35 U.S.C. § 119(e) of U.S. Provisional Application Ser. No. 62/334,868, filed May 11, 2016, the content of each of which is incorporated by reference herein in its entirety.

FIELD OF THE INVENTION

This disclosure relates to novel YAP1 inhibitors and use of same in treating a subject having a cancer. This disclosure further relates to cancer therapy with verteporfin and verteporfin derivative compounds.

BACKGROUND

Many types of cancer including, for example, certain types of medulloblastoma, a common pediatric brain tumor, have poor prognoses. Additional means to identify the effectors of such cancers and methods of treating them are needed.

SUMMARY OF THE INVENTION

In one aspect, this disclosure describes verteporfin derivative compounds. In some embodiments, the verteporfin derivative compounds inhibit a Yes-associated protein 1 (referred to herein as YAP1, Yap 1, or YAP).

In another aspect, this disclosure describes pharmaceutical compositions that include a verteporfin derivative compound and a pharmaceutically acceptable excipient. In a further aspect, this disclosure describes pharmaceutical compositions that include verteporfin and a pharmaceutically acceptable excipient.

In an additional aspect, this disclosure describes methods of treating a cancer in a subject using pharmaceutical compositions that include a verteporfin, or a verteporfin derivative compound, or both. The cancer includes a cell expressing YAP1. In some embodiments, the cancer includes a medulloblastoma.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1(A-E) shows YAP1 expression and deletion.

FIG. 2(A-B) shows YAP1 is necessary for tumor maintenance but not initiation.

FIG. 3(A-E) shows YAP1 is aberrantly activated in SHH medulloblastomas.

FIG. 4(A-F) shows YAP1 is required for medulloblastoma stem cell self-renewal but not neural stem cell (NSC) self-renewal.

FIG. 5(A-C) shows that verteporfin (VP), a YAP1 inhibitor and an FDA approved drug for treating macular degeneration, inhibits self-renewal in SHH-induced medulloblastoma cells and growth of medulloblastoma tissue.

FIG. 6(A-D) shows elevated YAP1 protein levels, but not RNA levels, in SHH inhibitor-resistant SHH tumors.

FIG. 9(A-B) shows testing of exemplary verteporfin derivative compounds.

DETAILED DESCRIPTION

Definitions

Figure 1A:
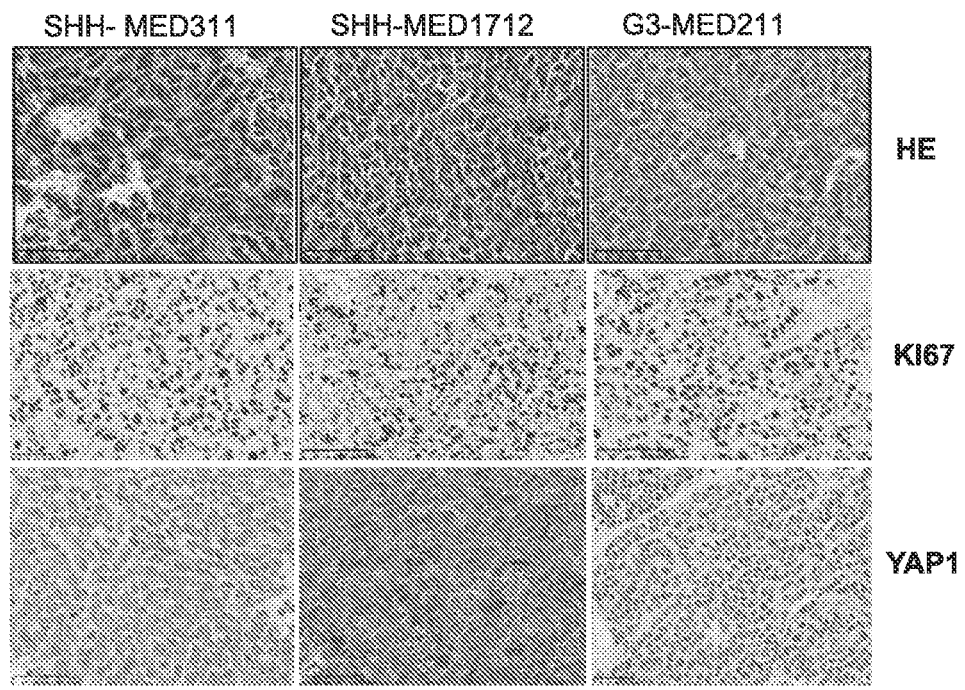
FIG. 1A) YAP1 expression in two independent patient-derived SHH medulloblastoma xenografts and one G3 tumor shows YAP1 expression in the SHH subgroup tumors but not G3 subgroup tumor.

As used herein, "YAP1" (yes-associated protein 1), also known as YAP or YAP65, is a protein that acts as a transcriptional regulator by activating the transcription of genes involved in cell proliferation and suppressing apoptotic genes. YAP1 is inhibited in the Hippo signaling pathway, a pathway that may be involved in the cellular control of organ size and tumor suppression. YAP1 was first identified by virtue of its ability to associate with the SH3 domain of Yes and Src protein tyrosine kinases, and it is an oncogene.

As used herein, "verteporfin" refers to a compound having IUPAC name of (3-[(23 S,24R)-14-ethenyl-5-(3-methoxy-3-oxopropyl)-22,23-bis(methoxycarbonyl)-4,10,15,24-tetramethyl-25,26,27,28-tetraazahexacyclo [16.6.1.13,6.18,11.113,16.019,24]octacosa-1,3,5,7,9,11(27), 12,14,16,18(25), 19,21-dodecaen-9-yl]propanoic acid). As a benzoporphyrin derivative, verteporfin has a trade name of Visudyne, and it is a medication used as a photosensitizer for photodynamic therapy to eliminate the abnormal blood vessels in the eye associated with conditions such as the wet form of macular degeneration.

As used herein, a "verteporfin derivative compound" refers to one or more of the compounds shown in FIG. 8. Anywhere in the present application where a name of a compound may not correctly describe the structure of the compound, the structure supersedes the name and governs.

As used herein, "cancer" includes all types of cancers and precancerous conditions including those which can be evidenced by tumor formation. The term encompasses cancer localized in tumors, as well as cancer not localized in tumors, such as, for instance, cancer cells which expand from a tumor locally by invasion. The cancer can involve any tissue or organ, such as bone, brain, breast, cervix, larynx, lung, pancreas, prostate, skin, spine, stomach, uterus or blood. The cancer can be bone cancer, brain cancer, breast cancer, cervical cancer, cancer of the larynx, lung cancer, pancreatic cancer, prostate cancer, skin cancer, cancer of the spine, stomach cancer, uterine cancer, or blood cancer. The cancer can be a metastatic cancer. A tumor may include a solid tumor. A tumor may be a fast growing tumor.

The term "biological sample" refers to material from any living organism. In some embodiments, a biological sample preferably includes a cell.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least 10%, at least 15%, at least 20%, or at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, compared to the expected reduction in the parameter in an individual not treated with the agent.

As used herein "treating" or "treatment" can include at least one of therapeutic treatment and prophylactic treatment. "Treating a disorder," as used herein, is not intended to be an absolute term. Treatment may lead to an improved prognosis or a reduction in the frequency or severity of symptoms. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. Likewise, the term "preventing," as used herein, is not intended as an absolute term. Instead, prevention refers to delay of onset, reduced frequency of symptoms, or reduced severity of symptoms associated with a disorder. Prevention therefore refers to a broad range of prophylactic measures that will be understood by those in the art. In some circumstances, the frequency and severity of symptoms is reduced to non-pathological levels. In some circumstances, the symptoms of an individual receiving the compositions of the disclosure are up to 90%, up to 80%, up to 70%, up to 60%, up to 50%, up to 40%, up to 30%, up to 20%, up to 10%, up to 5% or up to 1% as frequent or severe as symptoms experienced by an untreated individual with the disorder.

As used herein, the term "subject" includes, but is not limited to, humans and non-human vertebrates. In preferred embodiments, a subject is a mammal, particularly a human. A subject may be an individual. A subject may be an "individual," "patient," or "host." Non-human vertebrates include livestock animals, companion animals, and laboratory animals. Non-human subjects also include non-human primates as well as rodents such as, but not limited to, a rat or a mouse. Non-human subjects also include, without limitation, chickens, horses, cows, pigs, goats, dogs, cats, guinea pigs, hamsters, mink, and rabbits.

As used herein, "in vitro" is in cell culture and "in vivo" is within the body of a subject. As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

All headings are for the convenience of the reader and should not be used to limit the meaning of the text that follows the heading, unless so specified.

The present disclosure provides methods of treating and diagnosing cancer including, for example, certain types of medulloblastoma. Yes-associated protein 1 (YAP1, Yap1, or YAP; used herein interchangeable) is over-expressed in many human cancers, and YAP1 may provide a vehicle for treating or diagnosing certain types of cancers. The present disclosure further provides compounds, compositions, and methods relating to a YAP1 inhibitor and the use of these compounds, compositions, and methods as a therapeutic agent to, for example, prevent or treat the growth of cancers. The present disclosure also includes methods of making and using the YAP1 inhibitors, conjugates and compositions described herein.

YAP1 is a transcriptional effector of the Hippo signaling pathway, a developmental signaling pathway that controls organ size. A critical step in the Hippo signaling pathway is the regulation of nuclear localization of YAP1 and its paralogue, WWtr1/TAZ. Activation of the Hippo signaling pathway leads to phosphorylation of YAP1 by kinases LATS1/2, which results in either sequestration of YAP1 (S127) in the cytoplasm or degradation of YAP1(S381). Inhibition of the Hippo signaling pathway allows un-phosphorylated YAP1 to enter the nucleus and provide a transcriptional activation domain to its various binding partners, including (TEA domain family member) TEAD proteins. While TEAD proteins (for example, TEAD1-TEAD4) can bind to DNA, they do not have a transcriptional activation domain, requiring YAP1 or WWtr1/TAZ, to regulate downstream target genes, many of which promote proliferation and survival.

Consistent with its role in promoting proliferation and survival, YAP is over-expressed in many human cancers. While mutations are rare, translocations involving YAP and amplifications including YAP have been observed in multiple cancer types. (For example, Steinhardt et al., *Human Pathology*, 2008, 39(11): 1582-1589; Seton-Rogers, *Nature Reviews Cancer*, 2014, 14:514-515.) Recent large-scale genomics analysis of medulloblastomas revealed that YAP1 is amplified in the Sonic Hedgehog (SHH) subgroup. SHH subgroup tumors express high levels of SHH pathway genes. The enhanced expression is often due to mutations in the pathway components, such as Ptch (a negative upstream receptor for the pathway) and SMO (a positive upstream receptor of the pathway). YAP1 is highly expressed in a SHH-induced medulloblastoma mouse model, and high-levels of YAP1 expression promote therapy-resistance and genomic instability in murine medulloblastoma cells. YAP1 overexpression can also be responsible for acquired therapy resistance to targeted therapies that inhibit multiple components in the MAPK pathway.

The present disclosure provides compositions including one or more YAP1 inhibitors; a method of using a YAP 1 inhibitor; a method of treating a subject with cancer wherein the method includes administering a YAP1 inhibitor; a method for determining responsiveness to a YAP1 inhibitor in a subject; a method for diagnosing cancer in a subject; and a composition and a method of using the composition for treating a subject with cancer. In some embodiments, the cancer includes at least one of a YAP 1-expressing cell, a brain tumor, a SHH-expressing cell, a pediatric tumor, and a medulloblastoma.

The present disclosure includes a method of using a YAP1 inhibitor and compositions including one or more of the YAP1 inhibitors described herein. Such a composition may be a pharmaceutical composition that includes a pharmaceutically acceptable carrier. The pharmaceutical carrier may be selected with regard to the intended route of administration and standard pharmaceutical practice. As used herein, a pharmaceutically acceptable carrier includes one or more compatible solid or liquid fillers, excipients, diluents, or encapsulating substances which are suitable for administration to a human or other vertebrate animal. Suitable carriers are well known in the art. Such a carrier may be pyrogen free. A carrier may be non-naturally occurring.

In some embodiments, the pharmaceutical composition may be formulated to increase the solubility of a YAP 1 inhibitor including, for example, verteporfin or a verteporfin derivative compound. Verteporfin is relatively insoluble in water (exhibiting low water solubility), and, the verteporfin derivative compounds may also exhibit low water solubility. In some embodiments, the therapeutic use of verteporfin derivative compounds can be enhanced by increasing the solubility or bioavailability or both. An increase in bioavailability can mean, for example, that a larger amount of the administered compound reaches a relevant target site or achieves a therapeutically effective amount or both. In some embodiments, the pharmaceutical composition may be formulated to increase bioavailability of a verteporfin derivative compound. Any suitable formulation strategy to increase bioavailability of a verteporfin derivative compound may be used including, for example, complexation with cyclodextrins; formulation of polymeric conjugates; use of nanoparticles, solid lipid nanoparticles, permeation enhancers, polymers, surfactants, etc. In some embodiments, a pharmaceutically acceptable carrier may be selected to increase bioavailability of a verteporfin derivative compound.

A pharmaceutical composition may be adapted to the chosen route of administration. One of skill will understand that the composition will vary depending on mode of administration and dosage unit. For example, for parenteral administration, isotonic saline can be used. For topical administration a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions. The compounds can be administered in a variety of ways including, but not limited to, intravenous, topical, oral, subcutaneous, intraperitoneal, and intramuscular delivery. In some aspects, the compounds may be formulated for controlled or sustained release. In some aspects, a formulation for controlled or sustained release is suitable for subcutaneous implantation. In some aspects, a formulation for controlled or sustained release includes a patch. A compound may be formulated for enteral administration. A compound may be, for example, formulated as a capsule or tablet.

In some embodiments, a pharmaceutical composition may be adapted to increase the bioavailability of verteporfin or a verteporfin derivative compound, or both. For example, a composition may be selected by an artisan to enhance the absorption of a verteporfin derivative compound including, for example, via the intestinal wall. In some embodiments, it can also desirable to provide a formulation suitable for oral administration of verteporfin or a verteporfin derivative compound, or both that increases the solubility of the compound in an aqueous environment.

Administration may be as a single dose or in multiple doses. Preferably the dose is an effective amount as determined by the standard methods including, but not limited to, those described herein. Those skilled in the art of clinical trials will be able to optimize dosages of particular compounds through standard studies. Additionally, proper dosages of the compositions can be determined without undue experimentation using standard dose-response protocols. Administration includes, but is not limited to, any of the dosages and dosing schedules, dosing intervals, and dosing patterns described in the examples included herewith.

In some embodiments, the YAP1 inhibitor includes a verteporfin derivative. In some embodiments, the YAP1 inhibitor includes at least one of the compounds of FIG. 8. In some embodiments, the YAP1 inhibitor may be present in a composition including, for example, a pharmaceutical preparation.

The compounds of FIG. 8 include T1-T30:

T1 ((2S)-2-[3-[(23 S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13,6.18,11.113, 16.019,24]octacosa-1,3,5,7,9,11(27),12,14,16,18(25), 19,21-dodecaen-9-yl]propanoylamino]butanedioic acid)

T2 ((2S)-2-[3-[(23 S,24R)-14-ethenyl-5-(2-carboxyethyl)-22,23-bis(methoxycarbonyl)-4,10,15,24-tetramethyl-25,26,27,28-tetraazahexacyclo[16.6.1.13,6.18,11.113, 16.019,24]octacosa-1,3,5,7,9,11(27),12,14,16,18(25), 19,21-dodecaen-9-yl]propanoylamino]butanedioic acid)

T3 ((2S)-2-[3-[(23 S,24R)-14-ethenyl-5-[3-[[(1 S)-1,2-dicarboxyethyl]amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5, 7,9,11(27),12,14,16,18(25), 19,21-dodecaen-9-yl] propanoylamino]butanedioic acid)

T4((2S)-2-[3-[3-[(23 S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13,6.18,11.113, 16.019,24]octacosa-1,3,5,7,9,11(27),12,14,16,18(25), 19,21-dodecaen-9-yl]propanoylamino]propanoylamino]butanedioic acid).

T5 ((2S)-2-amino-6-[3-[(23 S,24R)-14-ethenyl-5-(3-methoxy-3-oxopropyl)-22,23-bis(methoxycarbonyl)-4,10, 15,24-tetramethyl-25,26,27,28-tetraazahexacyclo [16.6.1.13,6.18,11.113,16.019,24]octacosa-1,3,5,7,9,11(27), 12,14,16,18(25), 19,21-dodecaen-9-yl]propanoylamino] hexanoic acid)

T6 ((2S)-2-amino-6-[3-[(23 S,24R)-14-ethenyl-5-(2-carboxyethyl)-22,23-bis(methoxycarbonyl)-4,10,15,24-tetramethyl-25,26,27,28-tetraazahexacyclo[16.6.1.13,6.18,11.113, 16.019,24]octacosa-1,3,5,7,9,11(27),12,14,16,18(25), 19,21-dodecaen-9-yl]propanoylamino]hexanoic acid)

T7 ((2S)-2-amino-6-[3-[(23 S,24R)-14-ethenyl-5-[3-[[(5 S)-5-amino-5-carboxy-pentyl]amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25), 19,21-dodecaen-9-yl]propanoylamino]hexanoic acid)

T8 (Methyl 3-[(23S,24R)-14-ethenyl-9-[3-[2-[2-(2-methoxyethoxy)ethoxy]ethoxy]-3-oxo-propyl]-22,23-bis (methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25), 19,21-dodecaen-5-yl] propanoate)

T9 (2-[2-(2-methoxyethoxy)ethoxy]ethyl 3-[(23 S,24R)-14-ethenyl-5-[3-[2-[2-(2-methoxyethoxy)ethoxy]ethoxy]-3-oxo-propyl]-22,23-bis(methoxycarbonyl)-4,10,15,24-tetramethyl-25,26,27,28-tetraazahexacyclo[16.6.1.13,6.18, 11.113,16.019,24]octacosa-1,3,5,7,9,11(27),12,14,16,18 (25), 19,21-dodecaen-9-yl]propanoate)

T10 (Methyl 3-[(23S,24R)-14-ethenyl-9-[3-[2-[2-[2-[2-[2-(2-methoxyethoxy)ethoxy]ethoxy]ethoxy]ethoxy] ethoxy]ethoxy]-3-oxo-propyl]-22,23-bis(methoxycarbonyl)-4,10,15,24-tetramethyl-25,26,27,28-tetraazahexacyclo

[16.6.1.13,6.18,11.113,16.019,24]octacosa-1,3,5,7,9,11(27), 12,14,16,18(25), 19,21-dodecaen-5-yl]propanoate)

T11 (Methyl 3-[(23 S,24R)-14-ethenyl-9-[3-[2-(dimethylamino)ethylamino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11 (27), 12,14,16,18(25), 19,21-dodecaen-5-yl]propanoate)

T12 (3-[(23 S,24R)-14-ethenyl-9-[3-[2-(dimethylamino) ethylamino]-3-oxo-propyl]-22,23-bis(methoxycarbonyl)-4, 10,15,24-tetramethyl-25,26,27,28-tetraazahexacyclo [16.6.1.13,6.18,11.113,16.019,24]octacosa-1,3,5,7,9,11(27), 12,14,16,18(25), 19,21-dodecaen-5-yl]propanoic acid)

T13 (N-[2-(dimethylamino)ethyl]-3-[(23 S,24R)-14-ethenyl-5-[3-[2-(dimethylamino)ethylamino]-3-oxo-propyl]-22, 23-bis(methoxycarbonyl)-4,10,15,24-tetramethyl-25,26,27, 28-tetraazahexacyclo[16.6.1.13,6.18,11.113,16.019,24] octacosa-1,3,5,7,9,11(27), 12,14,16,18(25), 19,21-dodecaen-9-yl]propanamide)

T14 (Methyl 3-[(23S,24R)-14-ethenyl-9-[3-[2-(dimethylamino)ethyl-methyl-amino]-3-oxo-propyl]-22,23-bis (methoxycarbonyl)-4,10,15,24-tetramethyl-25,26,27,28-tetraazahexacyclo[16.6.1.13,6.18,11.113,16.019,24]octacosa-1,3,5,7,9,11(27), 12,14,16,18(25), 19,21-dodecaen-5-yl] propanoate)

T15 (N-[2-(dimethylamino)ethyl]-3-[(23 S,24R)-14-ethenyl-5-[3-[2-(dimethylamino)ethyl-methyl-amino]-3-oxo-propyl]-22,23-bis(methoxycarbonyl)-4,10,15,24-tetramethyl-25,26,27,28-tetraazahexacyclo[16.6.1.13,6.18,11.113, 16.019,24]octacosa-1,3,5,7,9,11(27), 12,14,16,18(25),19, 21-dodecaen-9-yl]-N-methyl-propanamide)

T16 ((3-(7-(3-methoxy-3-oxopropyl)-2,8,12,17-tetramethyl-13,18-divinyl-7H,8H-porphyrin-3-yl)propanoyl)-L-aspartic acid)

T17 ((3-(7-(2-carboxyethyl)-2,8,12,17-tetramethyl-13, 18-divinyl-7H,8H-porphyrin-3-yl)propanoyl)-L-aspartic acid)

T18 ((3-(7-(5,6-dicarboxy-3-oxohexyl)-2,8,12,17-tetramethyl-13,18-divinyl-7H,8H-porphyrin-3-yl)propanoyl)-L-aspartic acid)

T19 ((3-(3-(7-(3-methoxy-3-oxopropyl)-2,8,12,17-tetramethyl-13,18-divinyl-7H,8H-porphyrin-3-yl)propanamido)propanoyl)-L-aspartic acid)

T20 (N6-(3-(7-(3-methoxy-3-oxopropyl)-2,8,12,17-tetramethyl-13,18-divinyl-7H,8H-porphyrin-3-yl)propanoyl)-L-lysine)

T21 (N6-(3-(7-(2-carboxyethyl)-2,8,12,17-tetramethyl-13,18-divinyl-7H,8H-porphyrin-3-yl)propanoyl)-L-lysine)

T22 ((2 S,2'S)-6,6'-((3,3'-(2,8,12,17-tetramethyl-13,18-divinyl-7H,8H-porphyrin-3,7-diyl)bis(propanoyl))bis (azanediyl))bis(2-aminohexanoic acid))

T23 (2-(2-(2-methoxyethoxy)ethoxy)ethyl 3-(7-(3-methoxy-3-oxopropyl)-2,8,12,17-tetramethyl-13,18-divinyl-7H,8H-porphyrin-3-yl)propanoate)

T24 (bis(2-(2-(2-methoxyethoxy)ethoxy)ethyl) 3,3'-(2,8, 12,17-tetramethyl-13,18-divinyl-7H,8H-porphyrin-3,7-diyl) dipropionate)

T25 (2,5,8,11,14,17,20-heptaoxadocosan-22-yl 3-(7-(3-methoxy-3-oxopropyl)-2,8,12,17-tetramethyl-13,18-divinyl-7H,8H-porphyrin-3-yl)propanoate)

T26 (methyl 3-(3-(3-((2-(dimethylamino)ethyl)amino)-3-oxopropyl)-2,8,12,17-tetramethyl-13,18-divinyl-7H,8H-porphyrin-7-yl) propanoate)

T27 (3-(3-(3-((2-(dimethylamino)ethyl)amino)-3-oxo-propyl)-2,8,12,17-tetramethyl-13,18-divinyl-7H,8H-porphyrin-7-yl)propanoic acid)

T28 (3,3'-(2,8,12,17-tetramethyl-13,18-divinyl-7H,8H-porphyrin-3,7-diyl)bis(N-(2-(dimethylamino)ethyl) propanamide))

T29 (methyl 3-(3-(3-((2-(dimethylamino)ethyl)(methyl) amino)-3-oxopropyl)-2,8,12,17-tetramethyl-13,18-divinyl-7H,8H-porphyrin-7-yl)propanoate)

T30 (N-(2-(dimethylamino)ethyl)-3-(7-(3-((2-(dimethylamino) ethyl)amino)-3-oxopropyl)-2,8,12,17-tetramethyl-13,18-divinyl-7H,8H-porphyrin-3-yl)-N-methylpropanamide)

A YAP1 inhibitor can be administered by any suitable means or any effective route including, but not limited to, for example, oral, rectal, nasal, topical (including transdermal, aerosol, buccal, and/or sublingual), vaginal, parenteral (including subcutaneous, intramuscular, and/or intravenous), intradermal, intravesical, intra-joint, intra-arteriole, intraventricular, intraspinal, intracranial, intraperitoneal, intranasal, by inhalation, or intralesional (for example, by injection into or around a tumor). In some embodiments, oral administration of a YAP1 inhibitor may be preferred. In some embodiments, injection of a YAP 1 inhibitor into the spinal canal may be preferred. In some embodiments, a YAP1 inhibitor may be applied as an oral or nasal mucosal spray.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA. Such preparation may be pyrogen-free.

For enteral administration, the inhibitor may be administered in a tablet or capsule, which may be enteric coated, or in a formulation for controlled or sustained release. Many suitable formulations are known, including polymeric or protein microparticles encapsulating drug to be released, ointments, gels, or solutions which can be used topically or locally to administer drug, and even patches, which provide controlled release over a prolonged period of time. These can also take the form of implants. Such an implant may be implanted within a tumor.

The compounds can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Therapeutically effective concentrations and amounts may be determined for each application herein empirically by testing the compounds in known in vitro and in vivo systems, such as those described herein, dosages for humans or other animals may then be extrapolated therefrom.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

Toxicity and therapeutic efficacy of the compounds and compositions can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition.

An agent as described herein may be administered at once, or may be divided into a number of smaller doses to be administered at intervals of time. For example, compounds may be administered repeatedly, e.g., at least 2, at least 3, at least 4, at least 5, at least 6, at least 7, at least 8, or more times, or may be administered by continuous infusion. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

In some aspects of the methods of the present disclosure, a method further includes the administration of one or more additional therapeutic agents. One or more additional therapeutic agents may be administered before, after, and/or coincident to the administration of a YAP1 inhibitor as described herein. A YAP1 inhibitor and additional therapeutic agents may be administered separately or as part of a mixture or cocktail. In some aspects of the present disclosure, the administration of YAP1 inhibitor may allow for the effectiveness of a lower dosage of other therapeutic modalities when compared to the administration of the other therapeutic modalities alone, providing relief from the toxicity observed with the administration of higher doses of the other modalities.

In some embodiments, including, for example, when the YAP1 inhibitor is administered to a subject at risk of having or having a medulloblastoma, the YAP1 inhibitor may be administered in combination with other treatments for medulloblastoma. For example, the YAP1 inhibitor may be administered in combination with a SMO inhibitor, a MAP Kinase inhibitor, or a SHH pathway inhibitor.

In some aspects of the methods of the present disclosure, the administration a compound as described herein and the at least one additional therapeutic agent demonstrate therapeutic synergy. In some aspects of the methods of the present disclosure, a measurement of response to treatment observed after administering both a YAP1 inhibitor as described herein and the additional therapeutic agent is improved over the same measurement of response to treatment observed after administering either the YAP1 inhibitor or the additional therapeutic agent alone.

As used herein, an additional therapeutic agent may be an agent whose use for the treatment of cancer is known to the skilled artisan. Additional therapeutic treatments include, but are not limited to, surgery and/or surgical resection, radiation therapy, hormone therapy, targeted therapy, vaccines, antibody based therapies, whole body irradiation, bone marrow transplantation, peripheral blood stem cell transplantation, the administration of chemotherapeutic agents (also referred to herein as "antineoplastic chemotherapy agent," "antineoplastic agents," or "antineoplastic chemotherapeutic agents"), cytokines, antiviral agents, immune enhancers, tyrosine kinase inhibitors, protein kinase C (PKC) modulator (such as, for example, the PKC activator ingenol 3-angelate (PEP005) or the PKC inhibitor bisindolylmaleimid (enzastaurin), signal transduction inhibitors, antibiotics, antimicrobial agents, a TLR agonist (such as, for example, bacterial lipopolysaccharides (LPS) or a CpG oligonucleotide (ODN)), an inhibitor of IDO (such as, for example, 1-MT), and adjuvants.

A targeted therapy may be, for example, a monoclonal antibody drug or a small molecule drug. In some embodiments, a targeted therapy may target a single abnormal protein in a cancer or multiple different proteins in a cancer. A targeted therapy may include, for example, a signal transduction inhibitor including, for example, a MAPK inhibitor; a SHH pathway inhibitor; a SMO inhibitor; an EGFR inhibitor, such as cetuximab or erlotinib; a HER2 inhibitor, such as trastuzumab or pertuzumab; a BCR-ABL inhibitor, such as imatinib or dasatinib; an ALK inhibitor, such as crizotinib or ceritinib; and a BRAF inhibitor, such as vemurafenib or dabrafenib. A targeted therapy may include, for example, an angiogenesis inhibitor, an apoptosis-inducing drug, and an immunotherapy.

A chemotherapeutic agent may be, for example, a cytotoxic chemotherapy agent such as, for example, epidophyllotoxin, procarbazine, mitoxantrone, platinum coordination complexes such as cisplatin and carboplatin, leucovorin, tegafur, paclitaxel, docetaxol, vincristine, vinblastine, methotrexate, cyclophosphamide, gemcitabine, estramustine, carmustine, adriamycin (doxorubicin), etoposide, arsenic trioxide, irinotecan, epothilone derivatives, navelbene, CPT-11, anastrazole, letrazole, capecitabine, reloxafine, ifosamide, and droloxafine.

A chemotherapeutic agent may be, for example, an alkylating agent such as, for example, irofulven, nitrogen mustards (such as chlorambucil, cyclophosphamide, ifosfamide, mechlorethamine, melphalan, and uracil mustard), aziridines (such as thiotepa), methanesulphonate esters (such as busulfan), nitroso ureas (such as carmustine, lomustine, and streptozocin), platinum complexes (such as cisplatin and carboplatin), and bioreductive alkylators (such as mitomycin, procarbazine, dacarbazine and altretamine), ethylenimine derivatives, alkyl sulfonates, triazenes, pipobroman, temozolomide, triethylene-melamine, and triethylenethiophosphoramine.

A chemotherapeutic agent may be an antimetabolite such as, for example, a folate antagonist (such as methotrexate and trimetrexate), a pyrimidine antagonist (such as fluorouracil, fluorodeoxyuridine, CB3717, azacitidine, cytarabine, gemcitabine, and floxuridine), a purine antagonist (such as mercaptopurine, 6-thioguanine, fludarabine, and pentostatin), a ribonucleotide reductase inhibitor (such as hydroxyurea), and an adenosine deaminase inhibitor.

A chemotherapeutic agent may be a DNA strand-breakage agent (such as, for example, bleomycin), a topoisomerase II inhibitor (such as, for example, amsacrine, dactinomycin, daunorubicin, idarubicin, mitoxantrone, doxorubicin, etoposide, and teniposide), a DNA minor groove binding agent (such as, for example, plicamydin), a tubulin interactive agent (such as, for example, vincristine, vinblastine, and paclitaxel), a hormonal agent (such as, for example, estrogens, conjugated estrogens, ethinyl estradiol, diethyl stilbesterol, chlortrianisen, idenestrol, progestins (such as hydroxyprogesterone caproate, medroxyprogesterone, and megestrol), and androgens (such as testosterone, testosterone propionate, fluoxymesterone, and methyltestosterone)), an adrenal corticosteroid (such as, for example, prednisone, dexamethasone, methylprednisolone, and prednisolone), a leutinizing hormone releasing agent or gonadotropin-releasing hormone antagonist (such as, for example, leuprolide acetate and goserelin acetate), an antihormonal agent (such as, for example, tamoxifen), an antiandrogen agent (such as flutamide), an antiadrenal agent (such as mitotane and aminoglutethimide), and a natural product or derivative thereof (such as, for example, vinca alkaloids, antibiotics, enzymes and epipodophyllotoxins), including, for example vinblastine, vincristine, vindesine, bleomycin, dactinomycin, daunorubicin, doxorubicin, epirubicin, idarubicin, ara-C, paclitaxel, mithramycin, deoxycoformycin, mitomycin-C, L-asparaginase, and teniposide.

In some aspects of the methods of the present disclosure, at least one additional therapeutic agent includes radiation therapy. In some aspects, radiation therapy includes localized radiation therapy delivered to the tumor. In some aspects, radiation therapy includes total body irradiation.

Cytokines include, but are not limited to, IL-1α, IL-1β, IL-2, IL-3, IL-4, IL-6, IL-8, IL-9, IL-10, IL-12, IL-13, IL-15, IL-18, IL-19, IL-20, IFN-α, IFN-β, IFN-γ, tumor necrosis factor (TNF), transforming growth factor-β (TGF-β), granulocyte colony stimulating factor (G-CSF), macrophage colony stimulating factor (M-CSF), granulocyte-macrophage colony stimulating factor (GM-CSF), and or Flt-3 ligand. Antibody therapeutics, include, for example, trastuzumab (Herceptin) and antibodies to cytokines, such as IL-10 and TGF-3.

In some aspects of the methods of the present disclosure, a measurement of response to treatment observed after administering both a YAP1 inhibitor as described herein and the additional therapeutic agent is improved over the same measurement of response to treatment observed after administering either the YAP1 inhibitor or the additional therapeutic agent alone. In some aspects of the methods of the present disclosure, the administration a YAP1 inhibitor as described herein and the at least one additional therapeutic agent demonstrate therapeutic synergy. As used herein, a combination may demonstrate therapeutic synergy if it is therapeutically superior to one or other of the constituents used at its optimum dose (Corbett et al., 1982, *Cancer Treatment Reports;* 66:1187). In some embodiments, a combination demonstrates therapeutic synergy if the efficacy of a combination is characterized as more than the additive actions of each constituent.

In one aspect, the present disclosure provides a method of treating a subject with cancer wherein the method includes administering a YAP1 inhibitor. In one aspect, the present disclosure provides administering a YAP1 inhibitor prophylactically, to prevent or delay the development of cancer (including a precancerous condition) in a subject. In some embodiments, the subject is a human.

Treatment that is prophylactic, for instance, can be initiated before a subject develops cancer or manifests cancer symptoms. An example of a subject that is at particular risk of developing cancer is a person having a risk factor, such as a genetic marker, that is associated with the disease. Examples of genetic markers indicating a subject has a predisposition to develop certain cancers include alterations in the BRCA1 and/or BRCA2 genes (breast, prostate, or colon cancer) and HPC1 (prostate cancer). Treatment can be performed before, during, or after the occurrence of cancer. Treatment initiated after the development of cancer may result in decreasing the severity of the symptoms of one of the conditions, or completely removing the symptoms. A YAP 1 inhibitor can be introduced into the mammal either systemically or at the site of a cancer including, for example, at the site of a tumor.

In some embodiments, the cancer includes at least one of a YAP 1-expressing cell, a brain tumor, a pediatric tumor, a medulloblastoma, and a SHH-expressing cell. In some embodiments, the cancer is preferably a YAP1-expressing cancer. A YAP1 expressing cancer may be identified by, for example, measuring the level of YAP 1 in a cell of the cancer, measuring the level of SHH in the a cell of the cancer, or measuring the level of a gene of the SHH pathway in a cell of the cancer.

In some embodiments, the medulloblastoma includes any of the four main subgroups of medulloblastoma: Wnt, SHH, Group 3, and Group 4. While medulloblastoma patients having a tumor from the Wnt subgroup generally respond to existing therapies, the prognosis of patients in the SHH subgroup is mixed; yet the underlying differences among patients with good and poor prognoses was previously unknown. As shown in the present disclosure, however, YAP1 plays a role in SHH-induced medulloblastoma. Thus, in some embodiments, it is preferred that the cancer includes at least one of a Sonic Hedgehog (SHH)-subgroup medulloblastoma and a SHH-expressing cell. In some embodiments, a SHH-expressing cancer cell may include a cell from, for example, a pancreatic tumor, a basal cell carcinoma, an adenoma, an adenocarcinoma, a breast tumor, etc. In some embodiments, the cancer comprises a cancer treated with at least one of a MAP Kinase inhibitor, a SHH inhibitor, and a SMO inhibitor. The cancer may have been previously treated with at least one of a MAP Kinase inhibitor, a SHH inhibitor, and a SMO inhibitor. In some embodiments, the cancer includes at least one of a MAP Kinase inhibitor resistant tumor, a SMO inhibitor resistant tumor, and a SHH inhibitor resistant tumor.

Figure 7:
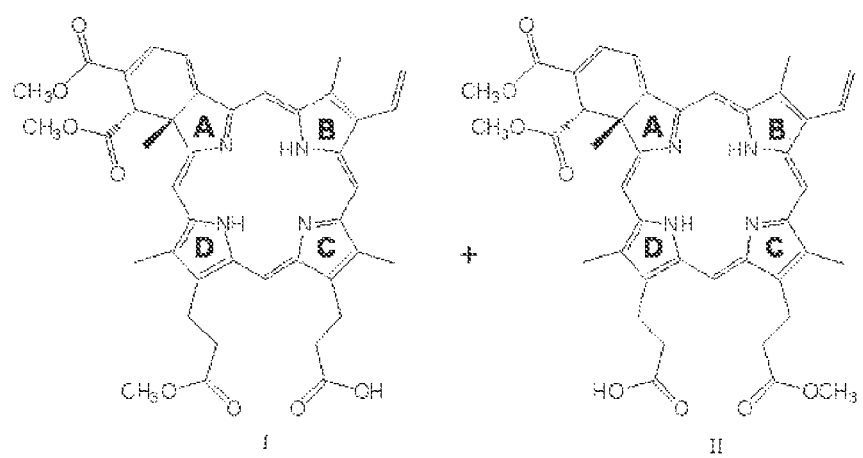
FIG. 7 shows the structure of verteporfin (3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27), 12,14,16,18(25),19,21-dodecaen-9-yl]propanoic acid) regioisomers.
Figure 8A:
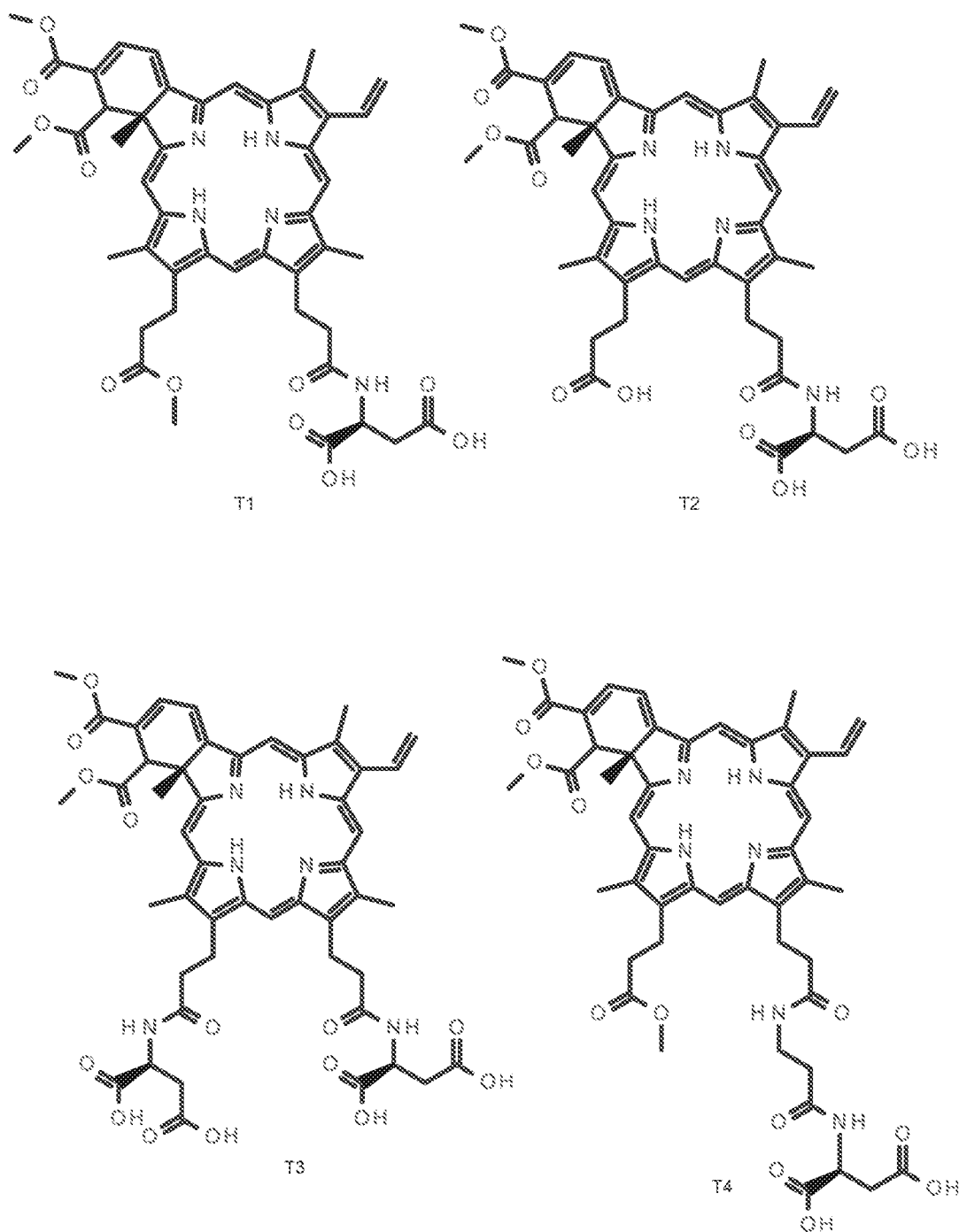
FIG. 8A shows structures of verteporfin derivative compounds T1-T4.
Figure 8B:
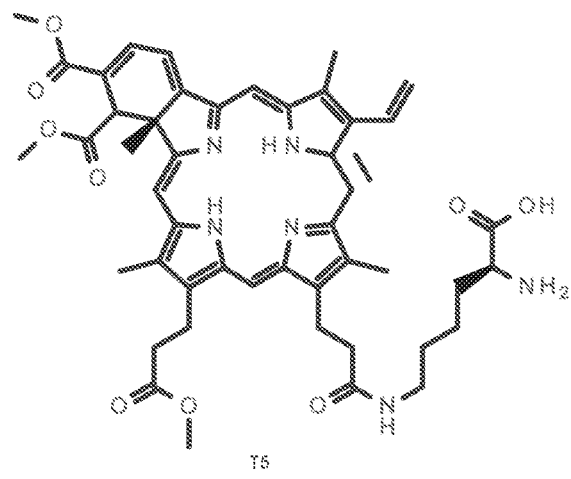
FIG. 8B shows structures of verteporfin derivative compounds T5-T8.
Figure 8B:
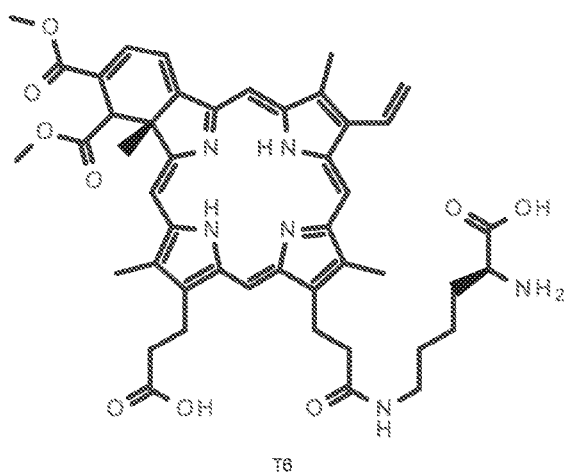
Figure 8B:
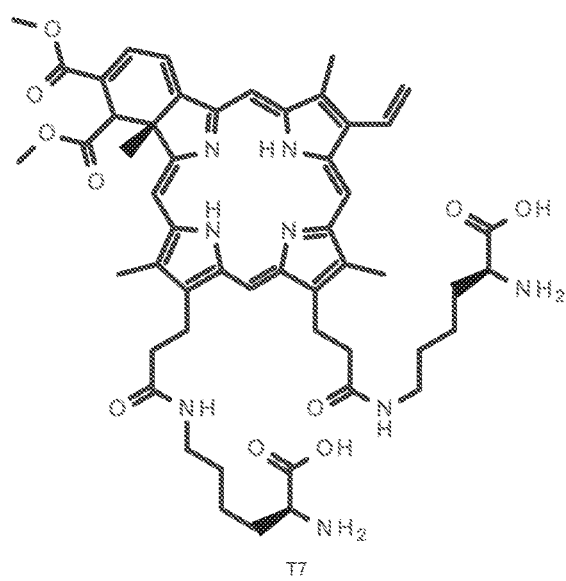
Figure 8B:
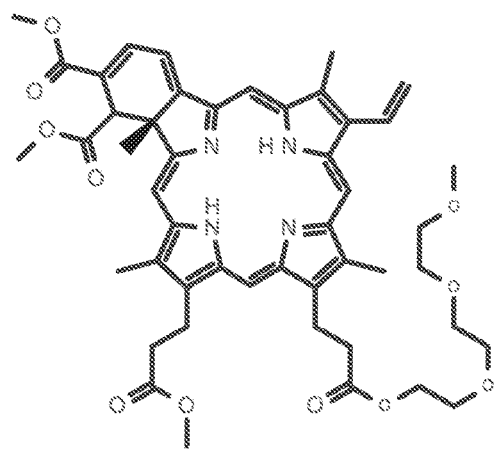
Figure 8C:
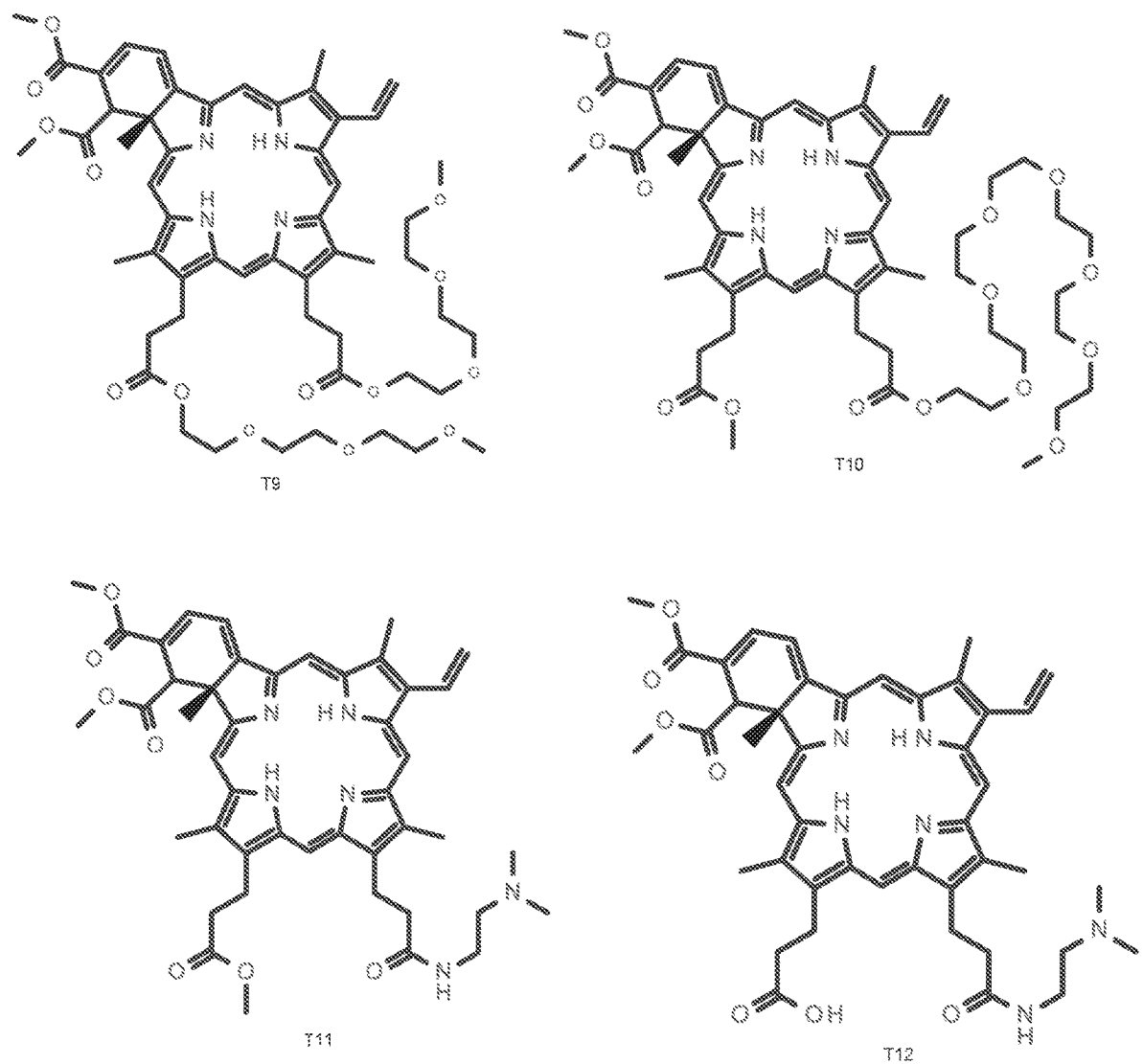
FIG. 8C shows structures of verteporfin derivative compounds T9-T12.
Figure 8D:
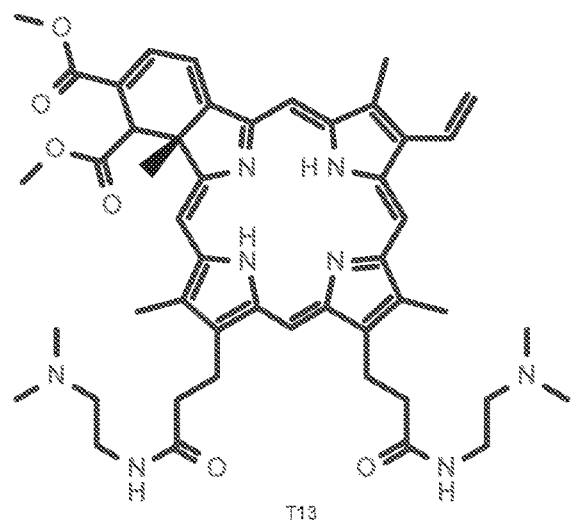
FIG. 8D shows structures of verteporfin derivative compounds T13-T16.
Figure 8D:
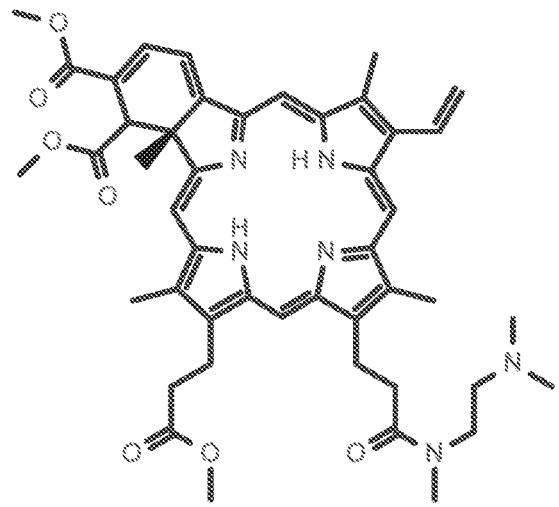
Figure 8D:
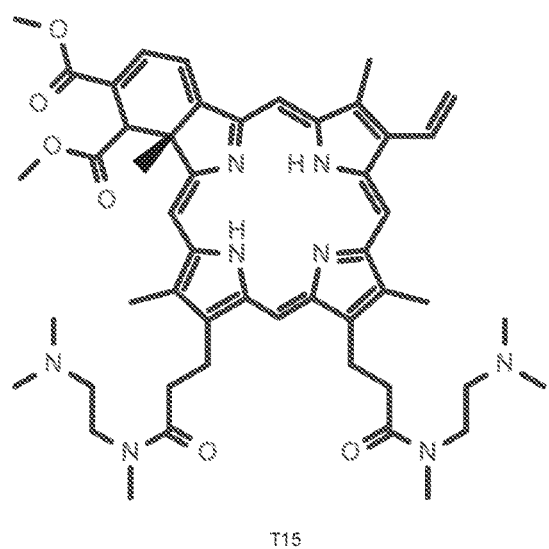
Figure 8D:
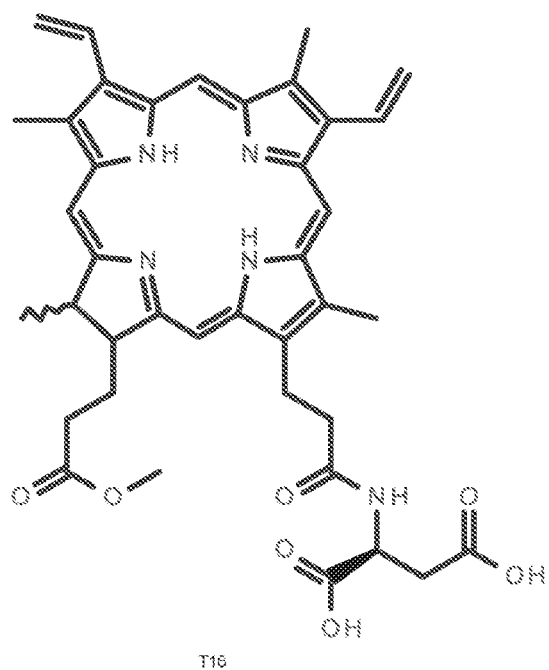
Figure 8E:
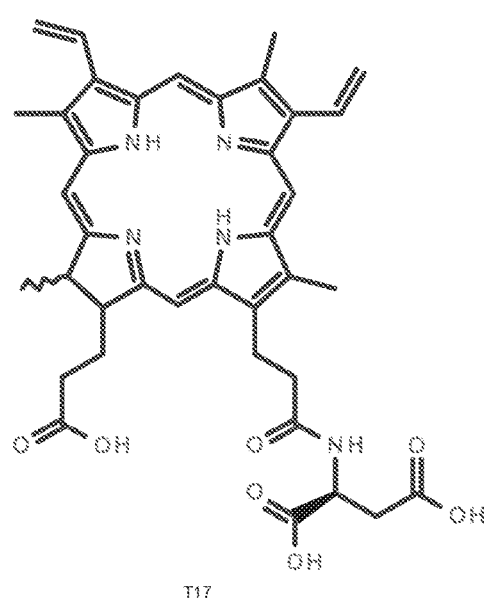
FIG. 8E shows structures of verteporfin derivative compounds T17-T20.
Figure 8E:
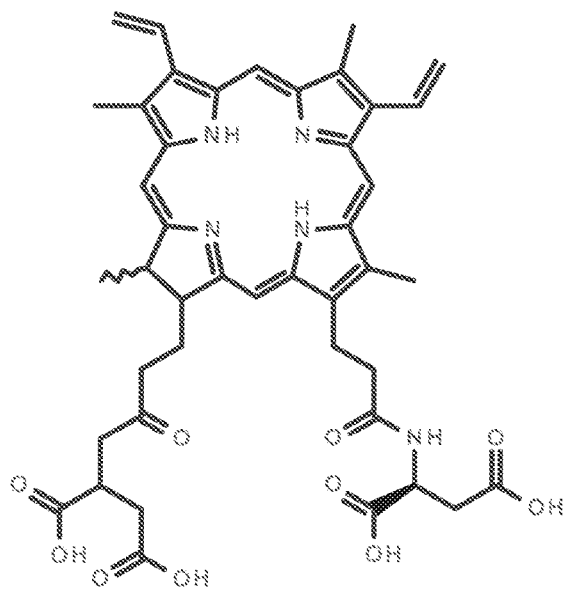
Figure 8E:
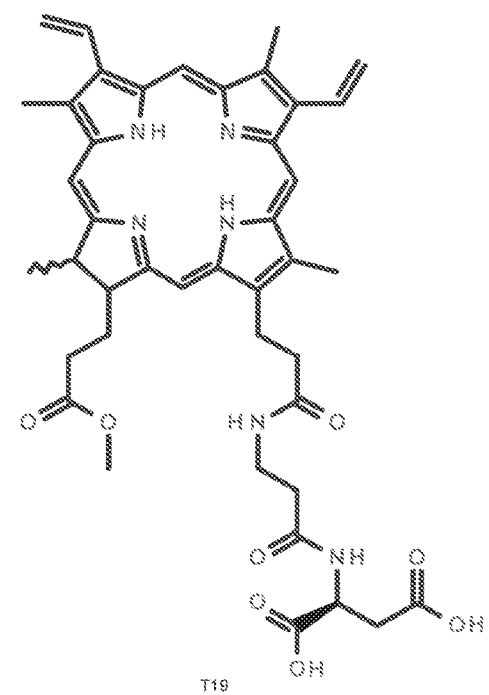
Figure 8E:
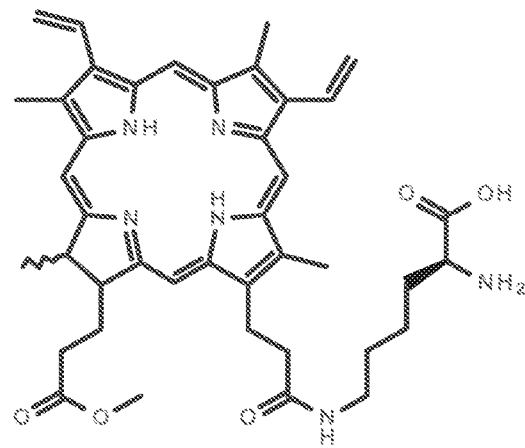
Figure 8F:
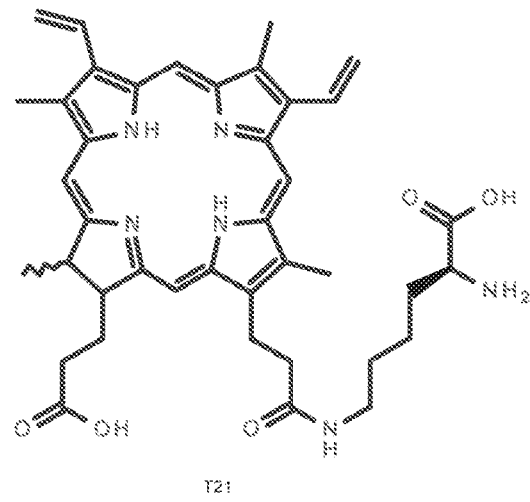
FIG. 8F shows structures of verteporfin derivative compounds T21-T24.
Figure 8F:
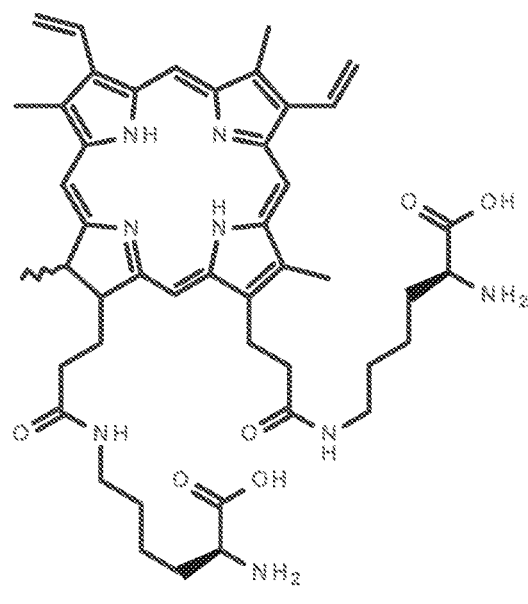
Figure 8F:
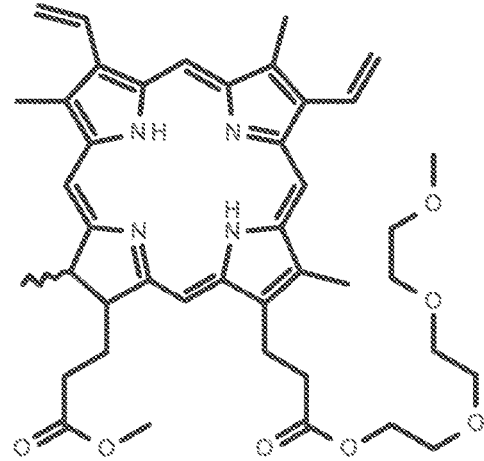
Figure 8F:
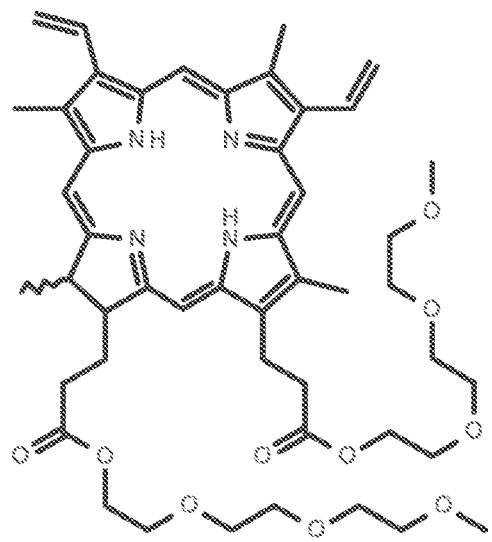
Figure 8G:
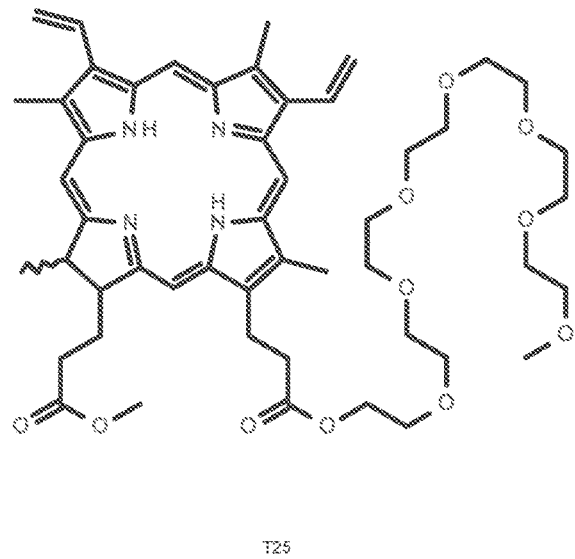
FIG. 8G shows structures of verteporfin derivative compounds T25-T28.
Figure 8G:
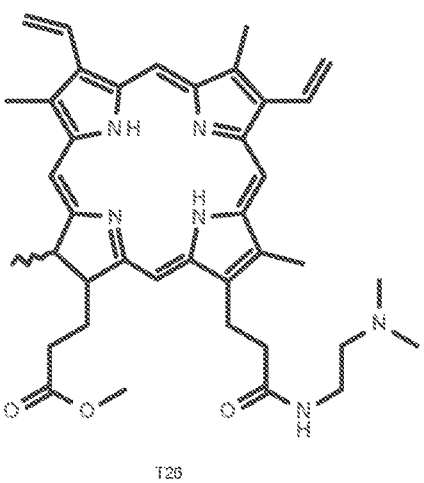
Figure 8G:
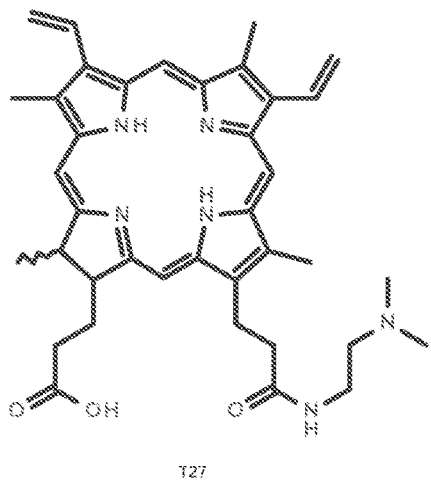
Figure 8G:
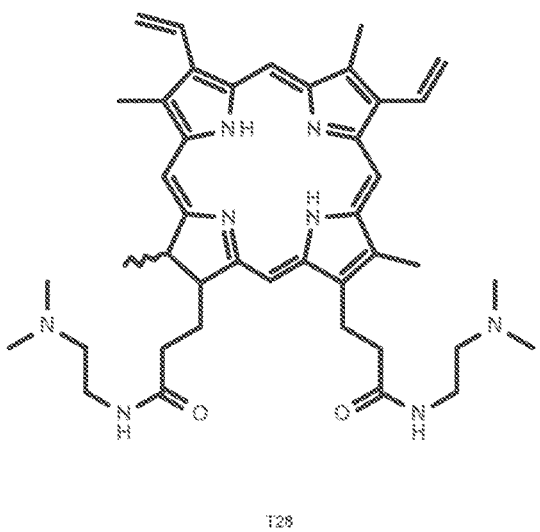
Figure 8H:
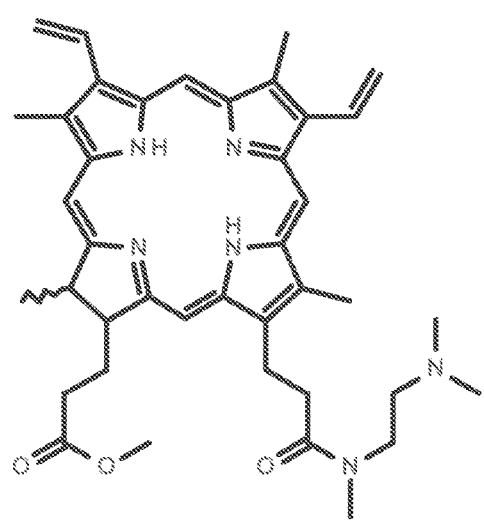
FIG. 8H shows structures of verteporfin derivative compounds T29-T30.
Figure 8H:
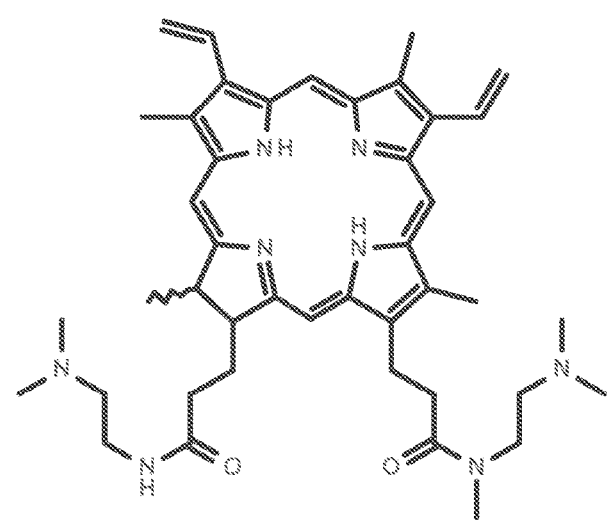

In some embodiments, the YAP1 inhibitor includes verteporfin. In some embodiments, the YAP1 inhibitor includes a verteporfin derivative compound. In some embodiments, the Yap1 inhibitor includes one or more of the compounds shown in FIG. 7 or 8 or a derivative thereof. In some embodiments, it is preferred that the YAP1 inhibitor is soluble in an aqueous solution, bioavailable, or both. In some embodiments, the degree of solubility in an aqueous solution may correlate with bioavailability.

In some embodiments, a method of treating a subject with a cancer further includes determining activation of the Sonic Hedgehog (SHH) signaling pathway in a biological sample.

The biological sample may be from a subject. The biological sample may include a cell. In some embodiments, the cell is a tumor cell. In some embodiments, determining the activation of the SHH pathway includes determining the expression of a gene of the Sonic Hedgehog (SHH) signaling pathway in the cell. A gene of the SHH signaling pathway can include, for example, SMO, PTCH1, PTCH2, GAS1, CDON, BOC, SUFU, GLI1, GLI2, SPHK1, SHROOM2, PDLIM3, OTX2, etc. In some embodiments, determining the activation of the SHH pathway includes determining the expression of a protein of the SHH signaling pathway. Determining the protein expression of a protein of the SHH signaling pathway can include at least one of quantifying the expression of the protein, comparing the level of expression of the protein to the level of expression in a reference sample, and comparing the level of expression of the protein to the level of expression in a subject without a cancer. In some embodiments, determining the activation of the SHH pathway includes determining the localization of a protein of the SHH signaling pathway. In some embodiments, determining the localization of a protein of the SHH signaling pathway can include, for example, determining the localization of the protein to the nucleus of a cell. In some embodiments, the YAP1 inhibitor can be administered to the subject based on the activity of the SHH signaling pathway.

In some embodiments, a method of treating a subject with a cancer further includes determining activation of the Hippo signaling pathway in a biological sample. The biological sample may be from a subject. The biological sample may include a cell. In some embodiments, the cell is a tumor cell. In some embodiments, determining the activation of the Hippo signaling pathway includes determining the expression of a gene of the Hippo signaling pathway in the cell. A gene of the Hippo signaling pathway can include, for example, YAP1, MST1/2, SAV1, LATS1/2, TAZ, TEAD1-4, CTGF, CCND1, BIRC5/Survivin, etc. In some embodiments, determining the activation of the Hippo signaling pathway includes determining the expression of a protein of the Hippo signaling pathway. In some embodiments, determining the expression of a protein of the Hippo signaling pathway can include at least one of quantifying the expression of the protein, comparing the level of expression of the protein to the level of expression in a reference sample, and comparing the level of expression of the protein to the level of expression in a subject without a cancer. In some embodiments, determining the activation of the Hippo signaling pathway includes determining the localization of a protein of the Hippo signaling pathway. Determining the localization of a protein of the Hippo signaling pathway can include, for example, determining the localization of the protein to the nucleus of a cell. In some embodiments, the YAP1 inhibitor can be administered to the subject based on the activity of the Hippo signaling pathway.

The expression of a protein may be determined by any suitable method including, for example, Western blot, ELISA, RT-PCT, etc. The expression of a gene may be determined by any suitable method including, for example, Northern blot, PCR, serial analysis of gene expression (SAGE), etc.

In another aspect, the present disclosure provides a method for determining responsiveness to a YAP1 inhibitor in a subject. In some embodiments, the method includes assaying a biological sample for the activation of at least one of the Sonic Hedgehog (SHH) signaling pathway and the Hippo signaling pathway and determining responsiveness to a treatment based on results from the assay. The biological sample may be from a subject including, for example, a human. The biological sample can include a cell. In some embodiments, the cell is a cancer cell including, for example, a tumor cell. In some embodiments, the treatment includes administration of verteporfin or a verteporfin derivative compound. In some embodiments, the treatment may be in vitro or ex vivo.

In a further aspect, the present disclosure provides a method for diagnosing a cancer in a subject including obtaining a biological sample from the subject and determining the level of YAP 1 protein expression in the sample. The biological sample may preferably include a cancer cell from the subject. The biological sample may be from a tumor. In some embodiments, the sample includes at least one of a medulloblastoma cell and a SHH-expressing cell. In some embodiments, the medulloblastoma can be a Sonic Hedgehog (SHH)-subgroup tumor. As shown in Example 1, YAP1 protein expression is increased in mouse models of medulloblastoma in which the SHH pathway is activated. In some embodiments, the cancer can include a cancer treated with at least one of a MAP Kinase inhibitor, a SHH inhibitor, and a SMO inhibitor. In some embodiments, the cancer may be at least one of a MAP kinase inhibitor resistant cancer, a SMO inhibitor resistant cancer, and a SHH inhibitor resistant cancer. In some embodiments, the cancer may include at least one of a MAP kinase-inhibitor resistant cell, a SMO-inhibitor resistant cell, and a SHH-inhibitor-resistant cell.

In a further aspect, the present disclosure provides the structure of YAP1 inhibitors, including the compounds shown in FIG. 8, and methods of synthesizing such YAP 1 inhibitors. The synthesis of molecules shown in FIG. 8 is described in Example 2.

Embodiments

Exemplary Methods of Treating a Subject with Cancer

In one aspect, this disclosure describes a method of treating a subject having a cancer, the method comprising administering a YAP1 inhibitor.

In some embodiments, the cancer comprises a YAP 1-expressing cell. In some embodiments, the cancer comprises a tumor including, for example, a brain tumor. In some embodiments, the cancer comprises a medulloblastoma including, for example, an SHH subgroup medulloblastoma. In some embodiments, the cancer comprises a pediatric tumor. In some embodiments, the cancer comprises a Sonic Hedgehog (SHH)-expressing cell. In some embodiments, the cancer comprises a cancer treated with at least one of a MAP Kinase inhibitor, a SHH inhibitor, and a SMO inhibitor. The cancer may have been previously treated with at least one of a MAP Kinase inhibitor, a SHH inhibitor, and a SMO inhibitor. In some embodiments, the cancer may be at least one of a MAP kinase inhibitor resistant cancer, a SMO inhibitor resistant cancer, and a SHH inhibitor resistant cancer. In some embodiments, the cancer comprises at least one of a MAP Kinase-inhibitor resistant cell, a SMO-inhibitor resistant cell, and a SHH inhibitor-resistant cell.

In some embodiments, the YAP1 inhibitor comprises verteporfin. In some embodiments, the YAP1 inhibitor comprises at least one verteporfin derivative compound.

In some embodiments, the method comprises at least one of intravenous administration, oral administration, intraperitoneal injection, and administration via injection into the spinal canal or into the ventricular compartment. The YAP1 inhibitor or a composition including the YAP1 inhibitor may be administered. In some embodiments, the method comprises administration of the YAP1 inhibitor in combination with at least one of surgery, radiation therapy, targeted therapy, or a chemotherapeutic agent. In some embodiments, the method comprises administration of the YAP1 inhibitor in combination with at least one of a SMO inhibitor, a MAP Kinase inhibitor, or a SHH pathway inhibitor.

In some embodiments, the subject is a human.

In some embodiments, the methods further comprises determining activity of the Sonic Hedgehog (SHH) signaling pathway in a biological sample from a subject; and administering the YAP1 inhibitor to the subject based on activity of the SHH signaling pathway. In some embodiments, the YAP1 inhibitor may be administered to the subject if activity of the SHH signaling pathway is determined to be increased. Determining activity of the Sonic Hedgehog (SHH) signaling pathway may comprise determining the expression of a gene of the Sonic Hedgehog (SHH) signaling pathway. A gene of the Sonic Hedgehog (SHH) signaling pathway may comprise at least one of SMO, PTCH1, PTCH2, GAS1, CDON, BOC, SUFU, GLI1, GLI2, SPHK1, SHROOM2, PDLIM3, and OTX2. Determining activity of the Sonic Hedgehog (SHH) signaling pathway may comprise at least one of determining the protein localization of a member of the SHH signaling pathway and determining the protein expression of a member of the SHH signaling pathway.

In some embodiments, the method comprises determining activity of the Hippo signaling pathway in a biological sample from a subject and administering the YAP1 inhibitor to the subject based on activity of the Hippo signaling pathway. In some embodiments, the YAP1 inhibitor may be administered to the subject if activity of the Hippo signaling pathway is determined to be increased. Determining activity of the Hippo signaling pathway may comprise determining the expression of a gene of the Hippo signaling pathway. A gene of the Hippo signaling pathway may comprise at least one of YAP1, MST1/2, SAV1, LATS1/2, TAZ, TEAD1-4, CTGF, CCND1, and BIRC5/Survivin. Determining activity of the Hippo signaling pathway may comprise at least one of determining the protein localization of a member of the Hippo signaling pathway and determining the protein expression of a member of the Hippo signaling pathway.

Exemplary Methods for Determining Responsiveness to a YAP1 Inhibitor

In another aspect, this disclosure describes a method for determining responsiveness to a YAP1 inhibitor in a subject, the method comprising: assaying a biological sample from the subject for activity of the Sonic Hedgehog (SHH) signaling pathway; and determining responsiveness of the subject to a treatment based on results from the assay.

In a further aspect, this disclosure describes a method for determining responsiveness to a YAP1 inhibitor in a subject, the method comprising: assaying a biological sample from the subject for activity of the Hippo signaling pathway; and determining responsiveness of the subject to a treatment based on results from the assay.

In yet another aspect, this disclosure describes a method for determining responsiveness to a YAP1 inhibitor in a subject, the method comprising: assaying a biological sample from the subject for activity of the Sonic Hedgehog (SHH) signaling pathway and the Hippo signaling pathway; and determining responsiveness of the subject to a treatment based on results from the assay.

In some embodiments, the YAP1 inhibitor may be administered to the subject if activity of the SHH signaling pathway or the Hippo signaling pathway or both is determined to be increased.

Determining activity of the Sonic Hedgehog (SHH) signaling pathway may comprise at least one of determining the expression of a gene of the Sonic Hedgehog (SHH) signaling pathway and determining the protein localization of a member of the SHH signaling pathway. A gene of the Sonic Hedgehog (SHH) signaling pathway may comprise at least one of SMO, PTCH1, PTCH2, GAS1, CDON, BOC, SUFU, GLI1, GLI2, SPHK1, SHROOM2, PDLIM3, and OTX2.

Determining activity of the Hippo signaling pathway may comprise at least one of determining the expression of a gene of the Hippo signaling pathway and determining the protein localization of a member of the Hippo signaling pathway. A gene of the Hippo signaling pathway may comprise at least one of YAP1, MST1/2, SAV1, LATS1/2, TAZ, TEAD1-4, CTGF, CCND1, and BIRC5/Survivin.

In some embodiments, determining activity of the Hippo signaling pathway may comprise at least one of determining the protein expression of a member of the SHH signaling pathway and determining the protein localization of a member of the SHH signaling pathway.

In some embodiments, the YAP1 inhibitor comprises verteporfin. In some embodiments, the YAP1 inhibitor comprises at least one verteporfin derivative compound.

Exemplary Methods for Diagnosing a Tumor

In another aspect, this disclosure describes a method for diagnosing a cancer in a subject, the method comprising: obtaining a biological sample from the subject; and determining the level of YAP1 expression in the biological sample.

In some embodiments, the biological sample is from a cancer including, for example, a tumor. In some embodiments, the tumor comprises a medulloblastoma. In some embodiments, the tumor comprises a brain tumor. In some embodiments, the tumor comprises a pediatric tumor.

In some embodiments, the method further comprises typing the medulloblastoma as a Sonic Hedgehog (SHH)-subgroup tumor or a non-SHH-subgroup tumor based on the level of YAP1 expression.

Exemplary Compounds, Compositions, and Methods of Using

This disclosure also describes verteporfin derivative compounds and compositions including at least one verteporfin derivative compound. In some embodiments, the composition is a pharmaceutical composition including the verteporfin derivative compound and a pharmaceutically acceptable excipient.

This disclosure further describes methods of using those compounds and compositions. In some embodiments, the method includes administering the composition to a subject with cancer.

In some embodiments, the cancer comprises a cell expressing YAP1. In some embodiments, the cancer comprises a tumor. In some embodiments, the cancer comprises a brain tumor. In some embodiments, the cancer comprises a medulloblastoma including, for example, a SHH group medulloblastoma. In some embodiments, the cancer comprises a pediatric tumor. In some embodiments, the cancer comprises a Sonic Hedgehog (SHH)-expressing cell. In some embodiments, the cancer comprises a cancer treated with at least one of a MAP Kinase inhibitor, a SHH inhibitor, and a SMO inhibitor. The cancer may have been previously treated with at least one of a MAP Kinase inhibitor, a SHH inhibitor, and a SMO inhibitor. In some embodiments, the cancer comprises a MAP Kinase inhibitor resistant cell. In some embodiments, the cancer comprises a SHH inhibitor resistant cell. In some embodiments, the cancer comprises a SMO inhibitor resistant cell.

In some embodiments, the method includes intravenous administration of the composition. In some embodiments, the method includes oral administration of the composition. In some embodiments, the method includes intraperitoneal injection of the composition. In some embodiments, the method includes administration of the composition via injection into the spinal canal. In some embodiments, the method includes administration of the composition into the ventricular compartment.

In some embodiments, the method comprises administration of the composition in combination with at least one of surgery, radiation therapy, targeted therapy, or a chemotherapeutic agent. In some embodiments, the method comprises administration of the composition in combination with at least one of a SMO inhibitor, a MAP Kinase inhibitor, and a SHH pathway inhibitor. The SMO inhibitor, MAP Kinase inhibitor, or SHH pathway inhibitor may be administered in the same or an additional pharmaceutical composition. In some embodiments, the method comprises administration of the composition in combination with verteporfin.

In some embodiments, the subject is a human.

In some embodiments, the method further comprises determining the activity of the Sonic Hedgehog (SHH) signaling pathway in a biological sample from a subject; and administering the composition to the subject based on the activation of the SHH signaling pathway. Determining the activation of the SHH signaling pathway may comprise at least one of determining the activity of a gene of the SHH signaling pathway, determining the protein localization of a member of the SHH signaling pathway, and determining the protein expression of a member of the SHH signaling pathway. A gene of the SHH signaling pathway may comprise at least one of SMO, PTCH1, PTCH2, GAS1, CDON, BOC, SUFU, GLI1, GLI2, SPHK1, SHROOM2, PDLIM3, and OTX2.

In some embodiments, the method further comprises determining the activity of the Hippo signaling pathway in the tumor and administering the composition based on the activity of the Hippo signaling pathway. Determining the activity of the Hippo signaling pathway may comprise at least one of determining the activity of a gene of the Hippo signaling pathway, determining the protein localization of a member of the Hippo signaling pathway, and determining the protein expression of a member of the Hippo signaling pathway. A gene of the Hippo signaling pathway may comprise at least one of YAP1, MST1/2, SAV1, LATS1/2, TAZ, TEAD1-4, CTGF, CCND1, and BIRC5/Survivin.

The present invention is illustrated by the following examples. It is to be understood that the particular examples, materials, amounts, and procedures are to be interpreted broadly in accordance with the scope and spirit of the invention as set forth herein.

Examples

Example 1—YAP Inhibition for Oncology Applications

Through genetic studies using mouse models of medulloblastoma, this Example shows that YAP is required for SHH-induced medulloblastoma and the maintenance of cancer stem cells. This Example also shows that YAP is aberrantly activated independent of cell of origin, indicating that YAP activation is a common event in SHH-induced tumors. In addition, YAP protein, but not RNA, is elevated in SHH-induced tumors that acquire resistance to SHH-inhibitors (GDC-0449 and LDE 225), indicating that YAP is involved in therapy resistance to SHH inhibitors as well as MAPK inhibitors. This Example demonstrates that YAP1 is a target for treating not only SHH-induced tumors but also others that are undergoing targeted therapy treatment.

Verteporfin (VP) can inhibit YAP:TEAD binding (Liu-Chittenden et al., *Genes and Development*, 2012, 26(12): 1300-5); however, VP is highly insoluble and may be unsuitable for many oncology applications. Therefore compounds with more drug-like properties are needed.

Example 1A—YAP is Expressed in the SHH Subgroup but not G3 Subgroup of Human Medulloblastoma To validate physiologically relevant models of human medulloblastoma, YAP expression in patient derived xenografts of medulloblastoma was analyzed. YAP expression was observed in both SHH subgroup models while no YAP expression was observed in a G3 subgroup model (FIG. 1A). This observation is consistent with previously published large scale genomics analysis (Northcott et al., *Nature*, 2012, 488(7409): 49-56; Fernandez et al., *Genes and Development*, 2009, 23(23):2729-41) and indicates that the models used are consistent with human disease.

Example 1B—YAP is Necessary for SHH Induced Medulloblastoma Formation

Figure 1B:
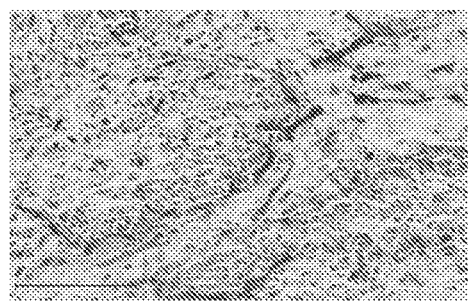
FIG. 1B) YAP expression in SMO-M2; GFAP-cre mouse medulloblastoma detected by immunohistochemistry.
Figure 1C:
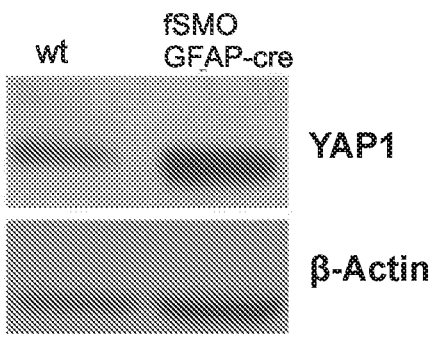
FIG. 1C) Western blot analysis showing increased YAP1 protein levels in SMO-GFAP-cre tumors compared to YAP1 protein levels in the cerebellum of a wildtype littermate.
Figure 1D:
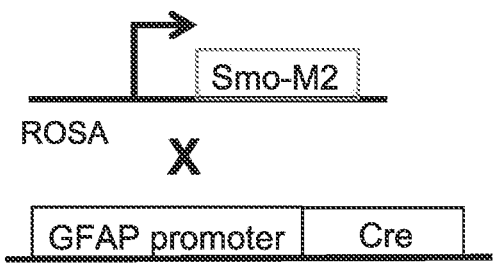
FIG. 1D) Schematic of mouse strains used to generate YAP1$^{ff}$Smo-M2;GFAP-cre mice.
Figure 1E:
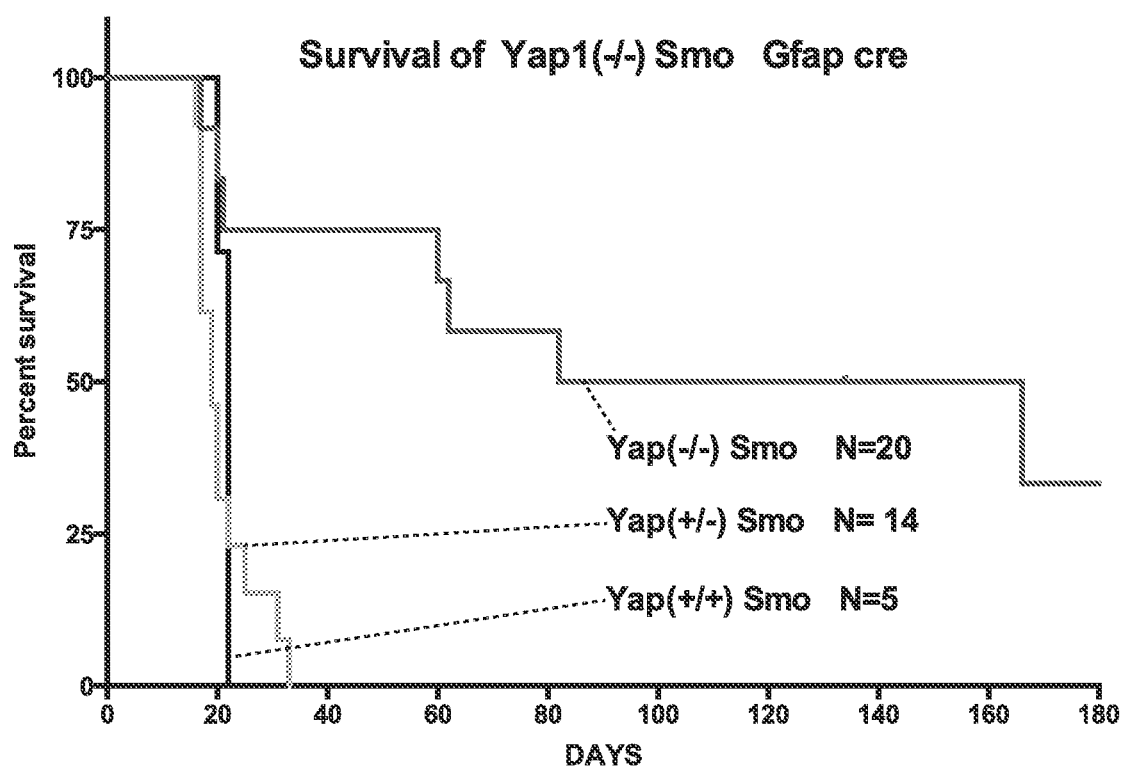
FIG. 1E) Kaplan-Meier survival curve for YAP wildtype (+/+), YAP heterozygous (f/+ or +/−), and YAP null (f/f or −/−) SMO-M2;GFAP-cre mice. Smo-M2: mutated mouse smoothened homolog (*Drosophila*) gene; GFAP-cre: cre recombinase expression directed by the mouse glial fibrillary acidic protein (GFAP) promoter; YAP 1$^{ff}$: YAP1 flox/flox, that is, YAP1 flanked by two cre recombinase recognition sites. ROSA: Gt(ROSA)26Sor locus.

To test whether YAP plays a critical role in SHH-induced medulloblastomas, YAP1 was genetically deleted in the neural stem/progenitor cells that activate the SHH pathway. To do this, expression of YAP by Smo-M2;GFAP-Cre medulloblastomas, which express activated form of SMO in developing neural stem cells, was confirmed (FIG. 1B, FIG. 1C). A floxed allele of YAP1 (FIG. 1B) was intercrossed with Smo-M2;hGFAP-Cre (FIG. 1D) to generate YAP $1^{fl}$; Smo-M2;GFAP-cre and control littermate mice. While 100% SMO-M2;GFAP-cre mice develop medulloblastomas and succumb to disease by weaning age, ~50% of mice with loss of both copies of YAP1 were rescued from tumor formation and survived greater than 1 year (FIG. 1E). YAP $1^{fl}$;Smo-M2;GFAP-cre mice that survived weaning age showed no neural symptoms including hydrocephalus or ataxia, suggesting that genetic rescue was completely penetrant. Immunohistochemical analyses of rescued brains showed undetectable to minimal disease. Together, the results of this genetic study indicate that YAP1 has a critical role in SHH-induced medulloblastomas.

Example 1C—YAP is Necessary for Tumor Maintenance but not Initiation

Figure 2A:
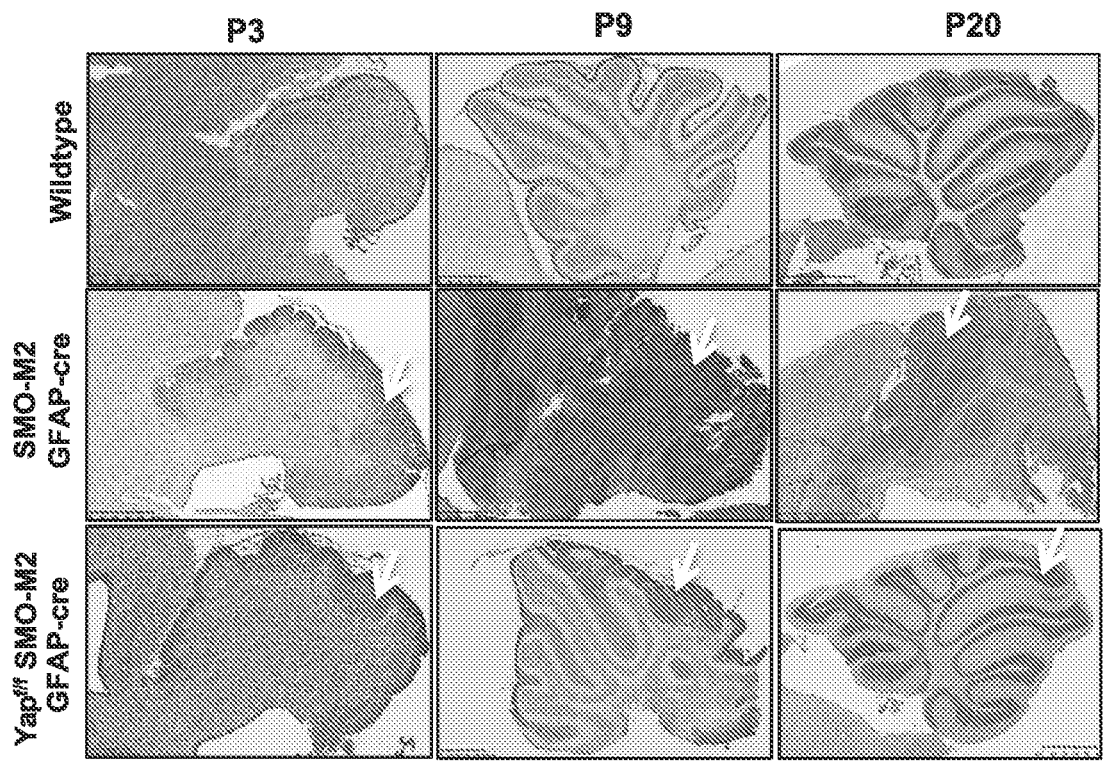
FIG. 2A) Hematoxylin and Eosin (H&E) staining of cerebella from wildtype, SMO-M2; GFAP-cre, and YAP 1$^{ff}$;Smo-M2;GFAP-cre mice at postnatal days 3, 9, and 20 (p3, p9, and p20).
Figure 2B:
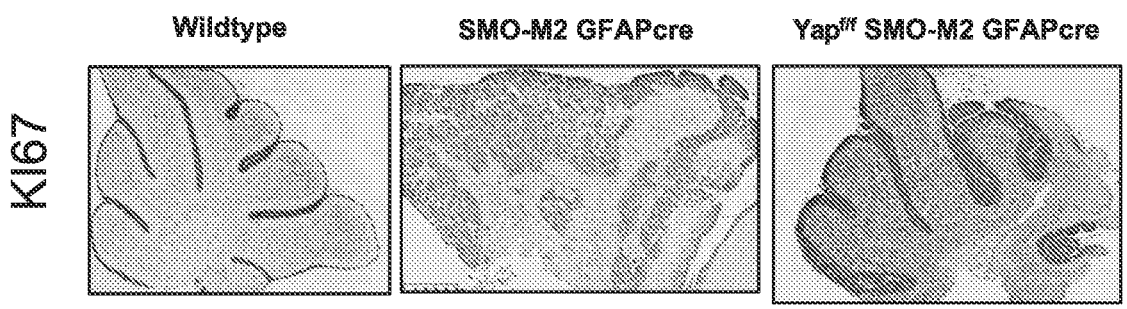
FIG. 2B) Immunohistochemical analysis of proliferation marker KI67 in wildtype, SMO-M2;GFAP-cre, and YAP 1$^{ff}$;Smo-M2; GFAP-cre mice at p9.

To determine the mechanism of tumor suppression by YAP1 deletion, early postnatal brains of YAP $1^{fl}$;Smo-M2; GFAP-cre (triple transgenic) mice were analyzed along with brains from their littermates. At postnatal day 3, YAP $1^{fl}$;Smo-M2;GFAP-cre cerebellum is similar to YAP$1^{+/+}$; Smo-M2;GFAP-cre brains, as indicated by thickened external germinal/granule layer (EGL) layer with KI67+ dividing cells (arrows in FIG. 2A). Markers of apoptosis (e.g., cleaved Casp3) and proliferation (e.g., KI67) show that in the triple mutant brain, there is no increase in apoptosis at postnatal day 3 (p3) or p9. However, there are decreased numbers of KI67+ cells in the triple transgenic brain accompanied by normalization of histology and increased number of neurons, compared to Smo-M2;GFAP-cre brains (FIG. 2B). By postnatal day 20, asymptomatic YAP $1^{ff}$;Smo-M2; GFAP-cre brains look normal, although small regions of residual disease were observed in some mice. Histologically the cerebellum appears normal with proper foliation and neuronal differentiation (FIG. 2A), consistent with their normal behavior. Together, these observations suggest that YAP1 is not critical for initial hyperplasia induced by elevated SHH signaling in the EGL progenitor cells but its expression is required to maintain actively dividing cells in growing tumors. Also the normalization of cerebellar development in the absence of increased apoptosis and normal differentiation of internal granular layer (IGL) neurons suggest that elevated YAP expression in tumor cells blocks normal differentiation and forces cells to proliferate.

Figure 3A:
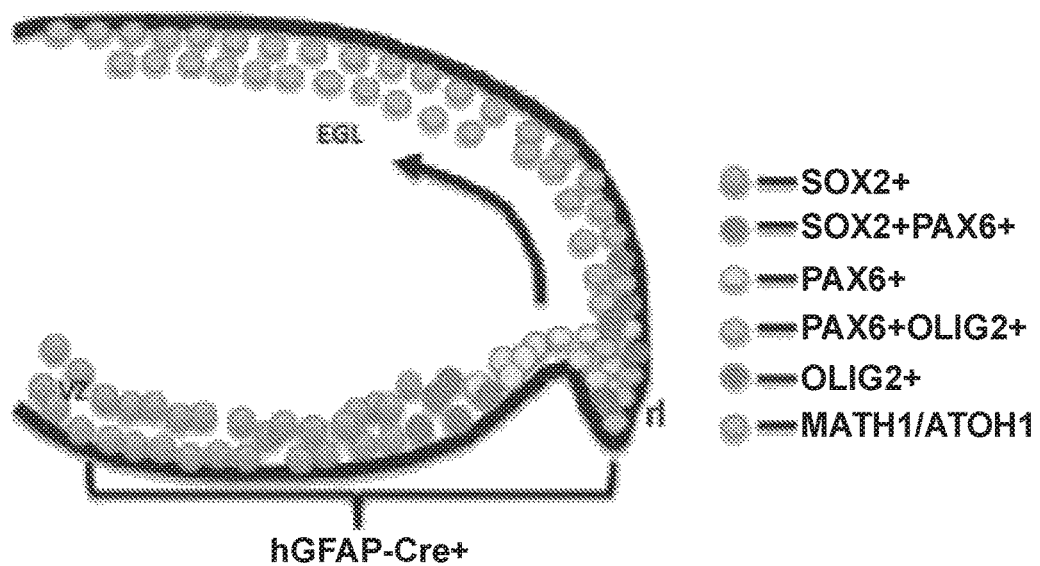
FIG. 3A) A schematic of known transcription factors that are expressed at different maturation stages of cerebellar precursor maturation.
Figure 3B:
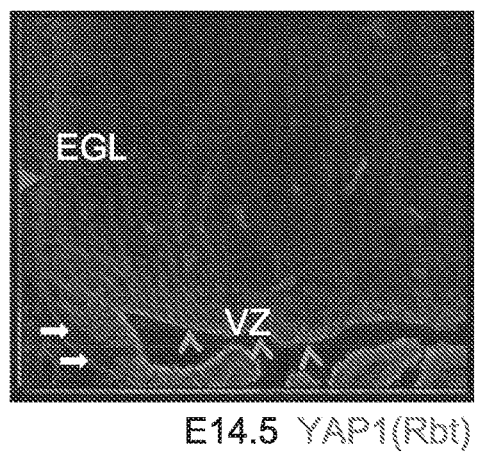
FIG. 3B) YAP1 antibody staining in embryonic day 14.5 (E14.5) wildtype cerebellum in the ventricular zone (VZ); EGL indicates that external germinal/granule layer.
Figure 3C:
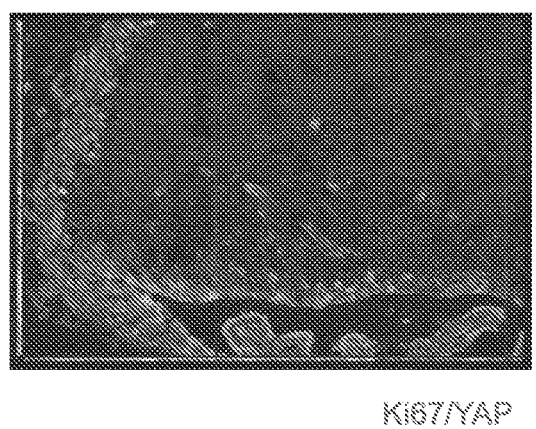
FIG. 3C) Double immunofluorescence analysis of YAP1 (red) and KI67 (green) in E14.5 wildtype cerebellum.
Figure 3D:
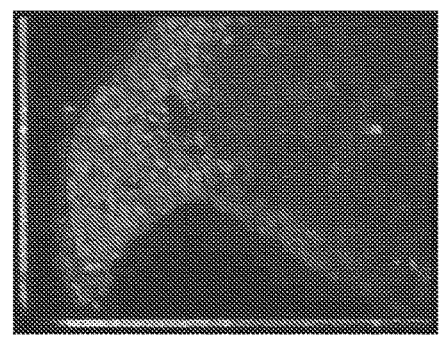
FIG. 3D) Double immunofluorescence analysis of YAP1 (red) and PAX6 (green) in E14.5 wildtype cerebellum.

Example 1D—YAP is Expressed in Neural Stem Cells in the Ventricular Zone but not in EGL Progenitors in the Developing Cerebellum To gain insight into YAP1 activation in SHH-induced tumors, YAP1 expression patterns in developing wildtype cerebellum were analyzed. Using previously characterized markers of different neural stem and progenitor cells (FIG. 3A), which populations express YAP1 at detectable levels was determined. Strong YAP expression in the ventricular zone (FIG. 3B), containing SRY (sex determining region Y)-box 2 (SOX2)-positive neural stem cells was observed, and YAP was both nuclear and cytoplasmic. Most of paired box 6 (PAX6)-positive stem/progenitor cells had downregulated YAP expression and few showed detectable levels of YAP1 by embryonic day 14.5 (FIG. 3C, FIG. 3D). No nuclear YAP expression in oligodendrocyte lineage transcription factor 2 (OLIG2)-positive or (atonal bHLH transcription factor 1) MATH1/ATOH1-positive external germinal/granule layer (EGL) progenitor cells was detected, indicating that committed EGL neural progenitor cells down-regulate YAP1 expression in the developing brain.

Example 1E—YAP is Re-Expressed in SHH Medulloblastoma Cells

Figure 3E:
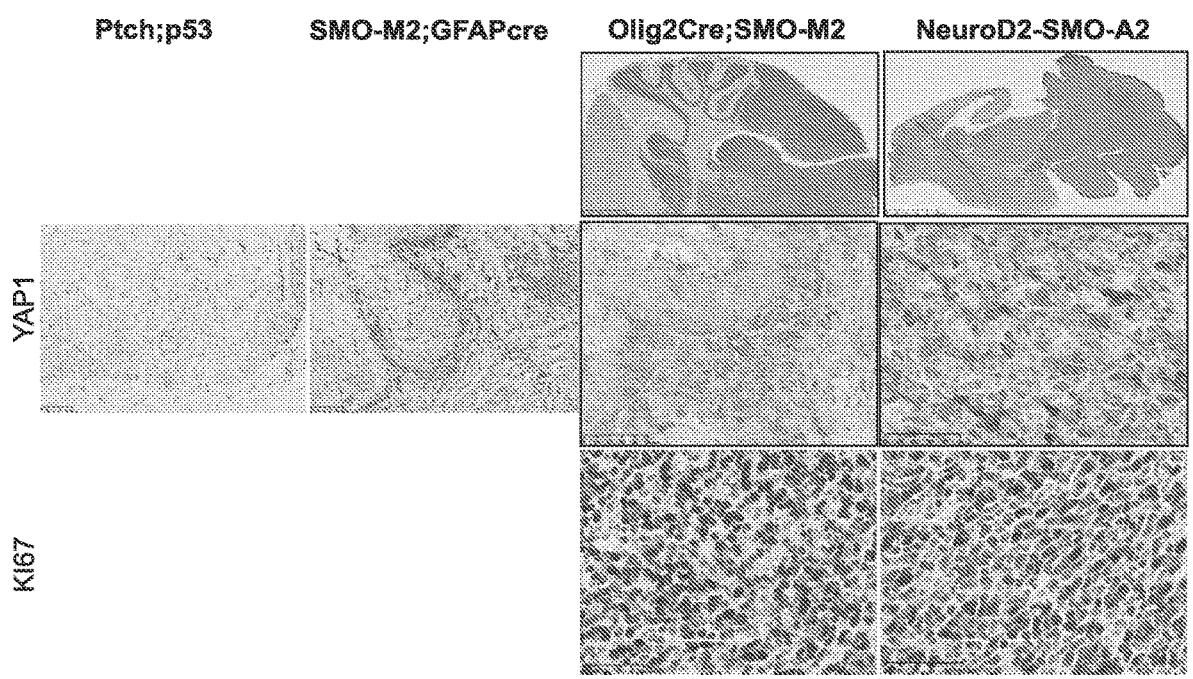
FIG. 3E) HE, YAP1, and KI67 expression in 4 different mouse models of SHH medulloblastoma (Ptch;p53; SMO-M2;GFAP-cre; Olig2Cre;SMO-M2; and NeuroD2-SMO-A2).

It is intriguing that while about 50% of YAP $1^{ff}$;Smo-M2; GFAP-cre mice were rescued from tumor formation, the other 50% continued to develop tumors even in the absence of YAP1. A potential explanation is that cells of different origins may have differential requirements for YAP1 as a cooperating oncogene. To test this possibility, YAP expression was analyzed in 4 different mouse models of medulloblastoma in which SHH pathway is activated at different time points and cell types during cerebellar development. In Ptch and Ptch;p53 (N=4) mice, in which there is germline deletion of Ptch, nuclear YAP-positive cells were observed all tumors (FIG. 3E). Similar clusters of YAP1-positive cells were observed in all tumors (N=5) in SMO-M2;GFAP-cre tumors, in which an activated form of SMO is turned on in neural stem cells (FIG. 3E). In NeuroD2-SMO-A2 and Smo-M2;OLIG-cre mice, where activated SMO is turned on in EGL progenitors that normally do not express YAP1, YAP expression in all tumors was observed (FIG. 3E). These results indicate that YAP is activated in all SHH-induced tumors regardless of their cells of origin, and that YAP expression in SHH tumors is not due to sustained expression in transformed cells that normally express YAP but, rather, YAP expression is aberrantly induced in tumors.

Figure 4A:
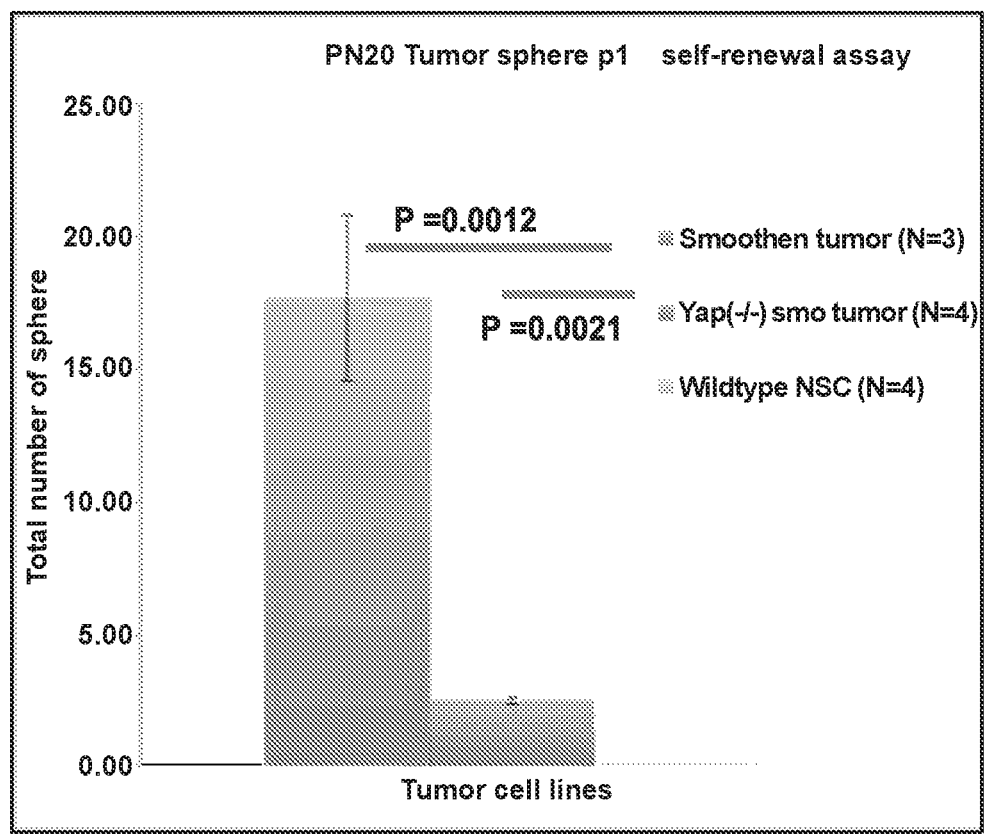
FIG. 4A) Sphere formation in SMO-M2; GFAP-cre and YAP 1$^{ff}$;Smo-M2;GFAP-cre tumors and wild type cells.
Figure 4B:
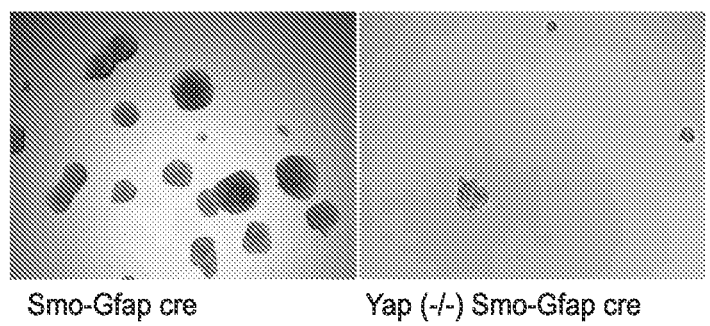
FIG. 4B) Images of secondary spheres after 1 week of clonal density culture from SMO-M2;GFAP-cre and YAP 1$^{ff}$;Smo-M2;GFAP-cre tumorsphere lines.

Example 1F—YAP is Required for Cancer Cell Self-Renewal but not Normal Neural Stem Cells YAP has a well-established role in homeostasis of multiple adult tissue stem cell compartments. To determine whether YAP expression is necessary for self-renewal of SHH medulloblastoma cells, secondary sphere formation assays were performed. All SMO-M2;GFAP-cre tumors generated sphere-forming cultures that could be passaged when dissociated into single cells in serum-free stem cell medium. When plated at a clonal density (1 cell/microliter (cell/µL)) at passage 1 and passage 2, 15 percent (%) to 20% of cells consistently formed secondary spheres (FIG. 4A). In contrast, the number of sphere forming cells in YAP $1^{ff}$; Smo-M2;GFAP-cre tumors was greatly reduced (less than 3%, FIG. 4A) and quickly depleted of self-renewing cells by passage 2 (FIG. 4A, FIG. 4B). This result strongly suggests that YAP1 is required for self-renewal of cancer stem cells in SHH medulloblastomas.

Figure 4C:
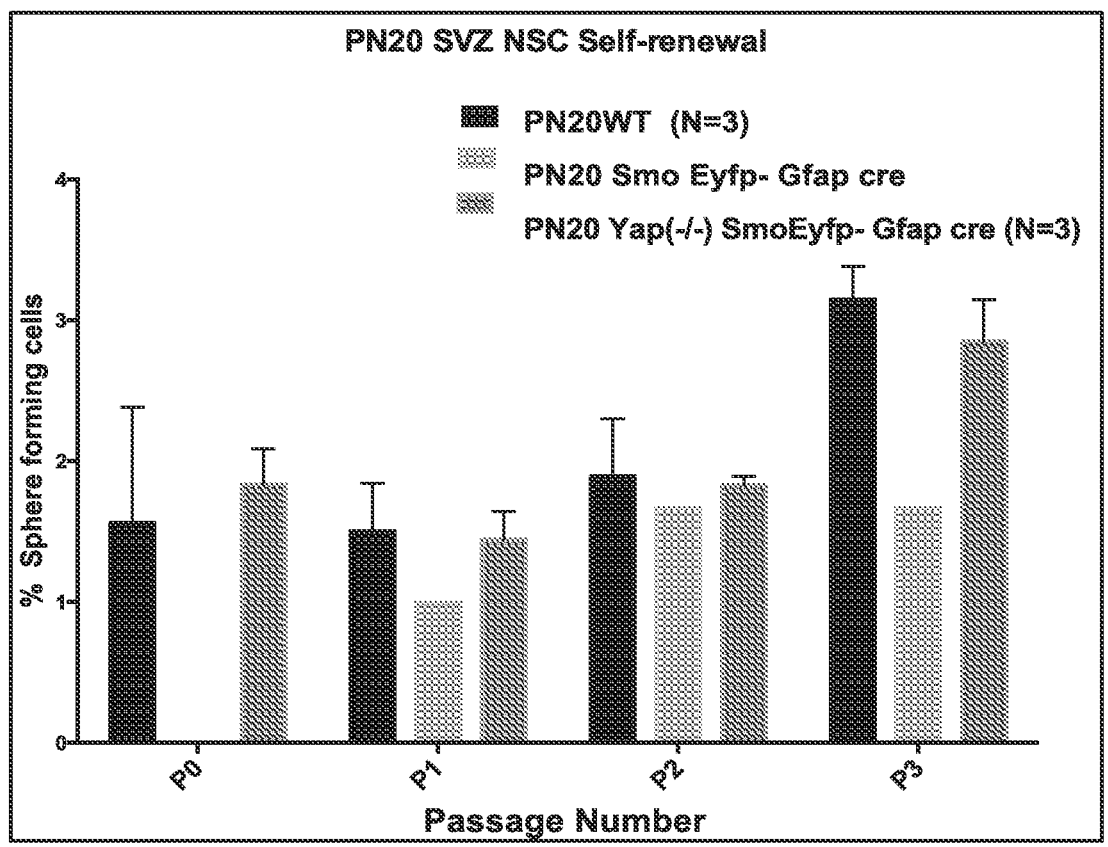
FIG. 4C) Secondary sphere formation in SMO-M2;GFAP-cre and YAP 1$^{ff}$;Smo-M2;GFAP-cre neural stem cells isolated from the SVZ from p20 pup brains.
Figure 4D:
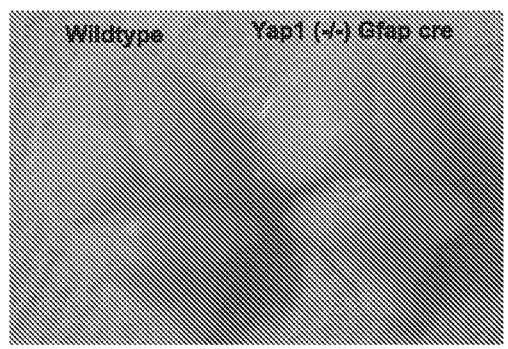
FIG. 4D) Gross pictures of adult brains from wildtype and YAP;GFAP-cre littermates.
Figure 4E:
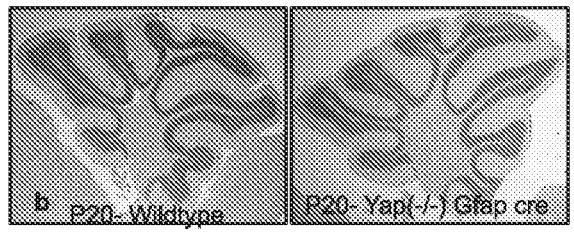
FIG. 4E) H&E analysis of control and YAP-null cerebellum.
Figure 4F:
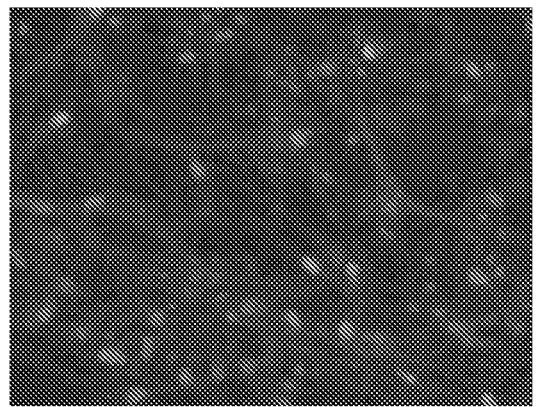
FIG. 4F) YAP expression in primary cells isolated from Smo-M2; GFAP-cre medulloblastomas.

To test whether these results reflect endogenous function of YAP 1 in neural stem cell (NSC) self-renewal, NSCs were isolated from the subventricular zone (SVZ) region of wildtype, SMO-M2;GFAP-cre, and YAP $1^{ff}$;Smo-M2; GFAP-cre mice. Unlike the tumor cells, significant reduction in self-renewal ability of NSCs from YAP $1^{ff}$;Smo-M2; GFAP-cre mice was not observed (FIG. 4C). These results together indicate that YAP1 activation is necessary for tumor cell self-renewal but not normal NSCs. To test whether YAP function is necessary for brain development, YAP $1^{ff}$; GFAP-cre and YAP $1^{ff}$;Emx-cre mice were generated and analyzed. Interestingly, 100% of YAP $1^{ff}$; GFAP-cre and YAP $1^{ff}$;Emx-cre mice were viable, indicating that YAP1 is not absolutely necessary for brain development. A minor reduction in the number of cortical neurons that form in YAP $1^{ff}$;Emx-cre mice was observed, but the mutant brains were grossly normal (FIG. 4D, FIG. 4E).

Example 1G—Verteporfin Treatment Extends Survival in SHH Medulloblastoma Models

Since genetic analysis indicated that inhibiting YAP function blocks SHH medulloblastoma growth while minimally affecting normal brain development, inhibiting YAP function has therapeutic potential. The therapeutic potential of a small molecule inhibitor of YAP, verteporfin (VP), an inhibitor of YAP:TEAD interaction, was tested.

Figure 5A:
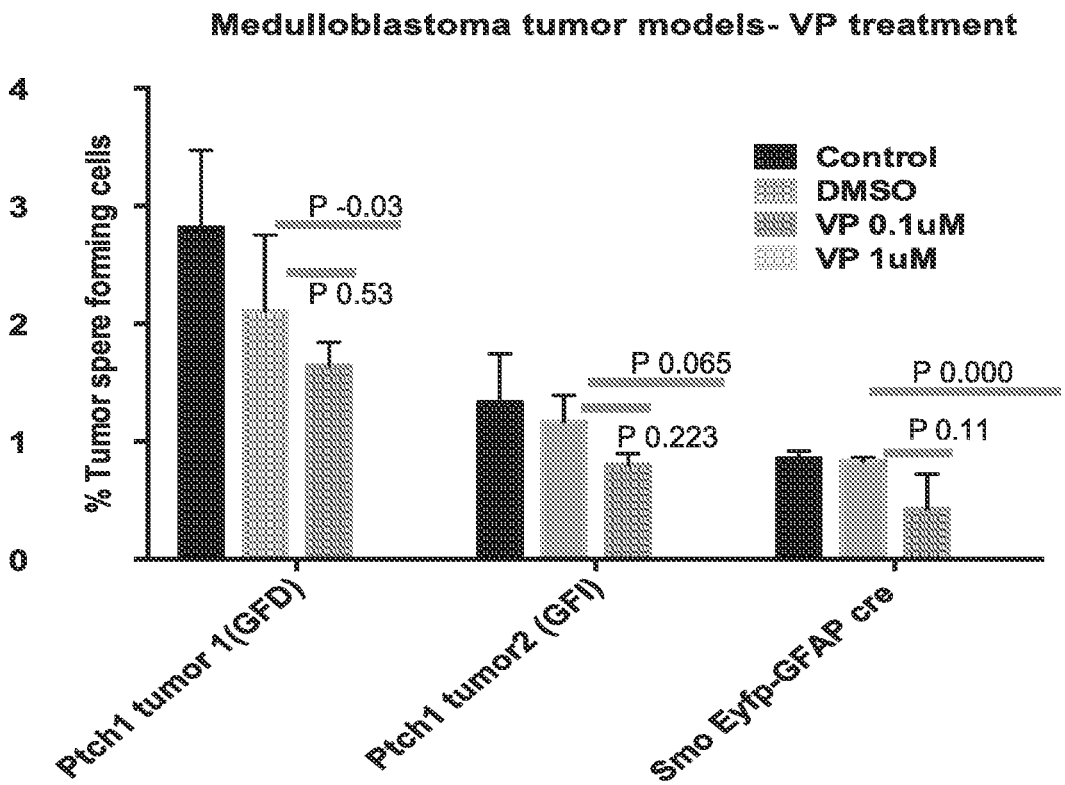
FIG. 5A) Verteporfin treatment completely abrogates self-renewal of cells from medulloblastoma tumor models: Ptch;p53 and Smo-M2;GFAP-cre medulloblastoma cells in vitro (100% suppression at 1 M and ~50% suppression at 0.1 µM) (n=3; error bars indicate SEM).
Figure 5B:
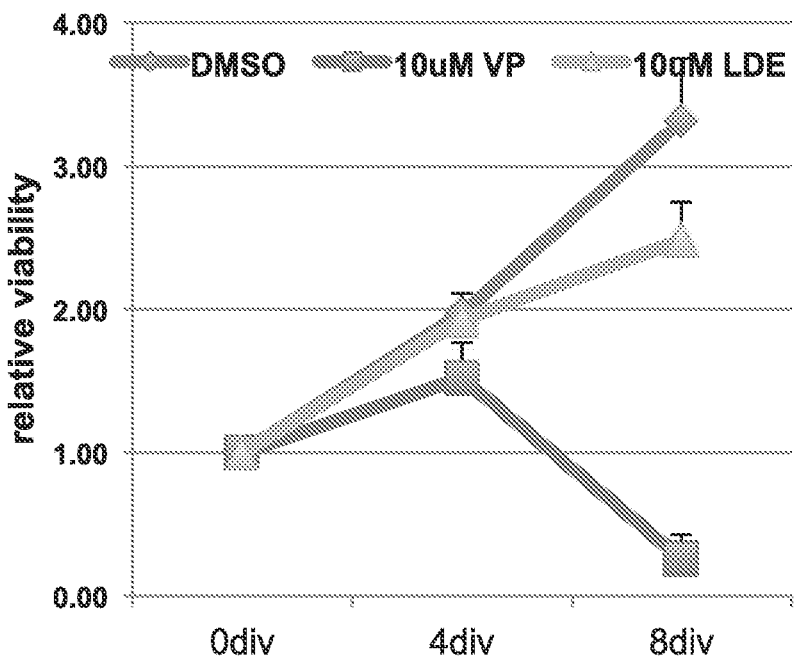
FIG. 5B) The effect of VP treatment and treatment of SHH-inhibitor LDE 225 (LDE) on tumor growth ex vivo was measured using tumor slice cultures from Smo-M2;GFAP-cre medulloblastomas.
Figure 5C:
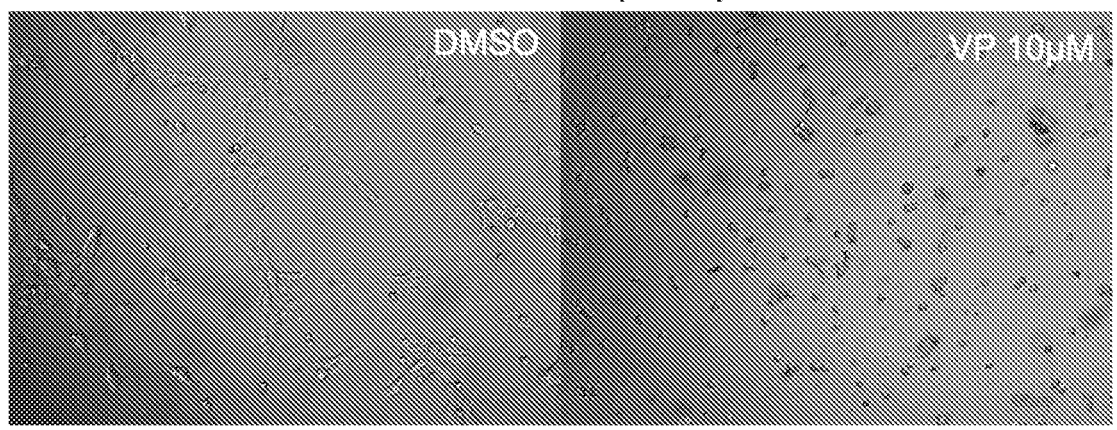
FIG. 5C) VP treatment on MED311 human patient-derived xenograft (PDX) SHH medulloblastoma cells induces morphological changes consistent with apoptosis.

VP treatment of multiple mouse SHH subgroup tumorspheres (derived from Ptch;p53 and SMO;GFAP-cre models) suppressed self-renewal at 100 nanomolar (nM) and completely suppressed self-renewal at 1 micromolar (µM) in vitro (FIG. 5A). Furthermore, Smo;GFAP-cre tumor tissue explants grown as intact tumor slices ex vivo showed significant response to VP treatment (FIG. 5B), indicating that VP is a potent inhibitor of SHH-induced medulloblastoma cells and tissue. To test YAP function in human cells, primary cells from a SHH subgroup PDX model (MED311) were isolated and treated with VP. MED311 cells showed a significant morphology change at 24 hours post-VP treatment (FIG. 5C) and reduced proliferation upon VP treatment.

Example 1H—YAP is Over-Expressed in SMO Inhibitor Resistant SHH Tumors

Figure 6A:
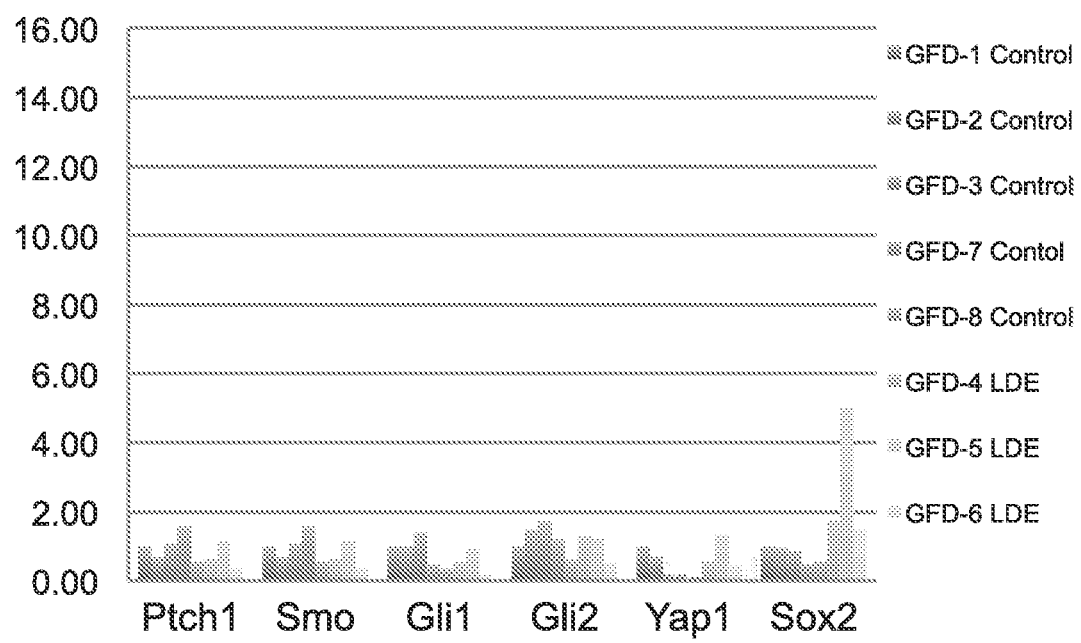
FIG. 6A) RT-PCR analysis of control and LDE-treated tumors, harvested when they became resistant to LDE-225 (LDE) treatment.
Figure 6B:
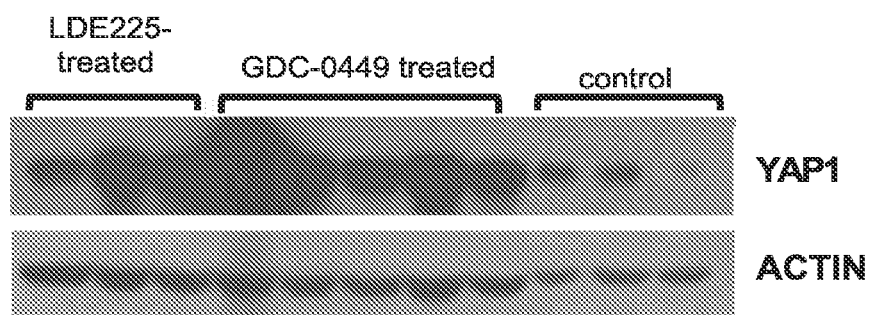
FIG. 6B) Western blot analysis showing increased YAP1 protein levels in tumors treated with SHH inhibitors, LDE225- and GDC-0449, compared to control treated tumors.
Figure 6C:
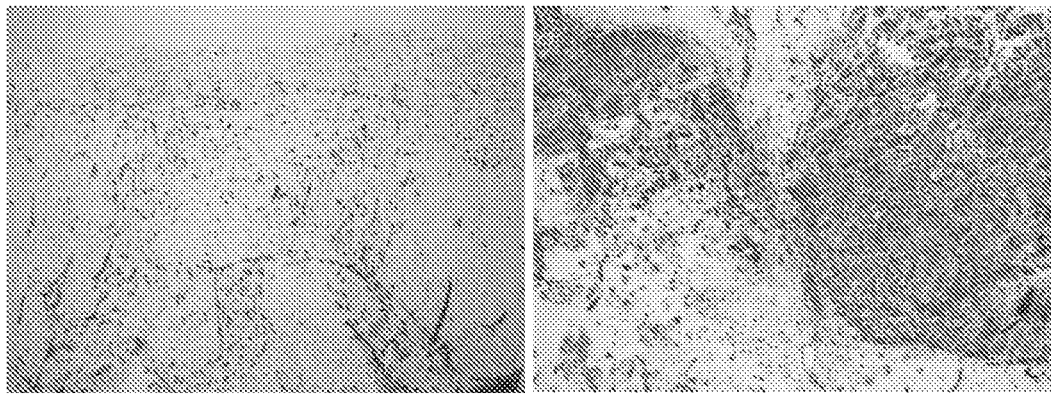
FIG. 6C) Immunohistochemistry showing increased YAP1 expression in LDE225-resistant tumors (right panel), compared to control-treated tumors (left panel).
Figure 6D:
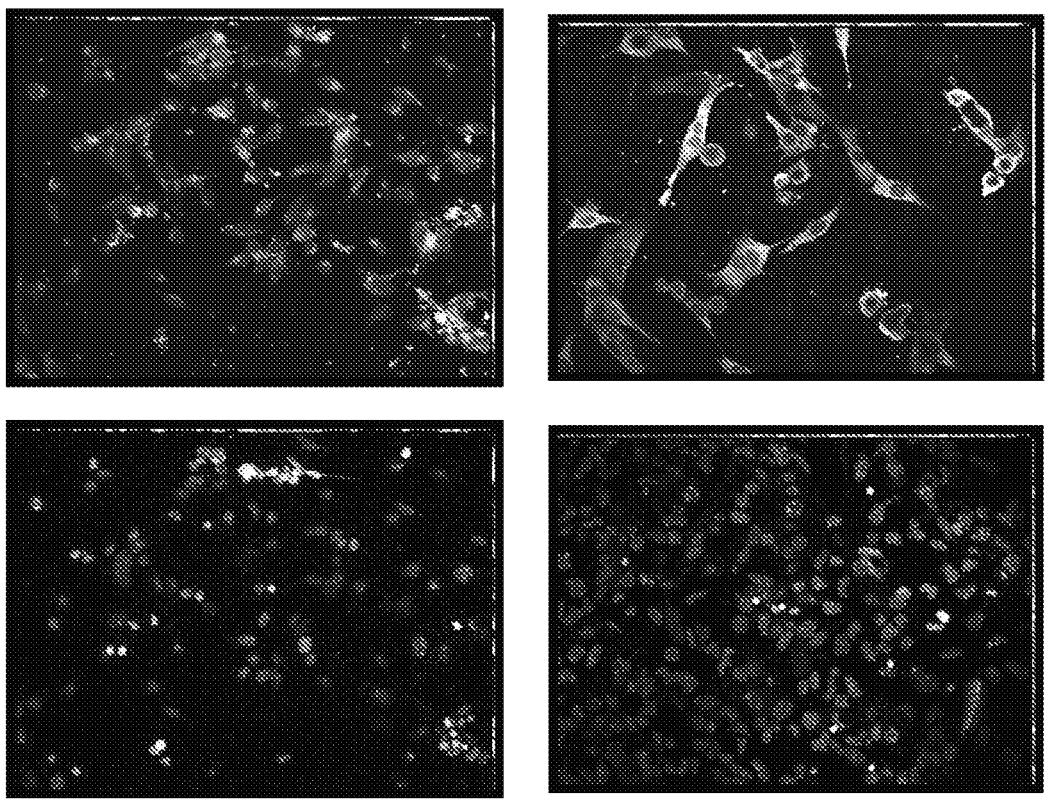
FIG. 6D) Immunofluorescence analysis showing nuclei (DAPI, bottom panels) and YAP1 expression (top panels) in cells isolated from LDE225-treated tumors (right panels), compared to cells isolated from control treated tumors (left panels). YAP1 expression is increased in cells isolated from LDE225-treated tumors (right panels), compared to cells isolated from control treated tumors (left panels).

In both mouse models and in patients, treatment with SMO inhibitors (LDE225 and GDC-0449/visomodegib)

blocks SHH signaling, resulting in significant tumor reduction. Unfortunately, many patients develop resistance to SMO inhibitors over time. To determine whether YAP plays a role in mediating therapy resistance to SMO inhibitors, therapy resistant tumors from Ptch;p53 medulloblastomas were generated. Tumor cells from spontaneous tumors that form in Ptch;p53 mice were isolated and injected into host mice and treated with LDE225, GDC-0449, or PBS. When resistant tumors emerged from the SMO inhibitor-treated groups, the tumors were harvested and analyzed for YAP expression. YAP RNA level was not significantly altered in resistant tumors (FIG. 6A); however, YAP protein level was significantly increased in the resistant tumors (FIG. 6B). Immunohistochemical analyses confirmed increased YAP expression in SMO inhibitor-resistant tumors (FIG. 6C) and in primary cells isolated from LDE-treated tumors (FIG. 6D). Together, these results indicate that YAP protein levels are increased in SMO inhibitor-resistant tumors and that this regulation appears to occur at a post-translational level.

Materials and Methods

Mice:

STOCK Gt(ROSA)26Sor<tm1(Smo/EYFP)Amc>/J (JAX#5130), FVB-Tg(GFAP-cre)25Mes/J (JAX#4600), STOCK Ptch1$^{tm1Mps}$/J (JAX#3081), NOD.Cg-Prkdc$^{scid}$Il2rg$^{tm1Wjl}$/SzJ (JAX#5557), STOCK Olig2tm2 (TVA,cre)Rth/J (JAX#11103), C57BL/6-Tg(Neurod2-Smo*A1)199Jols/J (JAX#8831), and B6.129S2-Trp53tm1Tyj/J (JAX#2101) were obtained from the Jackson Laboratory, Bar Harbor, Me. Floxed YAP1 strain was obtained from Dr. Fernando Camargo (Children's Hospital, Harvard Medical School, Boston, Mass.).

Patient Derived Xenograft (PDX) Models of Medulloblastoma:

Established PDX models were purchased from the Brain Tumor Resource Laboratory, Fred Hutchinson Cancer Research Center, Seattle, Wash. Frozen PDX cells were thawed and orthotopically injected into NOD scid gamma (NSG) (JAX#5557) mouse cerebella to propagate the models.

Histology, Immunohistochemistry, and Immunoblotting:

Standard protocols (see Chow et al., *Cancer Research* 2014, 74(17):4864-74) and the antibodies listed in Table 1 were used.

TABLE 1

| Antibody | Host | Catalog # |
|---|---|---|
| YAP | mouse | SC-101199 (Santa Cruz Biotechnology, Inc., Dallas, TX) |
| YAP | mouse | wh0010413m1 (Sigma Aldrich, St. Louis, MO) |
| YAP | rabbit | 14074 (Cell Signaling Technology, Danvers, MA) |
| YAP | rabbit | NB110-5838 (Novus Biologicals LLC, Littleton, CO) |
| KI67 | rabbit | AB15580 (Abcam plc, Cambridge, UK) |
| KI67 (human) | mouse | 14-5699 (Affymetrix/ebioscience, Inc., San Diego, CA) |
| PAX6 | rabbit | PRB-278P (Covance Inc., Princeton, NJ) |
| Actin-HRP | mouse | A00730 (GenScript Biotech Corp., Piscataway Township, NJ) |

Tissue Culture:

Primary cells from spontaneous mouse medulloblastoma (Ptch$^{+/+}$;p53$^{-/-}$ or FSMO;GFAPcre) and MED311 PDX model were isolated and cultured in serum-free stem cell medium (DMEM/F12, B27, pen/strep, bFGF9 10 nanograms per milliliter (ng/mL)), and EGF (20 ng/mL). Number of self-renewing stem cells in vitro were measured by plating single cells at a clonal density (<1 cell/μL) and counting spheres >100 μM 7 days later. To establish IC50 values, 3000 mouse medulloblastoma cells were plated in 96 wells and treated varying concentrations of verteporfin and new derivatives were synthesized, in triplicate, and viability was measured using Cell Titer Blue assay (Promega, Madison, Wis.) 3 days after drug treatment.

Tumor Slice Culture:

Fresh tumor tissues were dissected and cut into 250 micrometer (μm) thick slices and cultured at air-media interface in serum-free medium (DMEM/F12, B27, pen/strep) for 8-12 days. Tissue viability was measured by Cell Titer Blue assay (Promega, Madison, Wis.) at 2-4 days intervals. DMSO or drugs were added after each viability reading.

Statistical Analysis:

Prism 6 software (GraphPad Software, La Jolla, Calif.) was used to generate Kaplan-Meier survival curves and perform t-tests.

Example 2—Synthesis of Verteporfin and Verteporfin-Derivatives Verteporfin Synthesis Pangka et al., *Journal of Organic Chemistry*, 1986, 51(7), 1094-1100.

Brunner et al., *Monatshefte fuer Chemie*, 2002, 133(5), 679-705.

Common Intermediate for Target List 1

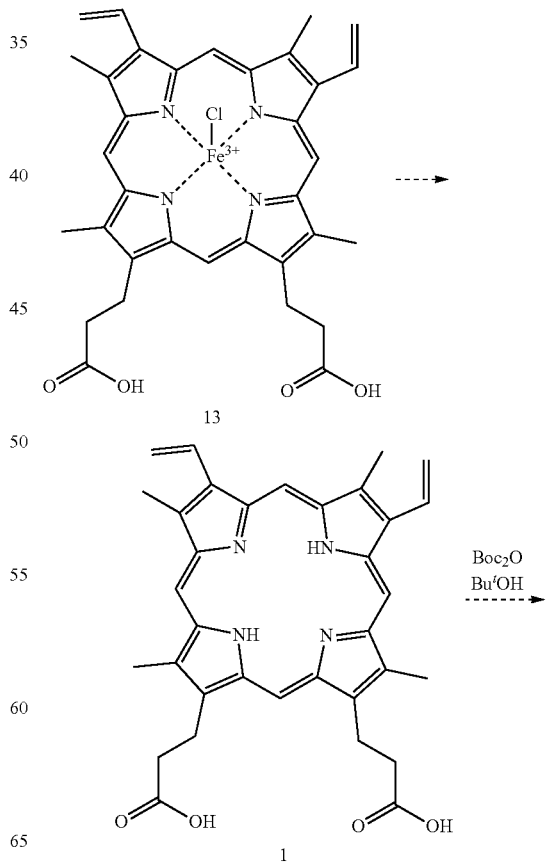

-continued
Desired Intermediate Column Separation to Remove Byproduct 4
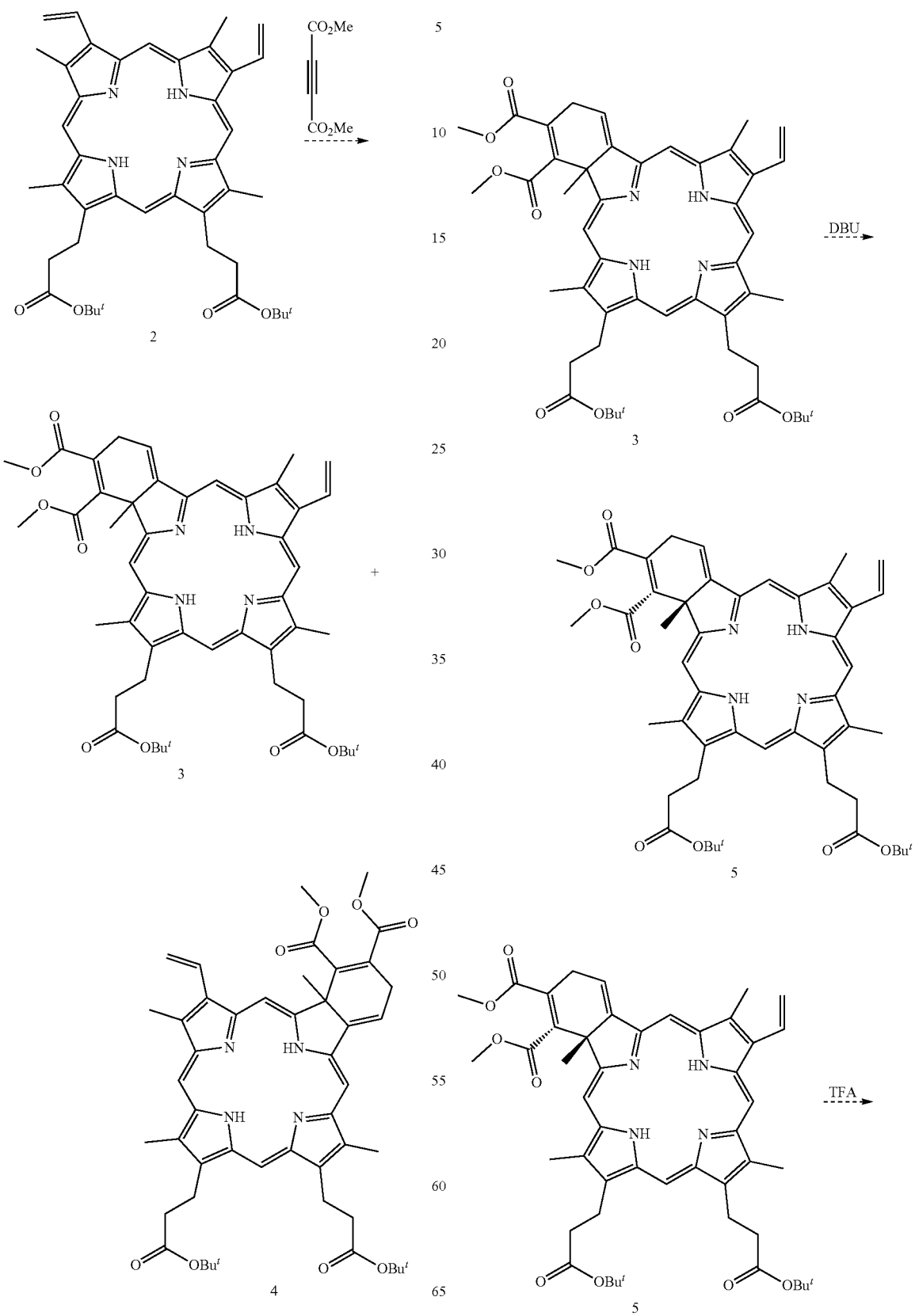

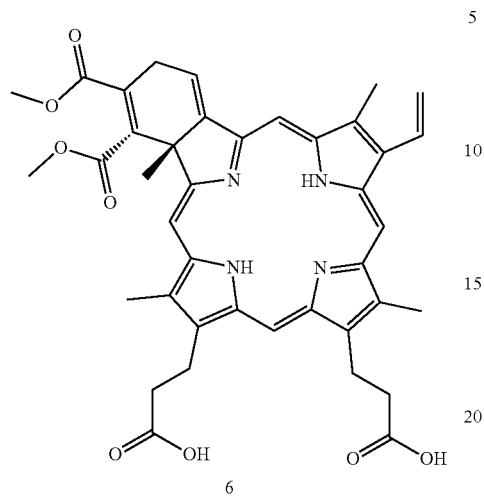
Verteporfin Analogues with Two Same Tails
Direct Coupling
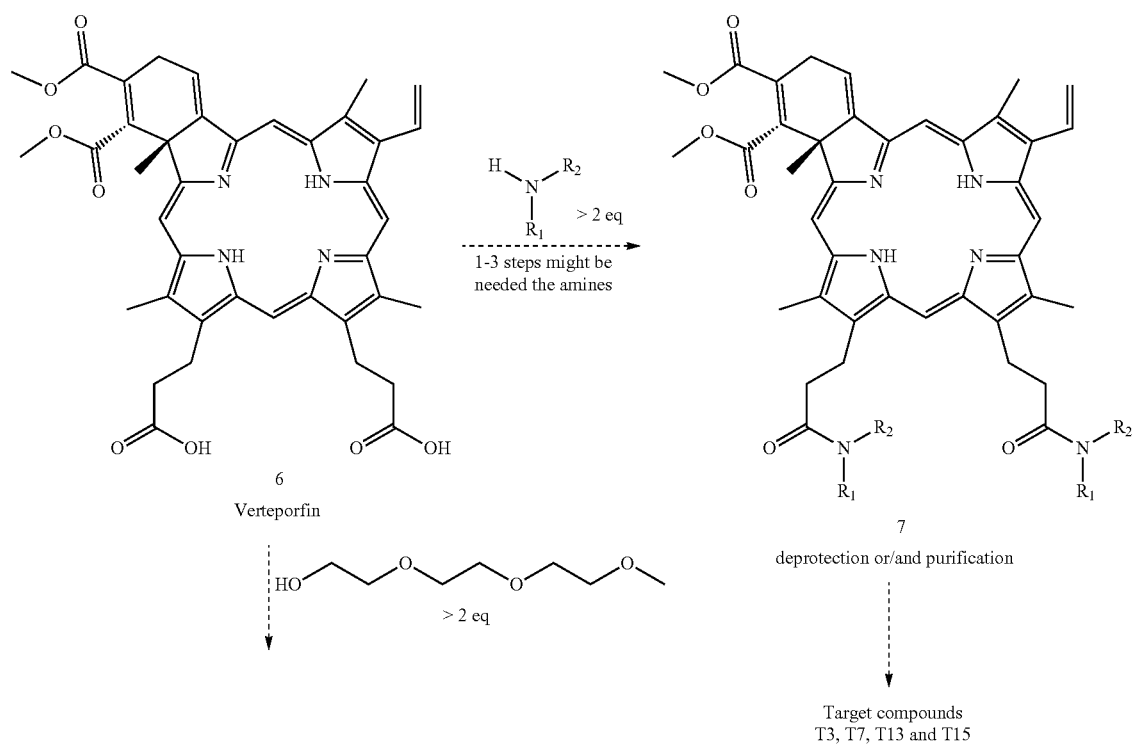

-continued
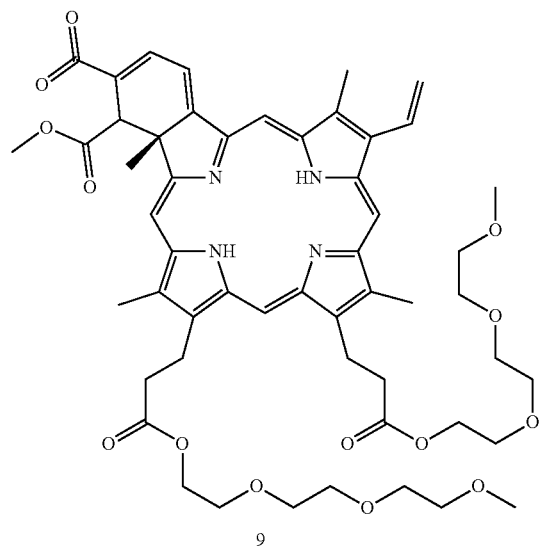
9
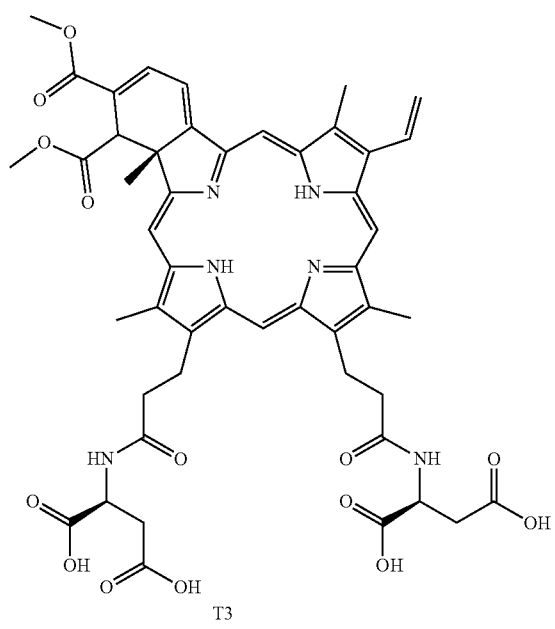
T3
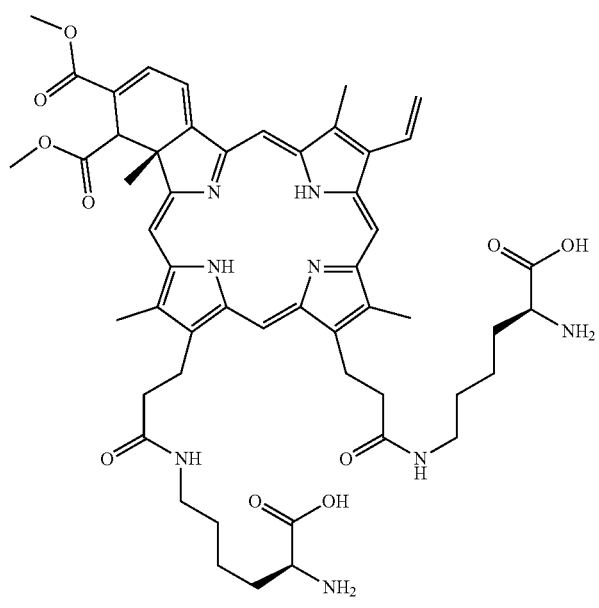
T7
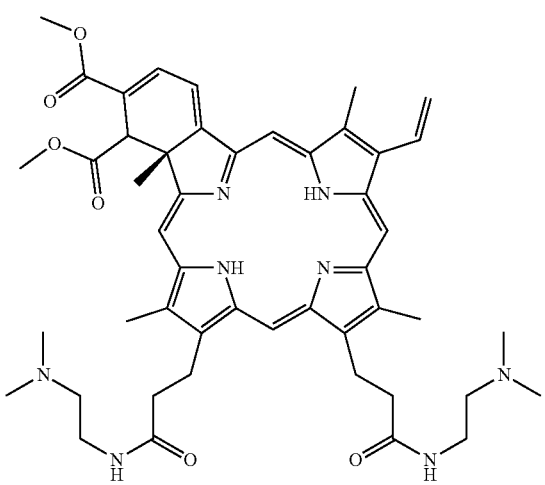
T13
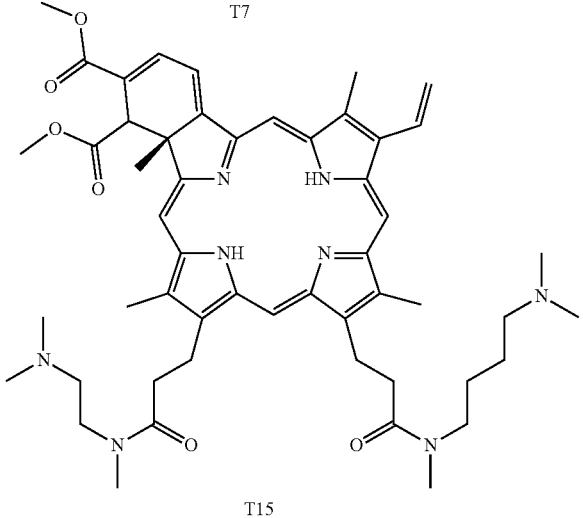
T15

Verteporfin Analogues with Two Same Tails
Via Active Ester
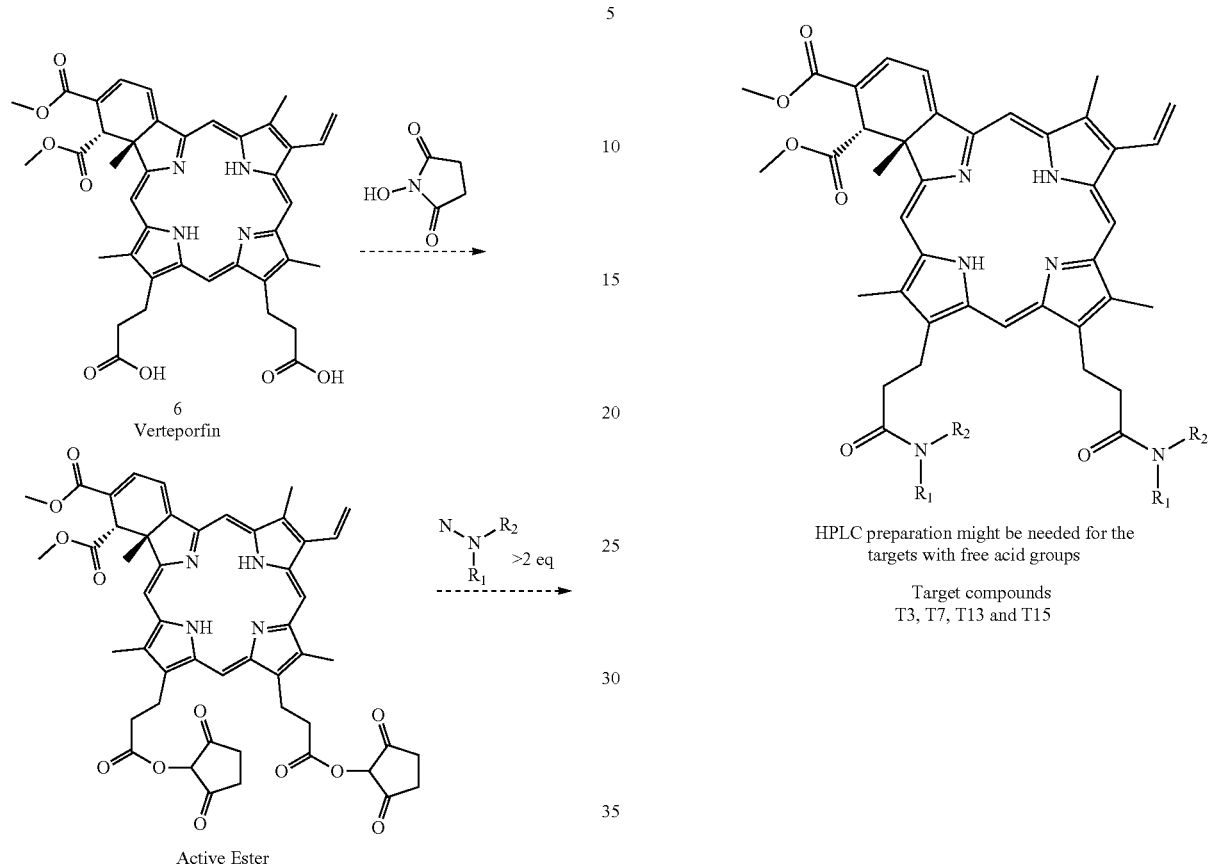
HPLC preparation might be needed for the targets with free acid groups
Target compounds
T3, T7, T13 and T15
Verteporfin Analogues with Two Different Tails
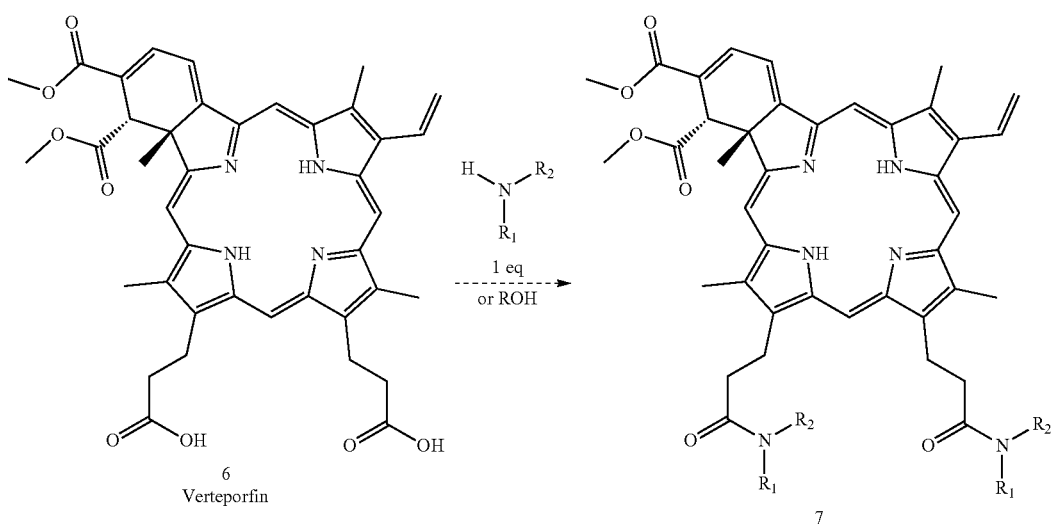

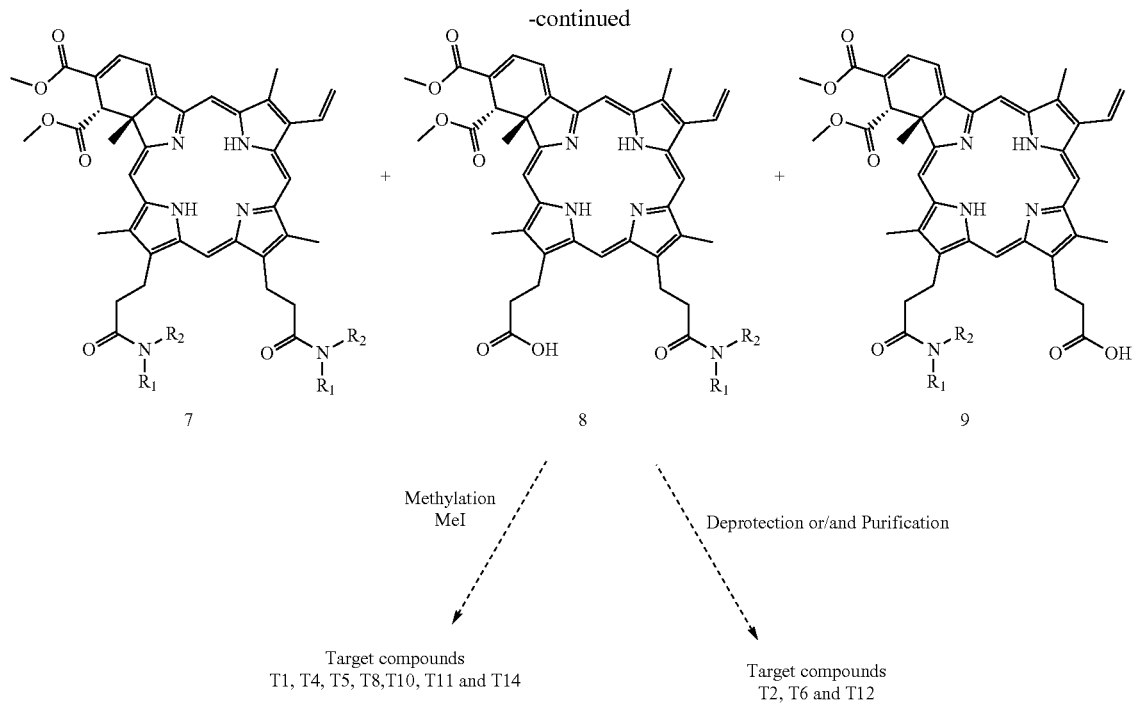

Methylation
MeI

Deprotection or/and Purification

Target compounds
T1, T4, T5, T8, T10, T11 and T14

Target compounds
T2, T6 and T12

References for Preparation of Verteporfin

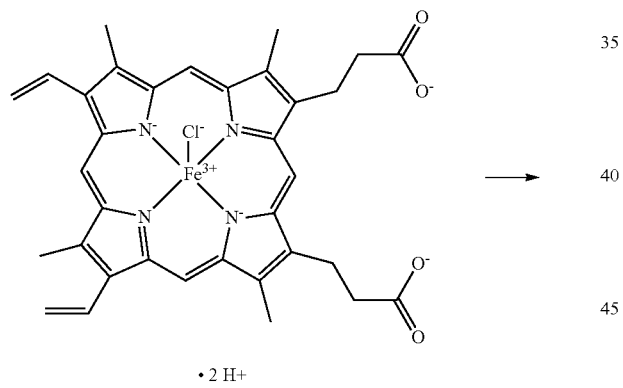

• 2 H+

93%

Overview
Steps/Stages
1.1 R: Zn, S: HCO$_2$H, 110° C.; 1 h, reflux; reflux→rt
1.2 R: NaOH, S: H$_2$O, pH 4-5

Notes
Reactants: 1, Reagents: 2, Solvents: 2, Steps: 1, Stages: 2, Most stages in any one step: 2

REFERENCES

Cui, Qiao-Li, et al., Synthesis and catalytic application of Co(II)-3,8-diethyl deuteroporphyrin dimethyl ester to the oxidation of cyclohexane, Gaodeng Xuexiao Huaxue Xuebao (Chemical Journal of Chinese Universities—Chinese Edition), 2011, 32(10), 2311-2315.

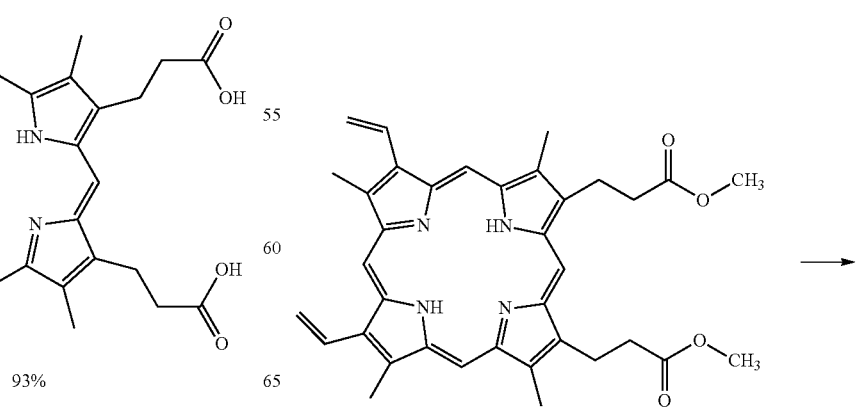

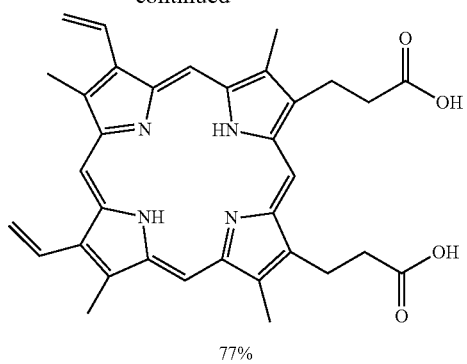

77%

Overview
Steps/Stages
1.1 R: KOH, S: MeOH, overnight, reflux; cooled
Notes
In the dark, Reactants: 1, Reagents: 1, Solvents: 1, Steps: 1, Stages: 1, Most stages in any one step: 1

REFERENCES

Crossley, Max, et al., Porphyrin linked metronidazole for treatment of gum disease caused by *Porphyromonas gingivalis*, PCT Int. Appl., WO/2006/005137

Experimental Procedure

Synthesis of 2,4-diethenyl-1,3,5,8-tetramethyl-porphine-6,7-dipropanoic acid-Protoporphyrin IX (PPIX) 3

Following the method of Smith, 1999 supra; 1976 supra, protoporphyrin IX dimethyl ester 26 (100 mg, 0.169 mmol) was dissolved in a solution of potassium hydroxide (3.02 g, 53.8 mmol) and methanol (35 ml) and heated at reflux under N2 gas in the dark overnight. Upon cooling, the solution was extracted with ethyl acetate. The combined ethyl acetate layers were extracted with hydrochloric acid (3 M, 2×50 ml). The aqueous layers were combined, adjusted to pH 4 with sodium hydroxide (3 M) and extracted into ethyl acetate (3×100 ml). The ethyl acetate layer was dried over anhydrous sodium sulfate, filtered and the solvent removed to yield pure protoporphyrin IX 3 (72.8 mg, 76.6%) as a purple-red solid, m.p. >300° C. with an identical $^1$H NMR spectrum to that quoted in the literature. $\lambda_{max}$ (CHCL$_3$/TFA)/nm 413 (log ε 5.24), 525 (3.25), 556 (3.99), 578 (3.75) and 600 (3.63); $^1$H NMR (200 MHz; CDCl$_3$; SiME$_4$) $\delta_H$ −3.33 (2H, s, inner NH), 3.19-3.26 (4H, t, 6.6 Hz, —CH$_2$CH$_2$CO$_2$H), 3.63 (3H, s, —CH$_3$), 3.67 (3H, s, —CH$_3$), 3.69 (3H, s, —CH$_3$), 3.72 (3H, s, —CH$_3$), 4.48 (4H, t, 5.1 Hz, —CH$_2$CH$_2$CO$_2$H). 6.30 (2H, dd, 17.8 Hz and 10.0 Hz, —CH=CH$_A$H$_B$), 6.47 (2H, dd, 11.4 Hz and 3.1 Hz, —CH=CH$_A$H$_B$), 8.09-8.27 (2H, m, —CH=CH$_A$H$_B$), 10.63 (1H, s, γ-H), 10.65 (1H, s, 6-H), 10.90 (1H, s, α-H), 10.92 (1H, s, (P3-H); m/z (MALDI-TOF) 563.4 [(M+H)$^+$ requires 563.7].

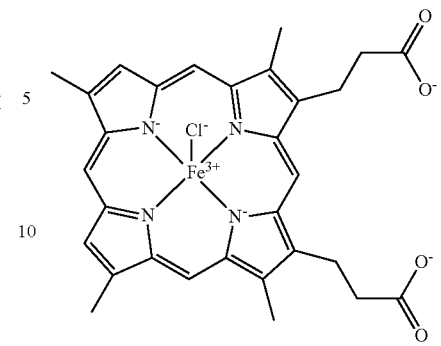

68%

Overview
Steps/Stages
1.1 R: H$_2$SO$_4$, 120 min, rt
1.2 R NH$_3$, S: H$_2$O, cooled, neutralized
Notes
Ultrasound, alternative reaction conditions gave lower yield, Reactants: 2, Reagents: 2, Solvents: 1, Steps: 1, Stages: 2, Most stages in any one step: 2

REFERENCES

Hu, Bingcheng et al., A facile synthesis of deuteroporphyrins derivatives under ultrasound irradiation, *Ultrasonics Sonochemistry*, 2010, 17(2), 288-291.
1. Single Step

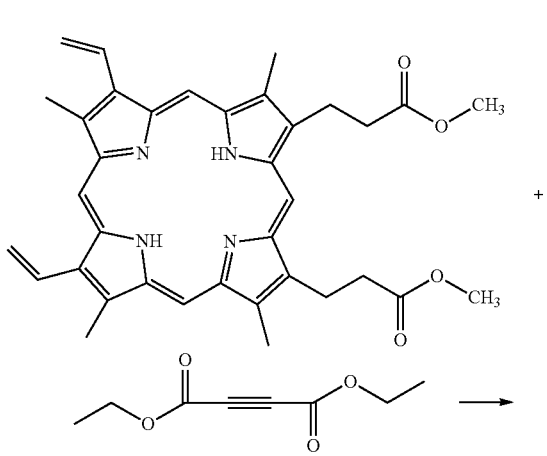

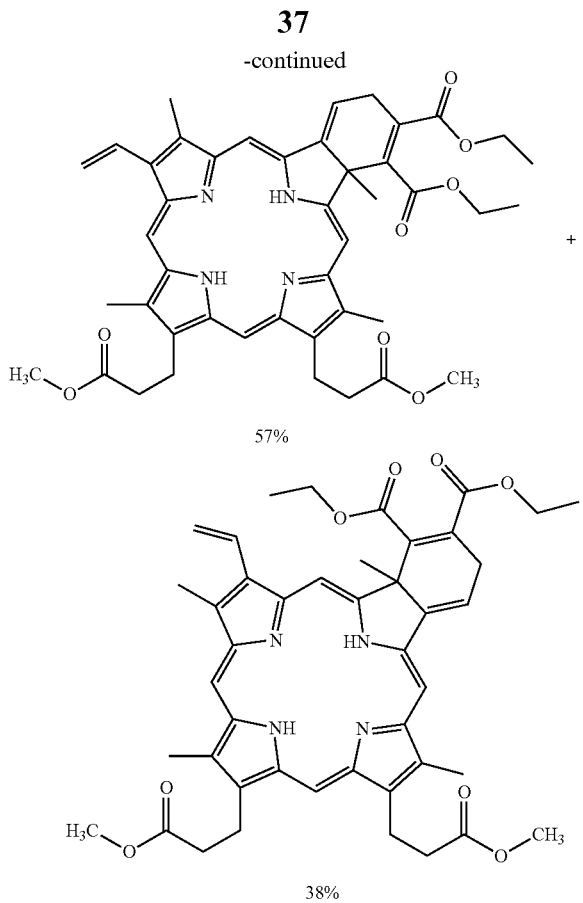

57%

38%

Overview
Steps/Stages
1.1 S: PhMe
Notes

Sepn. By column chromatog., regioselective, Reactants: 2, Solvents: 1, Steps: 1, Stages: 1, Most stages in any one step: 1

REFERENCES

Brunner et al., Benzoporphyrins and acetylene-substituted porphyrins as improved photosensitizers in the photodynamic tumor therapy with porphyrin platinum conjugates, *Monatshefte fuer Chemie*, 2002, 133(5), 679-705.

Experimental Procedure
Benzoporphyrin Isomers 1 and 2

($C_{44}H_{48}N_4O_8$) Under N2 protection, protoporphyrin dimethylester (1.00 g, 1.70 mmol) was dissolved in 100 cm³ of toluene, and diethyl acetylenedicarboxylate (1.06 g, 1.00 cm³, 6.30 mmol) was added. After 6 d of reflux the solvent was removed and the residue chromatographed on $SiO_2$ (120×2.5 cm) with $CH_2Cl_2$:$Et_2O$=50:1. First, the red zone of unreacted starting material eluted, followed by the product mixture 1/2 as a long brown-green zone. Separation of the isomers 1 and 2: 30 mg (0.04 mmol) of the isomer mixture 1/2 were dissolved in 10 cm³ of $CH_2Cl_2$ and chromatographed on $SiO_2$ (120×4 cm) with $CH_2Cl_2$:$Et_2O$=50:1. 2 eluted before 1. Isomers 1, green-black crystals, yield 11.4 mg, 38%; Isomers 2, dark-green crystals, yield 17 mg, 57%. 1:$C_{44}H_{48}N_4O_8$. m.p.: 111° C.; ¹H NMR ($CDCl_3$, 250 MHz): δ=9.85, 9.75, 9.39, 9.15, (4s, 4H, =CH), 8.18 (dd, $^3J_{cis}$=11.5, $^3J_{trans}$=17.8,1H, vinyl H-8), 7.41 (m, 1H, H-2⁴), 6.37 (m, 1H, vinyl H-8), 6.15 (m, 1H, vinyl H-8), 4.53 (q, $^3J$=7.2, 2H, $CH_2OOC$-2¹), 4.43-4.29 (m, 4H, =CCH_2, $CH_2OOC$-2²), 4.19 (t, $^3J$=7.6, 2H, =CCH_2), 4.02 (dd, $^3J$=22.2, $^2J$=6.7, 1H, H-23), 3.69-3.58 (dd, $^3J$=20.0, $^2J$=2.5, 1H, H-23), 3.67j, 3.66, 3.59, 3.50, 3.41 (5s, 15H, $CH_3$, $COOCH_3$), 3.21 (t, $^3J$=7.6, 2H, $CH_2COO$), 3.17 (t, $^3J$=7.6, 2H, $CH_2COO$), 2.11 (s, 3H, $CH_{3-2}$), 1.41, 1.05 (2t, $^3J$=7.2, 6 H, $CH_3CH_2OOC$-2², $CH_3CH_2OOC$-2¹) 2.75 (s, 2H, =NH) ppm 2: $C_{44}H_{48}N_4O_8$ m.p.: 208° C.; ¹H NMR ($CDCl_3$, 250 MHz): δ=9.82, 9.68, 9.32, 9.25 (4s, 4H, =CH), 8.17 (dd, $^3J_{trans}$=17.7, 1H, vinyl H-3), 7.40 (dd, $^3J$=6.7, $^2J$=2.1, 1H, H-7⁴), 6.33 (m, $^3J$=17.7, 1H, vinyl H-3), 6.15 (d, $^3J$=11.5, 1H, vinyl H-3), 4.53 (q, $^3J$=7.3, 2H, $CH_2OOC$-7¹), 4.42-4.36 (m, 2H, $CH_2OOC$-7²), 4.33 (t, $^3J$=7.8, 2H, =CCH_2), 4.19 (t, $^3J$=7.8, 2H, =CCH_2), 3.96 (dd, $^3J$=19.8, $^2J$=6.7, 1H, H-73, 3.74-3.54 (m, 1H, H-7³, 3.67, 3.65, 3.50 (int.2), 3.44 (4s, 15H, $CH_3$, $COOCH_3$), 0.21 (t, $^3J$=7.8, 2H, $CH_2OO$), 3.17 (t, $^3J$=7.8, 2H, $CH_2COO$), 2.11 (s, 3H, $CH_3$-7), 1.40. 0.99 (2t, $^3J$=7.1, 6 H, $CH_3CH_2COO$-7², $CH_3CH_2OOC$-7¹), −2.46 (s, 2H, =NH) ppm.

1. 5 Steps (Converging)

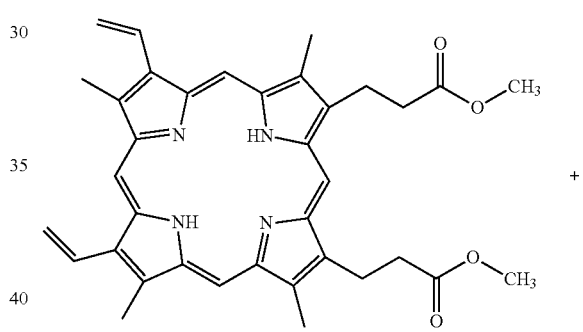

+

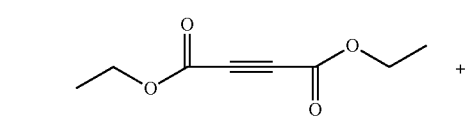

+

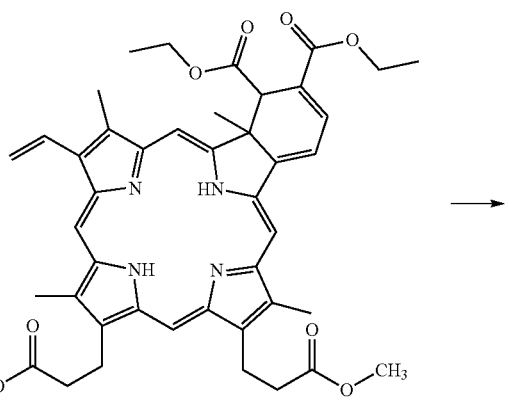

→

-continued

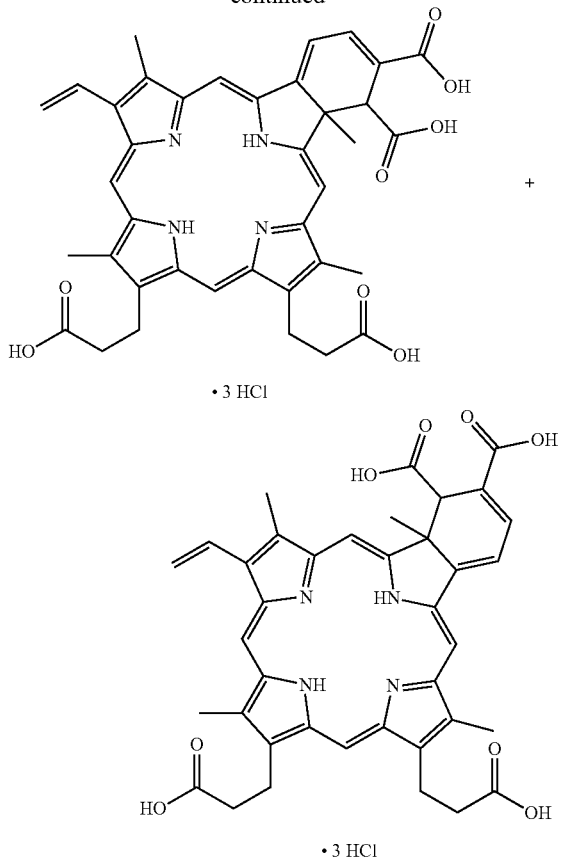

Overview
Steps/Stages
1.1 S: PhMe
2.1 R: DBU, S: CH$_2$Cl$_2$
2.2 R: HCl, S: H$_2$O
1.1 S: PhMe
2.1 R: DBU, S: CH$_2$Cl$_2$
2.2 R: HCl, S: H$_2$O
3.1 R: HCl, S: H$_2$O
Notes
Sepn. By column chromatog., regioselective, stereoselective, sepn. By column chromatog., regioselective, stereoselective, product depends on reaction time, Reactants: 3, Reagents: 2, Solvents: 3, Steps: 5, Stages: 7, Most stages in any one step: 2

REFERENCES

Brunner et al., Benzoporphyrins and acetylene-substituted porphyrins as improved photosensitizers in the photodynamic tumor therapy with porphyrin platinum conjugates, *Monatshefte fuer Chemie*, 2002, 133(5), 679-705.

Sequence 1
Step 1
Benzoporphyrin Isomers 1 and 2 (C$_{44}$H$_{48}$N$_4$O$_8$)

Under N2 protection, protoporphyrin dimethylester (1.00 g, 1.70 mmol) was dissolved in 100 cm$^3$ of toluene, and diethyl acetylenedicarboxylate (1.06 g, 1.00 cm$^3$, 6.30 mmol) was added. After 6 d of reflux the solvent was removed and the residue chromatographed on SiO$_2$ (120×2.5 cm) with CH$_2$Cl$_2$:Et$_2$O=50:1. First, the red zone of unreacted starting material eluted, followed by the product mixture 1/2 as a long brown-green zone. Separation of the isomers 1 and 2: 30 mg (0.04 mmol) of the isomer mixture 112 were dissolved in 10 cm$^3$ of CH$_2$Cl$_2$ and chromatographed on SiO$_2$ (120×4 cm) with CH$_2$Cl$_2$:Et$_2$O=50:1. 2 eluted before 1. Isomers 1, green-black crystals, yield 11.4 mg, 38%: Isomers 2, dark-green crystals, yield 17 mg, 57%. 1: C$_{44}$H$_{48}$N$_4$O$_8$. m.p.: 111° C.; $^1$H NMR (CDCl$_3$, 250 MHz): δ=9.85, 9.75, 9.39, 9.15 (4s, 4H, =CH), 8.18 (dd, $^3$J$_{cis}$=11.5, $^3$J$_{trans}$=17.8, 1H, vinyl H-8), 7.41 (m, 1H. H-2$^4$), 6.37 (m, 1H, vinyl H-8), 6.15 (m, 1H, vinyl H-8), 4.53 (q, $^3$J=7.2, 2H, CH$_2$OOC-2$^1$), 4.43-4.29 (m, 4H, =CCH$_2$, CH$_2$OOC-2$^2$). 4.19 (t, $^3$J=7.6. 2H, =CCH$_2$), 4.02 (dd, $^3$J=22.2, $^2$J=6.7, 1H, H-23), 3.69-3.58 (dd, $^3$J=20.0, $^2$J=2.5, 1H, H-23), 3.67, 3.66, 3.59, 3.50, 3.41 (5s, 15H, CH$_3$, COOCH$_3$), 3.21 (t, $^3$J=7.6, 2H, CH$_2$COO), 3.17 (t, $^3$J=7.6, 2H, CH$_2$COO), 2.11 (s, 3H, CH$_3$-2), 1.41, 1.05 (2t, $^3$J=7.2, 6 H, CH$_3$CH$_2$OOC-2$^2$, CH$_3$CH$_2$OOC-2$^1$), −2.57 (s, 2H, =NH) ppm. 2: C$_{44}$H$_{48}$N$_4$O$_8$. m.p.: 208° C.; $^1$H NMR (CDCl$_3$, 250 MHz): δ=9.82, 9.68, 9.32, 9.25 (4s, 4H, =CH), 8.17 (dd, $^3$J$_{cis}$=11.5, $^3$J$_{trans}$=17.7, 1 H, vinyl H-3), 7.40 (dd, $^3$J=6.7, $^2$J=2.1, 1H, H-7$^4$), 6.33 (m, $^3$J=17.7, 1H, vinyl H-3), 6.15 (d, $^3$J=11.5, 1H, vinyl H-3), 4.53 (q, $^3$J=7.3, 2H, CH$_2$OOC-7$^1$), 4.42-4.36 (m, 2H, CH$_2$OOC-7$^2$), 4.33 (t, $^3$J=7.8, 2H, =CCH$_2$), 4.19 (t, $^3$J=7.8, 2H, =CCH$_2$), 3.96 (dd, $^3$J=19.8, $^2$J=6.7, 1H, H-7$^3$, 3.74-3.54 (m, 1H, H-7$^3$, 3.67, 3.65, 3.50 (int. 2), 3.44 (4s, 15H, CH$_3$, COOCH$_3$), 0.21 (t, $^3$J=7.8, 2H, CH$_2$COO), 3.17 (t, $^3$J=7.8, 2H, CH$_2$COO.), 2.11 (s, 3H, CH$_3$-7), 1.40, 0.99 (2t, $^3$J=7.1, 6 H. CH$_3$CH$_2$OOC-7$^2$, CH$_3$CH$_2$COOC-7$^1$), −2.46 (s, 2H, =NH) ppm.

Step 2
General/Typical Procedure: Benzoporphyrin isomers 3 and 4 (C$_{44}$H$_{48}$N$_4$O$_8$) 100 mg (0.13 mmol) of 1 or 2 were reacted under N2 protection in 30 cm$^3$ CH$_2$Cl$_2$ with 5 cm$^3$ of 1,8-diazabicyclo[5.4.0]undec-7-ene (DBU) for 24 h at 20° C. The reaction mixture was poured onto 100 cm of 2 N HCl and extracted with 200 cm of CH$_2$Cl$_2$. The organic phase was washed three times with 200 cm of H$_2$O and once with 150 cm of brine. After drying over MgSO$_4$ the solvent was removed, and the residue was chromatographed on SiO$_2$ (120×5 cm) with CH$_2$Cl$_2$:MeOH=50:1. The product 3 or 4 eluted as an olive-green zone after a narrow red zone. Isomers 3, black-green crystals, yield 81 mg, 81%. C$_{44}$H$_{48}$N$_4$O$_8$. m.p.: >250° C.; IR (KBr): v=3300 (NH), 1740, 1720 (CO) cm$^{-1}$; PI-LISIMS (MNBA/CH$_2$Cl$_{12}$): m/z—761 (100) MH$^+$; UV/Vis (DMSO): λ$_{max}$ (log ε)=412 (4.70), 504 (3.71), 547 (3.70), 572 (3.83), 625 (3.58), 692 (4.05) nm; $^1$H NMR (CDCl$_3$, 250 MHz): δ=9.76, 9.69, 9.36, 9.17 (4s, 4H, =CH), 8.14 (dd, $^3$J$_{cis}$=11.7, $^3$J$_{trans}$=17.8, 1H, vinyl H-3), 7.82, 7.45 (2d, $^3$J=5.8, 2H, H-7$^3$, H-7$^4$), 6.37 (dd, $^3$J=17.7, $^2$J=1.5, 1 H, vinyl H-3), 6.15 (dd, $^3$J=11.9, $^2$J=1.5, 1H, vinyl H-3), 5.01 (s, 1H, H-7$^1$), 4.49-4.37 (m, 2H, CH$_3$CH$_2$OOC-7$^2$), 4.33, 4.19 (2t, 4H, $^3$J=7.7, =CCH$_2$), 3.67, 3.65, 3.64, 3.49, 3.42 (5s, 15H, CH$_3$, COOCH$_3$), 0.54-3.28 (m, 2H, CH$_3$CH$_2$OOC-7$^1$), 3.21, 3.17 (2t, $^3$J=7.7, 4H, CH$_2$COO), 1.80 (s, 3H, CH$_3$-7), 1.48, 0.29 (2t, $^3$J=7.1. 6 H, CH$_3$CH$_2$OOC-7$^2$, CH$_3$CH$_2$OOC-7$^1$), −2.28 (s, 2H, =NH) ppm.

Sequence 2
Step 1
Benzoporphyrin Isomers 1 and 2 (C$_{44}$H$_{48}$N$_4$O$_8$)

Under N2 protection, protoporphyrin dimethylester (1.00 g, 1.70 mmol) was dissolved in 100 cm$^3$ of toluene, and diethyl acetylenedicarboxylate (1.06 g, 1.00 cm$^3$, 6.30 mmol) was added. After 6 d of reflux the solvent was removed and the residue chromatographed on SiO$_2$ (120×2.5 cm) with CH$_2$Cl$_2$:Et$_2$O=50:1. First, the red zone of unreacted starting material eluted, followed by the product mixture ½ as a long brown-green zone. Separation of the isomers 1 and 2: 30 mg (0.04 mmol) of the isomer mixture ½ were dissolved in 10 cm$^3$ of $CH_2Cl_2$ and chromatographed on $SiO_2$ (120×4 cm) with $CH_2Cl_2$:$Et_2O$=50:1. 2 eluted before 1. Isomers 1, green-black crystals, yield 11.4 mg, 38%; Isomers 2, dark-green crystals, yield 17 mg, 57%. 1: $C_{44}H_{48}N_4O_8$. m.p: 111° C.; $^1$H NMR (CDCl$_3$, 250 MHz): δ=9.85, 9.75, 9.39, 9.15 (4s, 4H, =CH), 8.18 (dd. $^3J_{cis}$=11.5, $^3J_{trans}$=17.8, 1H, vinyl H-8). 7.41 (m, 1H, H-2$^4$), 6.37 (m, 1H, vinyl H-8), 6.15 (m, 1H, vinyl H-8), 4.53 (q, $_3$J=7.2, 2H, $CH_2OOC$-2$^1$), 4.43-4.29 (m, 4H, =CCH$_2$, $CH_2OOC$-2$^2$). 4.19 (t, $^3$J=7.6, 2H, =CCH$_2$), 4.02 (dd, $^3$J=22.2, $^2$J=6.7, 1H, H-23), 3.69-3.58 (dd, $^3$J=20.0, $^2$J=2.5, 1H, H-23), 3.67, 3.66, 3.59, 3.50, 3.41 (5s, 15H, CH$_3$, COOCH$_3$), 3.21 (t, $^3$J=7.6, 2H, CH$_2$COO), 3.17 (t, $^3$J=7.6, 2H, CH$_2$COO), 2.11 (s, 3H, CH$_3$-2), 1.41, 1.05 (2t, $^3$J=7.2, 6 H, CH$_3$CH$_2$OOC-2$^2$, CH$_3$CH$_2$OOC-2$^1$), −2.57 (s, 2H, =NH) ppm. 2: $C_{44}H_{48}N_4O_8$. m.p.: 208° C.; $^1$H NMR (CDCl$_3$, 250 MHz): δ=9.82, 9.68, 9.32, 9.25 (4s, 4H, =CH). 8.17 (dd, $^3J_{cis}$=11.5, $^3J_{trans}$=17.7, 1 H, vinyl H-3), 7.40 (dd. $^3$J=6.7, $^2$J=2.1, 1H, H-7$^4$), 6.33 (m. $^3$J=17.7, 1H, vinyl H-3), 6.15 (d, $^3$J=11.5. 1H, vinyl H-3), 4.53 (q, $^3$J=7.3, 2H, CH$_2$OOC-7$^1$), 4.42-4.36 (m, 2H, CH$_2$OOC-7$^2$), 4.33 (t, $^3$J=7.8, 2H, =CCH$_2$), 4.19 (t, $^3$J=7,8, 2H, =CCH$_2$), 3.96 (dd, $^3$J=19.8, $^2$J=6.7, 1H, H-7$^3$, 3.74-3.54 (m, 1H, H-7$^3$, 3.67, 3.65, 3.50 (int. 2), 3.44 (4s. 15H, CH$_3$, COOCH$_3$), 0.21 (t, $^3$J=7.8, 2H, CH$_2$COO), 3.17 (t, $^3$J=7.8, 2H, CH$_2$COO), 2.11 (s, 3H, CH$_3$-7), 1.40, 0.99 (2t, $^3$J=7.1, 6 H, CH$_3$CH$_2$OOC-7$^2$, CH$_3$CH$_2$OOC-7$^1$), −2.46 (s, 2H, =NH) ppm.

Step 2

Benzoporphyrin Isomers 3 and 4 ($C_{44}H_{48}N_4O_8$)

100 mg (0.13 mmol) of 1 or 2 were reacted under N2 protection in 30 cm$^3$ CH$_2$Cl$_2$ with 5 cm$^3$ of 1,8-diazabicyclo[5.1.0]undec-7-ene (DBU) for 24 h at 20° C. The reaction mixture was poured onto 100 cm of 2 NHCl and extracted with 200 cm of CH$_2$Cl$_2$. The organic phase was washed three times with 200 cm of H$_2$O and once with 150 cm of brine. After drying over MgSO$_4$ the solvent was removed, and the residue was chromatographed on SiO$_2$ (120×5 cm) with CH$_2$Cl$_2$:MeOH=50:1. The product 3 or 4 eluted as an olive-green zone after a narrow red zone. Isomers 3, black-green crystals, yield 75 mg, 75%. $C_{44}H_{48}N_4O_8$. m.p.: 180° C.; IR (KBr): v=3300 (NH), 1740, 1710 (CO) cm$^{-1}$; $^1$H NMR (CDCl$_3$, 250 MHz): δ=9.78, 9.63, 9.36. 8.97 (4s, 4H, =CH), 8.16 (dd, $^3J_{cis}$=1.9, $^3J_{trans}$=17.7, 1H, vinyl H-8}, 7.77, 7.40 (2d, $^3$J=5.8, 2H, H-2$^3$, H-2$^4$), 6.31 (dd, $^3$J=17.7, $^2$J=1.5, 1H, vinyl H-8), 6.13 (dd, $^3$J=11.9, $^2$J=1.5, 1H, vinyl H-8), 4.99 (s, 1H, H-21), 4.50-4.35 (m, 2H, CH$_3$CH$_2$OOC-2$^2$), 4.30, 4.15 (2t, 4H, $^3$J=7.7, =CCH$_2$), 3.66, 3.65, 3.54, 3.48, 3.38 (5s, 15H, CH$_3$, COOCH$_3$), 3.51-3.27 (m, 2H, CH$_3$CH$_2$OOC-2$^1$), 3.20, 3.15 (2t, $^3$J=7.7, 4H, CH$_2$COO), 1.82, (s, 3H, CH$_3$-2), 1.47, 0.31 (2t, $^3$J=7.0, 6 H, CH$_3$CH$_2$OOC-2$^2$, CH$_3$CH$_2$OOC-21), −2.28 (s, 2H, =NH) ppm.

Step 3

Benzoporphyrin tetraacid isomer mixture ⅞ ($C_{38}H_{36}N_4O_3$.3HCl) 121 mg (0.16 mmol) of ¾ were stirred in 100 cm$^3$ of 25% HCl for 20 h at 80° C. Then, the solvent was removed by freeze-drying under high vacuum. Isomers 7; Isomers 6. Yield quantitative. ⅞: $C_{38}H_{38}N_4O_8$.3HCl. m.p.: >250° C.; IR (KBr): v=1705, 1675 (CO) cm$^{-1}$; PI-LISIMS (glycerol/DMSO): m/z—679 (100%) MH$^+$; UV/Vis (DMSO):

λ$_{max}$(log ε)=407 (4.25), 502 (4.01), 547 (3.99), 572 (3.99), 625 (3.96), 68 8 (3.95) nm.

Different Tails

1. Single Step

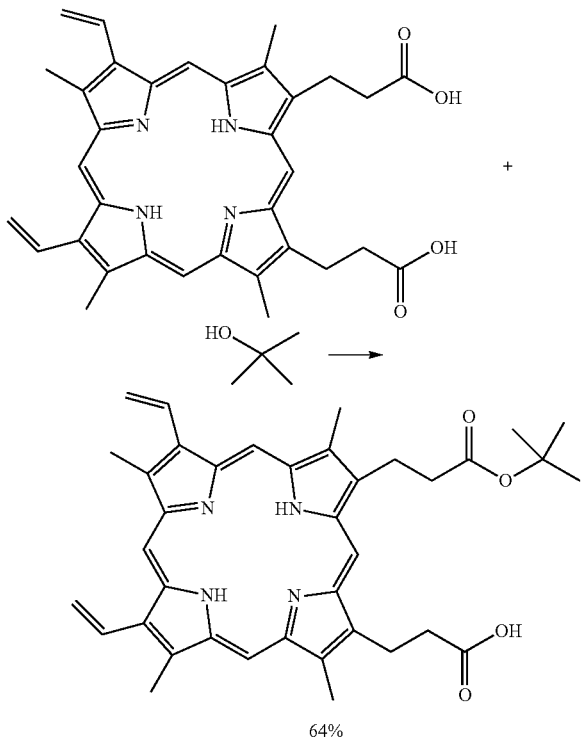

Overview

Steps/Stages 1.1 R:4-DMAP, R: (Boc)$_2$O, S: C$_5$H$_5$N 1.2 S: t-BuOH, rt

Notes

Regioisomeric mixture formed, Reactants: 2, Reagents: 2, Solvents: 2, Steps: 1, Stages: 2, Most stages in any one step: 2

REFERENCES

Kitagishi et al., Self-assembly of one- and two-dimensional hemoprotein systems by polymerization through heme-heme pocket interactions, *Angewandte Chemie, International Edition*, 2009, 48(7), 1271-1274.

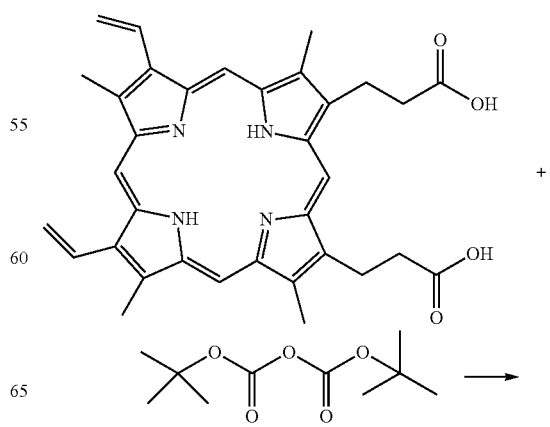

-continued

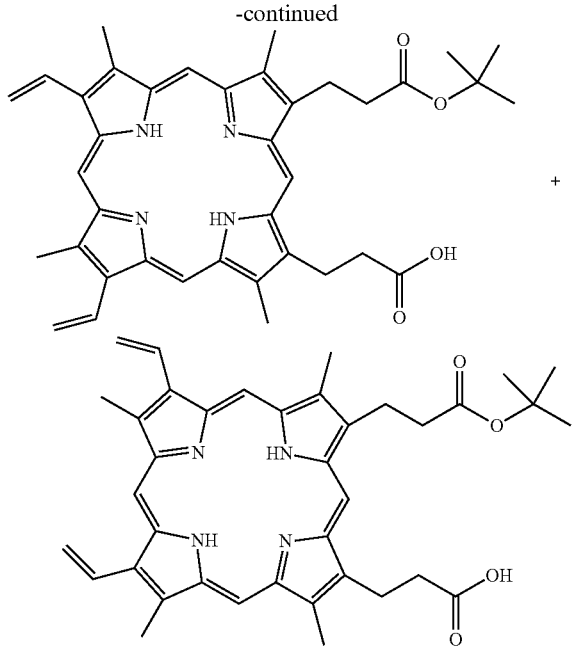

Steps/Stages 1.1 R: 4-DMAP, S: C$_5$H$_5$N, rt; 6 h, rt 1.2 R:
    t-BuOH, 1 h, rt Notes 63% Combined yield, in the dark in stage 1, slow addition of Boc2O, Reactants: 2, Reagents: 2, Solvents: 1, Steps: 1, Stages: 2, Most stages in any one step: 2

REFERENCES

Wan et al., Fabrication of a Thermoresponsive Biohybrid Double Hydrophilic Block Copolymer by a Cofactor Reconstitution Approach, *Macromolecular Rapid Communications,* 2010, 31(23), 2070-2076.

3. Single Step

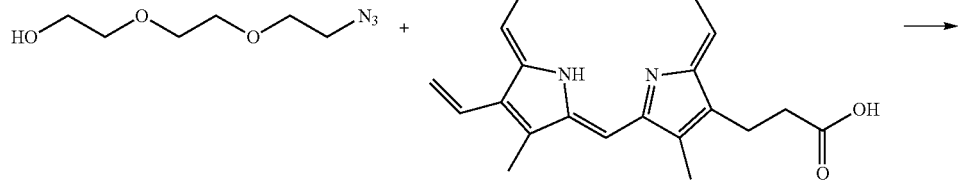

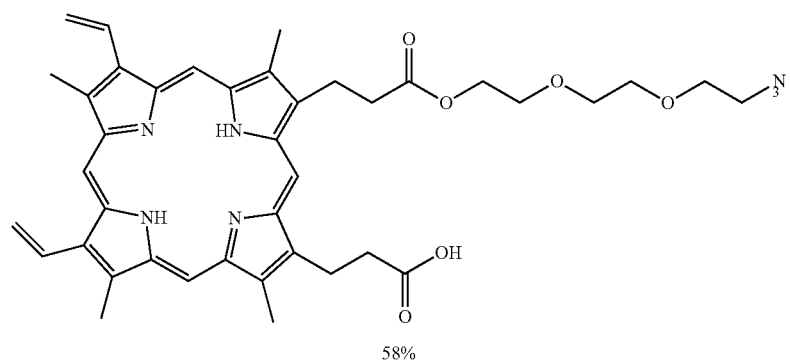

58%

Overview
Steps/Stages
1.1 R:4-DMAP, R: EtN=C=N(CH$_2$)$_3$NMe$_2$.HCl, S: DMF, 0° C.→rt; overnight, rt
Notes
Nonseparable mixture of regioisomers, Reactants: 2, Reagents: 2, Solvents: 1, Steps: 1, Stages: 1, Most stages in any one step: 1

REFERENCES

Chrominski et al., Protoporphyrin IX/Cobyrinate Derived Hybrids—Novel Activators of Soluble Guanylyl Cyclase, *European Journal of Organic Chemistry*, 2013, 2013(8), 1530-1537.

Overview
Steps/Stages
1.1 R: Et$_3$N, R: (PhO)$_2$P(=O)N$_3$, S: DMF, <rt; 4 h, rt; 2 h, rt
Notes
In the dark, Reactants: 3, Reagents: 2, Solvents: 1, Steps: 1, Stages: 1, Most stages in any one step: 1

REFERENCES

Kitagishi et al., Supramolecular Hemoprotein Linear Assembly by Successive Interprotein Heme-Heme Pocket Interactions, *Journal of the American Chemical Society*, 2007, 129(34), 10326-10327.

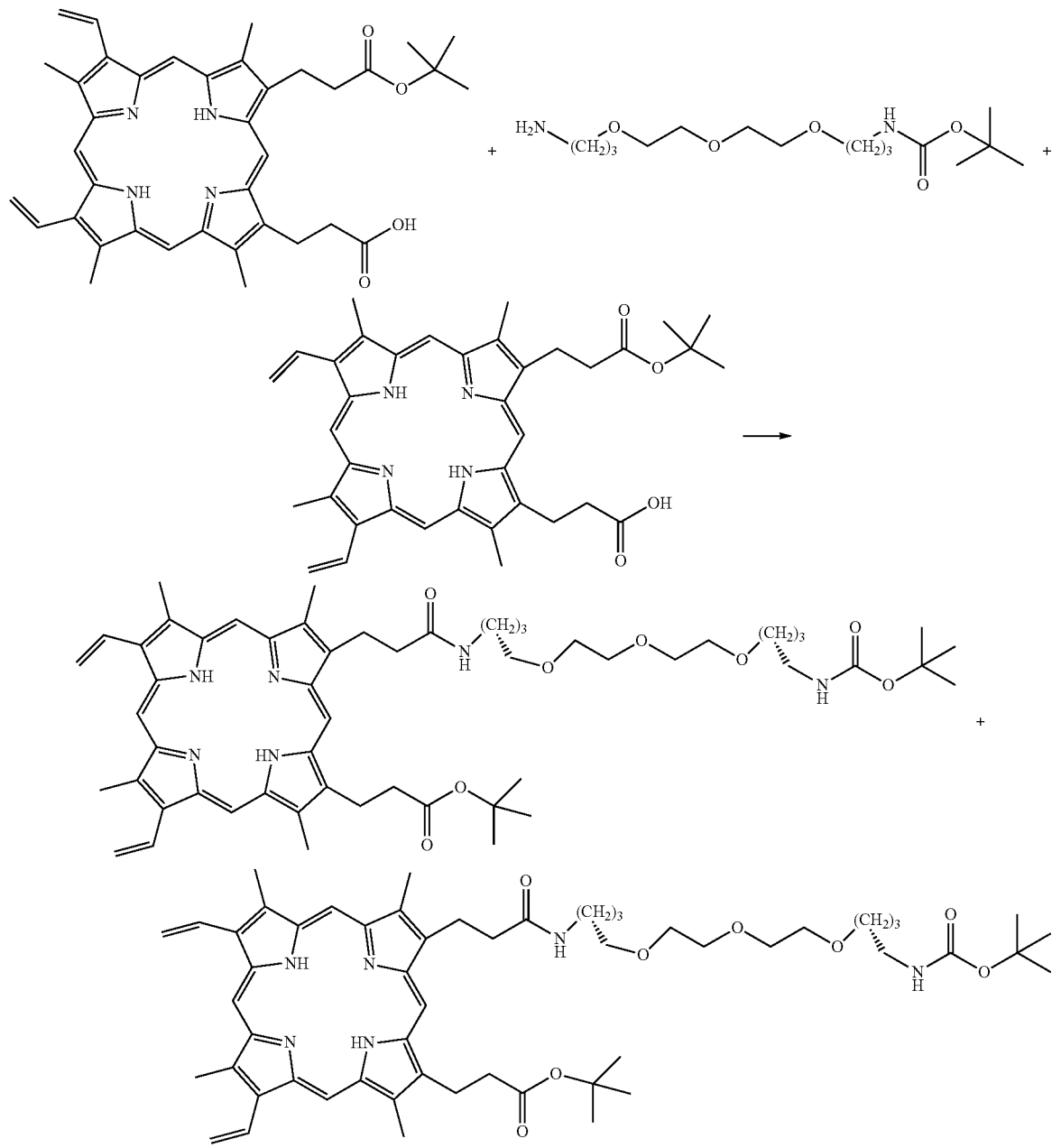

Experimental Procedure

General/Typical Procedure: 3b: In a 50-mL round bottom flask under a N2 atmosphere, the protoporphyrin IX monotbutyl ester (255 mg, $4.1 \times 10^{-4}$ mol) and N-Boc-1,2-bis(2-aminoethoxy)ethane (208 mg, $8.4 \times 10^{-4}$ mol) were dissolved in 25 mL of DMF. The solution was cooled in an ice bath under N2 atmosphere. To the solution were added DPPA. (290 mg, $1.1 \times 10^{-3}$ mol) in 1 mL of DMF and $Et_3N$ (170 mg, $1.7 \times 10^{0.3}$ mol) in 1 mL of DMF. The solution was stirred for 4 h at room temperature in the dark, and the same amount of DPPA and of $Et_3N$ was further added to the solution. After the solution was stirred for 2 h at room temperature, the solvent was evaporated. The residue was passed through a short column chromatography ($SiO_2$, $CHCl_3$/acetone=5/1, v/v). After the eluent was collected and concentrated, the residue was dissolved in a minimum amount of $CHCl_3$ and precipitated by the addition of hexane. The dark-purple precipitate was collected dried under vacuum gave the product yield 218 mg, 63%. Product, yield 49%. $^1$H-NMR (270 MHz, pyridine-ds) δ 10.34 (4s, 1H) 10.21 (x, 0.5H) 10.17 (s. 0.5H) 10.17 (s, 1H) 10.14 (s, 1H) 10.03 (s, 0.5H) 9.95 (s, 0.5H) 8.39-8.25 (m, 2H) 6.41-6.14 (m, 4H) 4.60-4.38 (m, 4H) 3.62-3.45 (m, 16H) 3.34-3.15 (m, 12H) 3.06 (m, 2H) 2.76 (m, 2H) 2.61 (m, 2H) 2.44 (m, 2H) 1.74 (m, 2H) 1.49 (s, 9H) 1.43 (s, 9H) 1.39 (m, 2H) −3.80 (s, 2H); ESI-TOF-MS (positive mode) m/z 921.83 (M+H)$^+$, calcd for $C_{53}H_{72}N_6O_8$ 922.18; UV-vis ($CHCl_3$) $\lambda_{max}$/nm(absorbance) 630 (0.032) 576 (0.042) 540 (0.072) 506 (0.088) 408 (1.05).

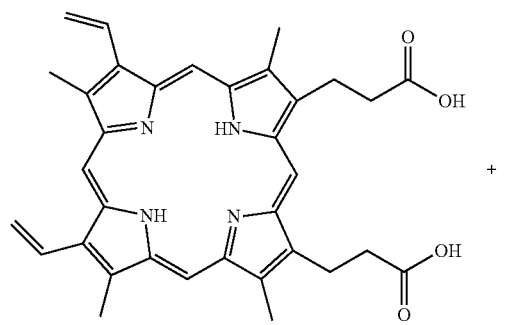

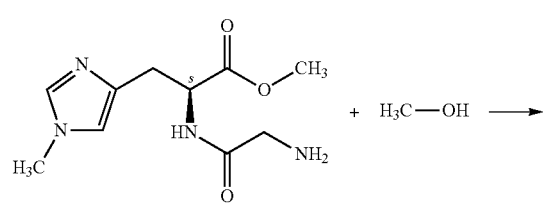

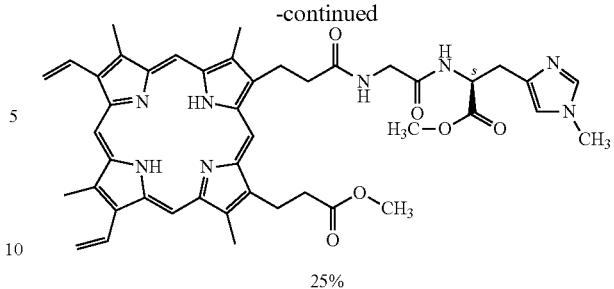

25%

Overview
Steps/Stages
1.1 R: C5H5N, S: C5H5N, 10 min, rt
1.2 R: BOP reagent, 10 min, rt
1.3 S: DMF, rt; 2.5 h, rt
1.4 18 h, rt
Notes
In the dark in stage 3, Reactants: 2, Reagents: 2, Solvents: 2, Steps: 1, Stages: 4, Most stages in any one step: 4

REFERENCES

Tsuchida et al., Preparation of 1-methylhistidine-substituted porphyrins and their complexes, and use of the complexes for artificial oxygen carriers, Jpn. Kokai Tokkyo Koho, 2008031103, 14 Feb. 2008.

Experimental Procedure

Example 7 Protoporphyrin IX (400 mg, 0.71 mmol) was dissolved in 40 mL pyridine and it was stirred at room temperature for 10 minutes. Then BOP (840 mg, 1.9 mmol) was added and stirred for an additional 10 minutes. Glycyl-L-(1-methyl)histidinemethyl ester (136 mg, 0.57 mmol) was dissolved in 15 mL of DMF, it was slowly added dropwise to the reaction solution using a dropping funnel, stirred in the dark for 2.5 hours at room temperature, 5 mL methanol was added, and stirring was continued for further 18 hours. The resulting reaction solution was added dropwise to 2 L ice water, centrifuged (7000 g, 30 minutes), and the precipitate was filtered through G4 glass filter, then it was dissolved in chloroform/methanol solution. After the removal of solvent under reduced pressure, the fractionations were purified by silica gel column (chloroform/methanol: 10/1 (v/v), and the resulting component was dried under vacuum. 142 mg of 3,18-divinyl-8-(3-methoxycarbonyl)ethyl-12-(2-((O-methyl)(1-methyl)histidyl)glycineamide ethyl)-2,7,13,17-tetramethyl-porphrin (25% yield) was obtained. Thin-layer chromatography (chloroform/methanol=10/1 (v/v)): Rf=0.50 (monospot). Infrared absorption spectrum (cm$^{-1}$): 1636 ($v_{c=o}$ (amide)), 1725 ($v_{c=o}$ (ester)). Visible absorption spectrum (chloroform): $\lambda_{max}$=627,577,541,505,4 05 nm. FAB-MS spectrum: 801 ([M+H] $^1$H-NMR spectrum (d6-DMSO, reference TMS): δ (ppm)=−4.6 (s, 2H Inner-NH), 2.7-2.9 (m, 2H, imidazole-$CH_2$—), 3.0-3.5 (m, 20H, por-$CH_3$, —$CH_2$—$CH_2$—CO—NH—), 3.6 (s, 3H, —$OCH_3$), 3.7 (m, 3H, histidine-$CH_3$), 4.0-4.3 (d, 4H, por-$CH_2$—), 4.3-4.5 (m, 1H, α-CH), 6.0-6.4 (m, 4H, vinyl=$CH_2$), 7.4 (s, 1H, histidine), 8.0-8.3 (m, 5H, vinyl-CH=, histidine), 9.8-10 (m, 4H, mesa-H)

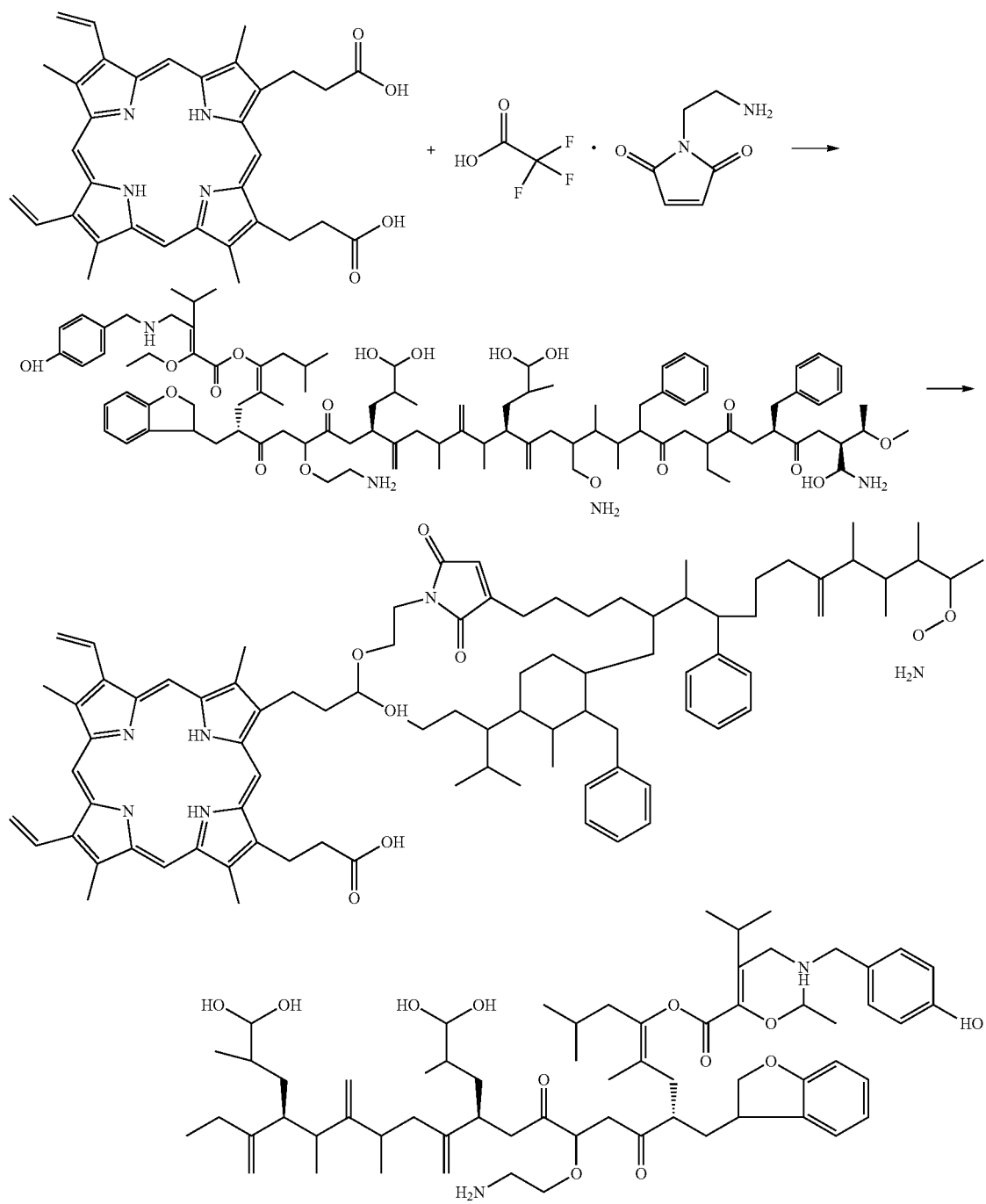

Overview

Steps/Stages 1.1 R: N-Hydroxysuccinimide, S: DMF, 10 min, 0° C.
1.2 R: EtN=C=N(CH$_2$)$_3$NMe$_2$.HCl, 0° C.; 4 h, rt
1.3 5 h, rt
2.1 R: EtN(Pr-l)$_2$, S: DMSO, overnight, rt Notes 1) 43% combined yield of regioisomers, Reactants: 3, Reagents: 3, Solvents: 2, Steps: 2, Stages: 4, Most stages in any one step: 3

REFERENCES

Liu et al., Lipopolysaccharide Neutralizing Peptide-Porphyrin Conjugates for Effective Photoinactivation and Intracellular Imaging of Gram-Negative Bacteria Strains, *Bioconjugate Chemistry*, 2012, 23(8), 1639-1647.

Experimental Procedure

Step 1

Monomeric PpIX-Maleimide Derivative 4.

Protoporphyrin IX (PpIX) (50 mg, 0.09 mmol) and N-hydroxysuccinimide (HOSu) (9.2 mg, 0.08 mmol, 0.9 equiv) was dissolved in 8 mL of dimethyl-formamide (DMF) at 0°

C. and stirred for 10 min before the addition of 1-ethyl-3-(3-dimethyl-aminopropyl) carbodiimide hydrochloride (EDC.HCl) (20.4 mg, 0.117 mmol, 1.3 equiv). The reaction mixture was stirred at room temperature for 4 h. Compound 3 (20 mg, 0.08 mmol, 0.9 equiv) was then added and the system was left to stir for a further 5 h at room temperature. The compound was purified by flash chromatography with eluent methanol/DCM=1:20 to give a red solid product as mixture of two regioisomers. Yield (26.2 mg, 43%). $^1$H NMR (400 MHz, DMSO-d6): δ 2.92 (2H, t, J=7.6 Hz), 3.16-3.20 (4H, m), 3.44 (2H, t, J=5.8 Hz), 3.61 (6H, m), 3.71 (6H, m), 4.27 (2H, t, J=7.6 Hz), 4.35 (2H, t, J=7.2 Hz), 6.23 (2H, d, J=11.2 Hz), 6.47 (2H, dd, $J_1$=18.0 Hz, $J_2$=2.0 Hz), 6.86 (2H, s), 8.0.6 (1H, s), 8.48 (2H, dd, $J_1$=17.6 Hz, $J_2$=11.6 Hz), 10.20-10.25 (4H, m). $C_{40}J_{40}N_6O_5$, ESI-MS: ml z 684.31 (calcd); 685.48 [M+H]$^+$, 1368.80 [2M+H]$^+$ (found).

Step 2

Monomeric PpIX-Peptide Conjugate 6.

Compound 4 (1.1 mg, 1.6 μmol) and peptide YI13WF (2.8 mg, 1.6 μmol) in 200 μL of dimethylsulfoxide (DMSO) were added with 5 μL DMSO solution containing 10% diisopropylethylamine (DIPEA). The mixture was allowed to stir at room temperature overnight and then was added to 10 mL diethyl ether to give a red precipitate. This crude solid was purified by reverse-phase high performance liquid chromatography (HPLC) with eluting system consisting of A (water with 0.1% TFA) and B (acetonitrile with 0.1% TFA) under a linear gradient, monitored by UV absorbance et 280 and 400 nm. The linear gradient stretched over 43 min trout t=2 min at 7% solution A and 30% solution B to t=45 min at 20% solution A and 80% solution B. The reaction yielded a deep red solid monomeric PpIX-peptide conjugate 6 after lyophilization. Yield (2.3 mg 56%). $^1$H NMR (400 MHz, DMSO-d6): δ 0.66-0.80 (m), 0.96 (br s), 1.12 (s), 1.21-1.71 (overlapped), 1.8.4-1.92(m), 2.25-2.36 (m), 2.65-2.75 (overlapped), 2.76-2.92 (m), 2.81-3.15 (m), 3.57 (dd, $J_1$=10.6 Hz, $J_2$=7.2 Hz), 3.69-3.71 (m), 3.89-3.96 (m), 4.12-4.30 (m), 4.47-4.55 (m), 6.15-6.19 (m), 6.41 (d, J=17.6 Hz), 6.56 (d, J=8.4 Hz), 6.87-6.98 (m), 7.00-7.20 (m), 7.24 (d, J=8.0 Hz), 7.52-7.63 (m), 7.68-7.75 (br s), 7.82-7.94 (br s), 7.96-8.21 (m), 8.42-8.52 (m), 9.15 (br s), 10.19 (s), 10.23 (s), 10.25 (s), 10.32 (s), 10.70 (s). $C_{128}H_{175}N_{29}O_{20}S$, ESI-MS: m/z 2471.33 (calcd); m/2z, 1236.53, m/3z 825.11, m/4z 619.18, m/5z, 495.69 (found).

Reduction

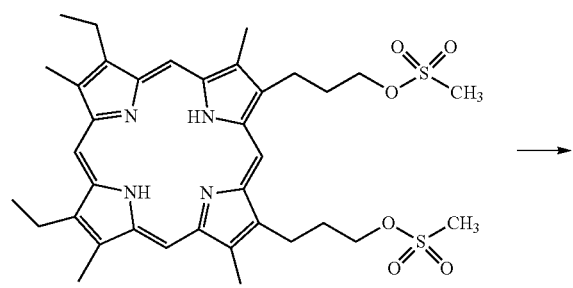

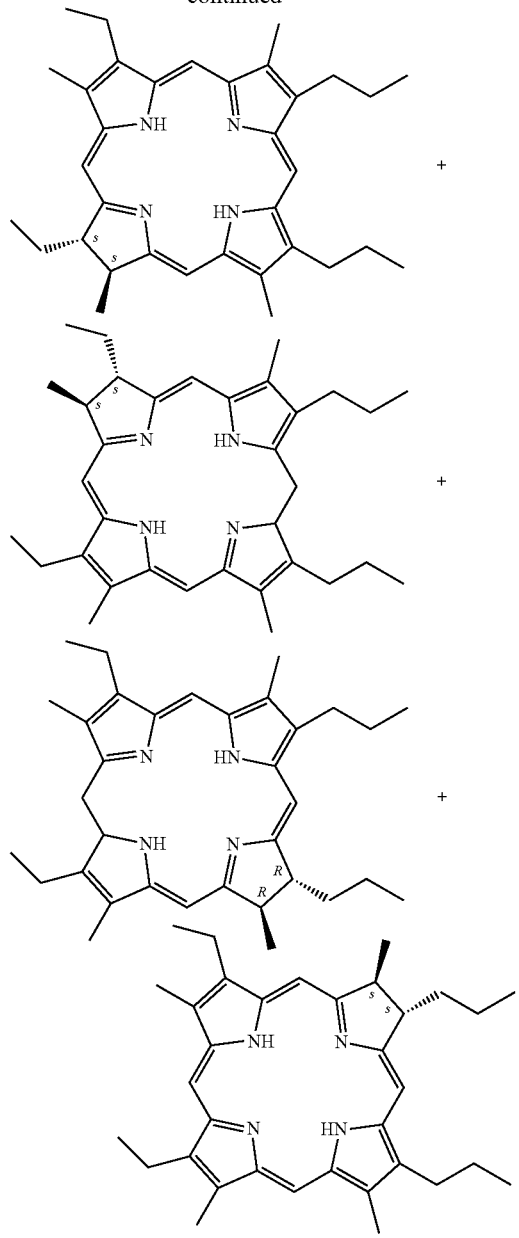

Overview
Steps/Stages
1.1 R: LiAlH$_4$, S:THF
2.1 R: FeCl$_2$, S: MeCN, S: CHCl$_3$
2.2 R: O$_2$
2.3 R: KOH, S: H$_2$O, S: MeOH
3.1 R: Na, S: CHMe$_2$CH$_2$CH$_2$OH
3.2 R: FeSO$_4$, R: HCl, S: AcOH
3.3 R: H$_2$SO$_4$, R: MeOH, S: MeOH
Notes
3) 54% overall, Reactants: 1, Reagents: 9, Solvents: 7, Steps: 3, Stages: 7, Most stages in any one step: 3

REFERENCES

Burns et al., Synthesis of chlorins from unsymmetrically substituted iron porphyrins, *Journal of the Chemical Society*, Perkin Transactions 1: Organic and Bio-Organic Chemistry (1972-1999), (12), 3119-31; 1988.

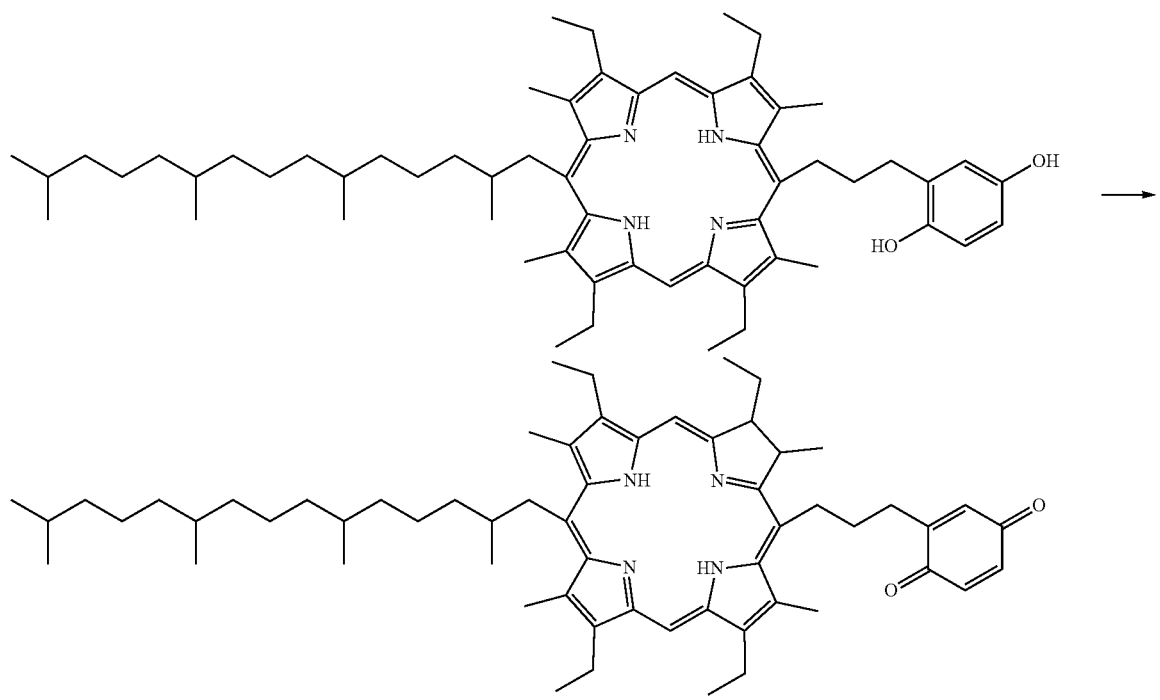

Overview
Steps/Stages
1.1 R: PbO$_2$, S: CH$_2$Cl$_2$
Notes
Reactants: 1, Reagents: 1, Solvents: 1, Steps: 1, Stages: 1, Most stages in any one step: 1

REFERENCES

Sakata et al., Synthesis of Photosynthetic model compound with a long alkyl chain and its incorporation into bovine serum albumin, *Tetrahedron*, 1989, 45(15), 4717-27.

Overview
Steps/Stages
1.1 R: Dabco, R: (L)-Ascorbic acid
2.1 R: H$_2$, C: Pd
3.1 R: F$_3$CCO$_2$H
Notes
1) Photochem., Reactants: 1, Reagents: 4, Catalysts: 1, Steps: 3, Stages: 3, Most stages in any one step: 1

REFERENCES

Smith et al., Site-specific reduction of unsymmetrically substituted porphyrins to give isomerically pure chlorins, *Journal of the Chemical Society, Chemical Communications*, 1987, (8), 613-14.

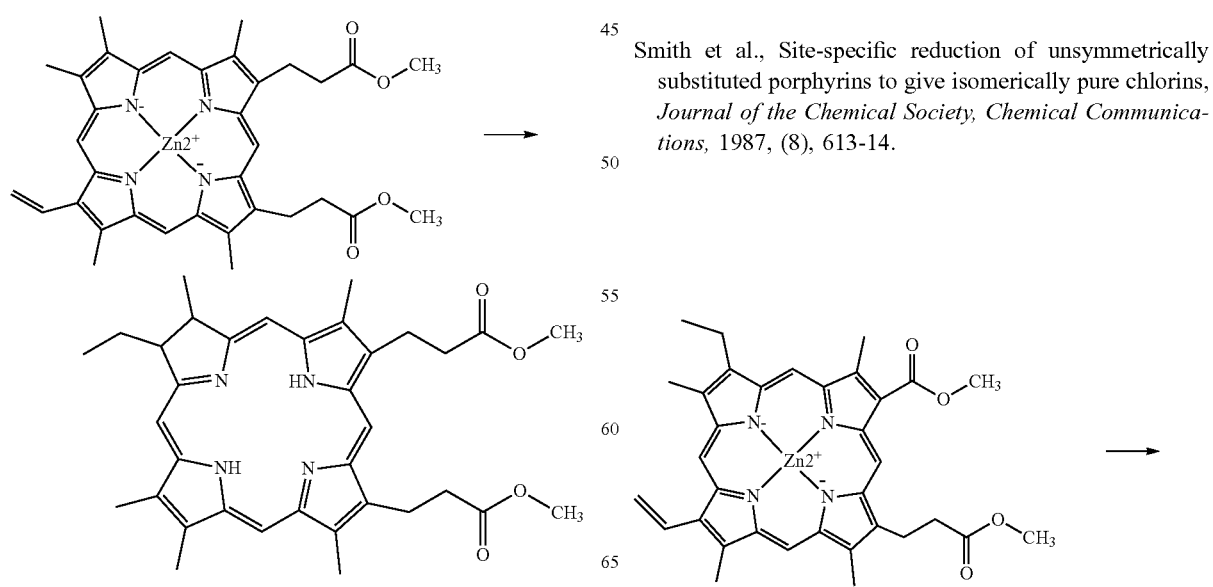

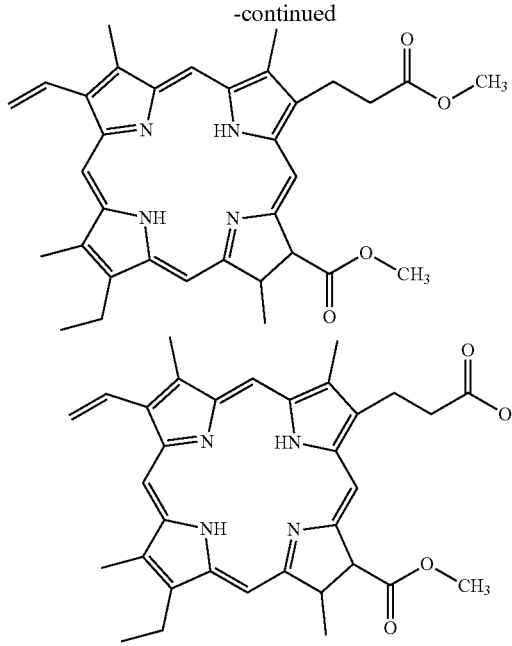

Overview
Steps/Stages
1.1 R: Dabco, R: (L)-Ascorbic acid
2.1 R: F$_3$CCO$_2$H
Notes
1) Photochem., Reactants: 1, Reagents: 3, Steps: 2, Stages: 2, Most stages in any one step: 1

REFERENCES

Smith et al., Site-specific reduction of unsymmetrically substituted porphyrins to give isomerically pure chlorins, *Journal of the Chemical Society, Chemical Communications*, 1987, (8), 613-14.

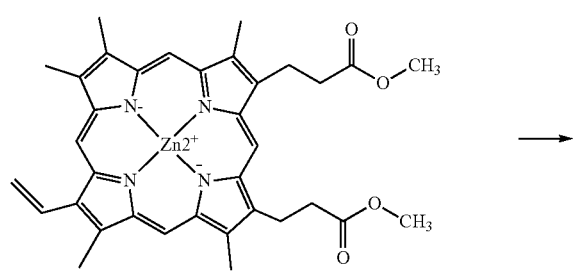

Notes
1) Photochem., Reactants: 1, Reagents: 3, Catalysts: 1, Steps: 2, Stages: 2, Most stages in any one step: 1

REFERENCES

Smith et al., Site-specific reduction of unsymmetrically substituted porphyrins to give isomerically pure chlorins, *Journal of the Chemical Society, Chemical Communications*, 1987, (8), 613-14.

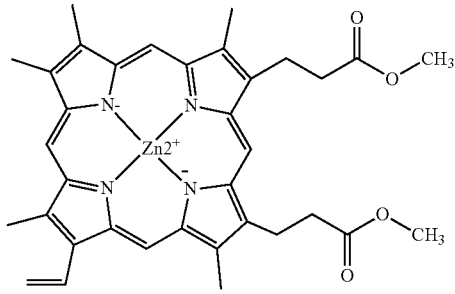 

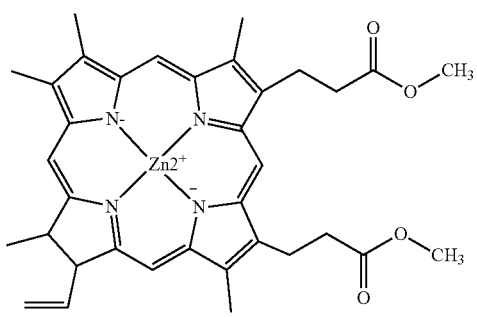

Overview
Stages/Steps
1.1 R: Dabco, R: (L)-Ascorbic acid, S: EtOH, S: Benzene
Notes
Photochem., Reactants: 1, Reagents: 2, Solvents: 2, Steps: 1, Stages: 1, Most stages in any one step: 1

REFERENCES

Iakovides et al., Regioselective photoreduction of zinc(II) porphyrins to give chlorins, *Photochemistry and Photobiology*, 1991, 54(3), 335-43.

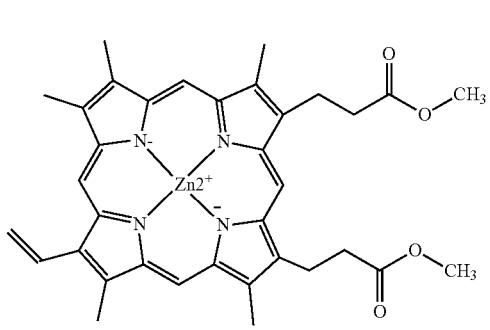 

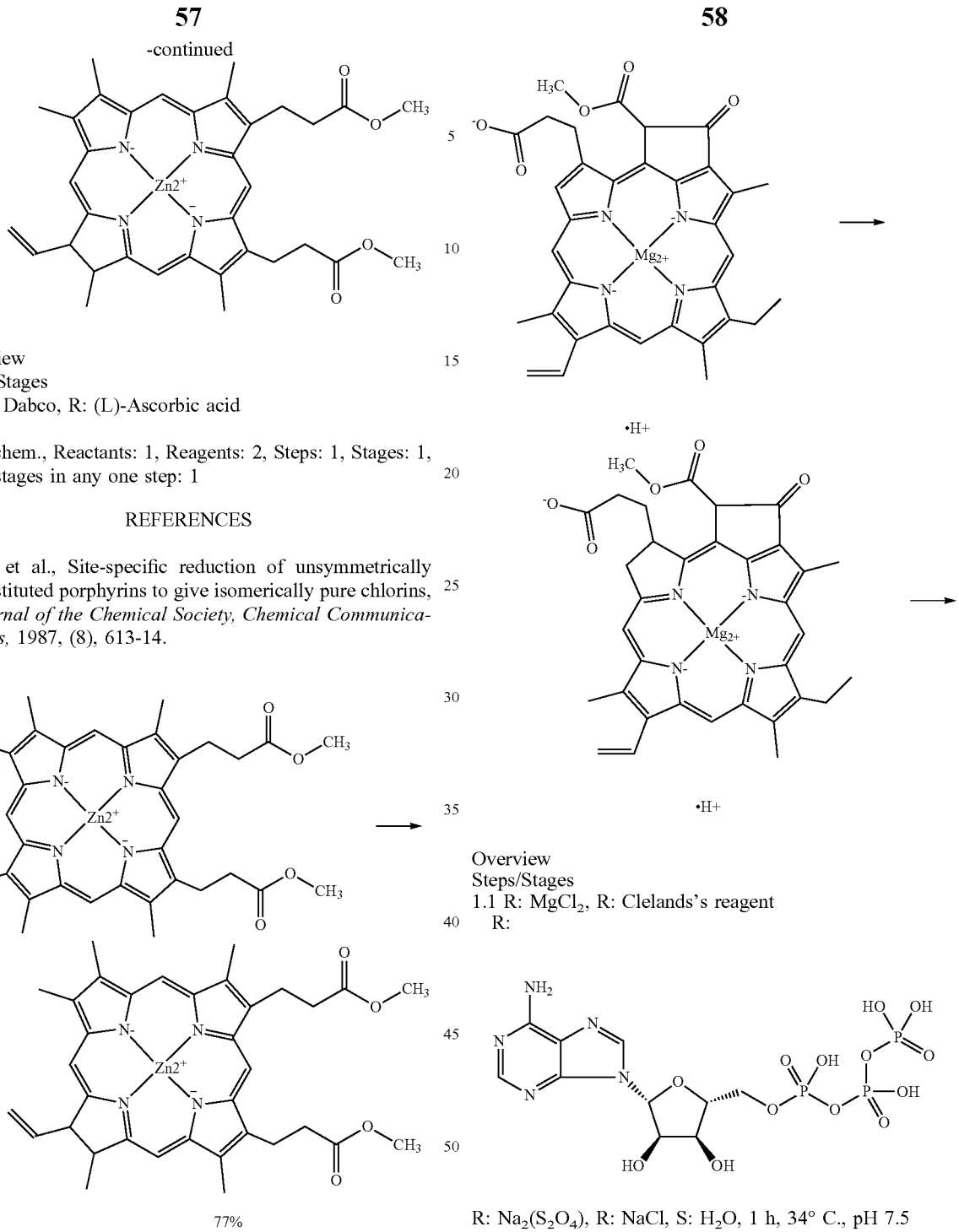

Overview
Steps/Stages
1.1 R: Dabco, R: (L)-Ascorbic acid
Notes
Photochem., Reactants: 1, Reagents: 2, Steps: 1, Stages: 1, Most stages in any one step: 1

REFERENCES

Smith et al., Site-specific reduction of unsymmetrically substituted porphyrins to give isomerically pure chlorins, *Journal of the Chemical Society, Chemical Communications*, 1987, (8), 613-14.

77%

Overview
Steps/Stages
1.1 R: Dabco, R: (L)-Ascorbic acid, S: EtOH, S: Benzene
Notes
Photochem., Reactants: 1, Reagents: 2, Solvents: 2, Steps: 1, Stages: 1, Most stages in any one step: 1

REFERENCES

Iakovides et al., Regioselective photoreduction of zinc(II) porphyrins to give chlorins, *Photochemistry and Photobiology*, 1991, 54(3), 335-43.

Overview
Steps/Stages
1.1 R: MgCl$_2$, R: Clelands's reagent
R:

R: Na$_2$(S$_2$O$_4$), R: NaCl, S: H$_2$O, 1 h, 34° C., pH 7.5
Notes
Regioselective, enzymic, described medium, biotransformation, cell free extract of *Escherichia coli* BL21 containing overexpressed protochlorophyllide a oxidoreductase from *Chlorobaculum tepidum* used, HEPES-NaOH buffered solution used, Reactants: 1, Reagents: 5, Solvents: 1, Steps: 1, Stages: 1, Most stages in any one step: 1

REFERENCES

Kiesel et al., Iron-Sulfur Cluster-dependent Catalysis of Chlorophyllide a Oxidoreductase from *Roseobacter denitrificans*, *Journal of Biological Chemistry*, 2015, 290(2), 1141-1154.

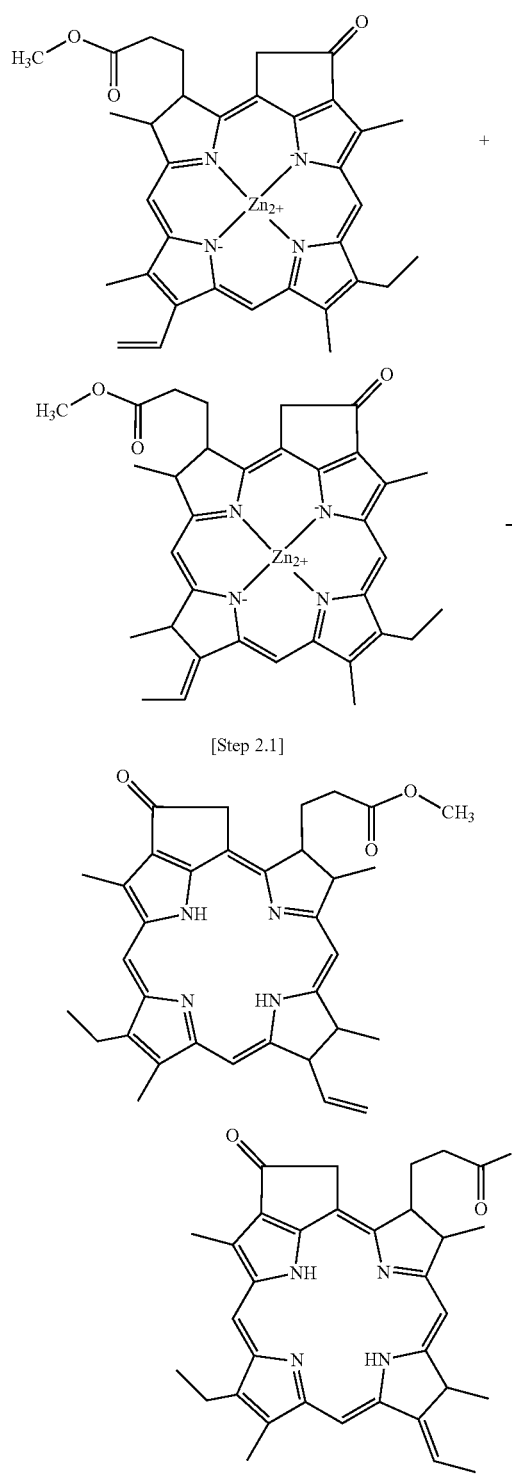

[Step 2.1]

Overview

Steps/Stages 1.1 R: (L)-Ascorbic acid, R: Dabco, S: EtOH, S: Benzene 2.1 R: F₃CCO₂H Notes 1) Photochem., Reactants: 2, Reagents: 3, Solvents: 2, Steps: 2, Most stages in any one step: 1

REFERENCES

Simpson et al., Ascorbic acid photoreductions of zinc(II) chlorophyll derivatives: access to metal-free isobacteriochlorins, *Journal of the American Chemical Society*, 1988, 110(9), 2854-61.

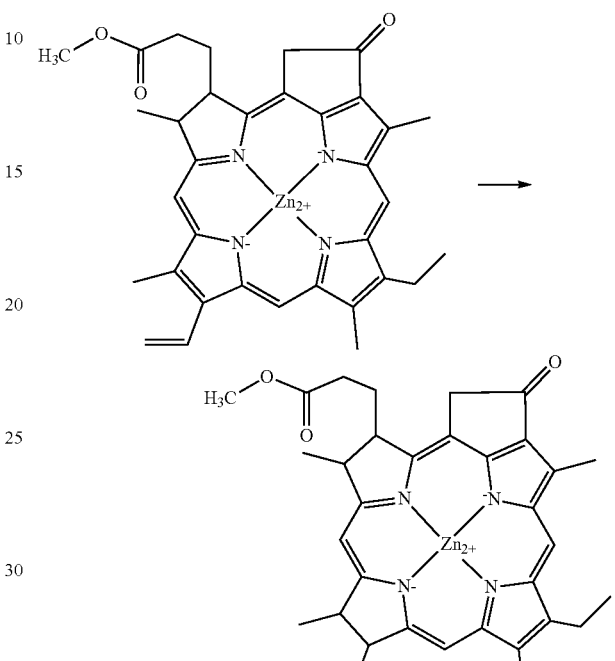

Overview

Steps/Stages 1.1 R: (L)-Ascorbic acid, R: Dabco, S: EtOH, S: Benzene

Notes

Photochem., Reactants: 1, Reagents: 2, Solvents: 2, Steps: 1, Stages: 1, Most stages in any one step: 1

REFERENCES

Simpson et al., Ascorbic acid photoreductions of zing(II) chlorophyll derivatives: access to metal-free isobacteriochlorins, *Journal of the American Chemical Society*, 1988, 110(9), 2854-61.

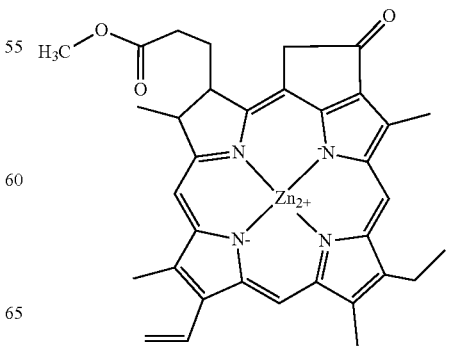

-continued

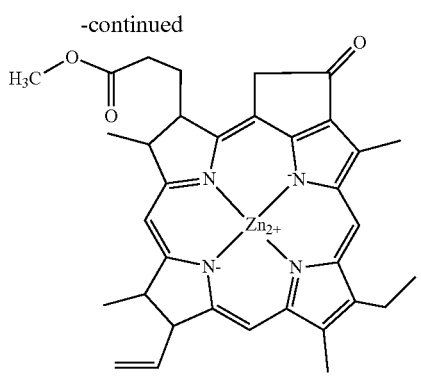

Overview
Steps/Stages
1.1 R: DDQ
Notes
Reactants: 1, Reagents: 1, Steps: 1, Stages: 1, Most stages in any one step: 1

REFERENCES

Smith et al., Isobacteriochlorophyll b analogs from photo-reduction of metallochlorins, *Journal of the American Chemical Society*, 1986, 108(21), 6834-5.

Example 3—New Small Molecules Inhibit YAP Function

Figure 11A:
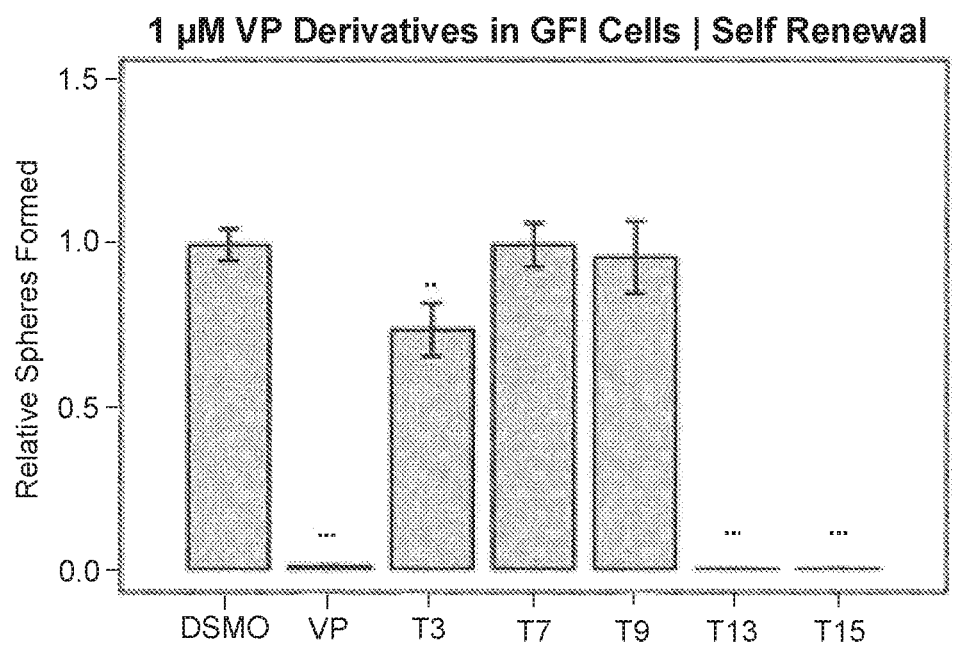
FIG. 11A shows the results of an exemplary self-renewal assay using a mouse medulloblastoma cell line, comparing verteporfin or a verteporfin derivative compound (T3, T7, T9, T13, or T15) to DMSO control. 1 micromolar (μM) concentration of verteporfin (VP) or a verteporfin derivative compound were added at day 1.
Figure 11B:
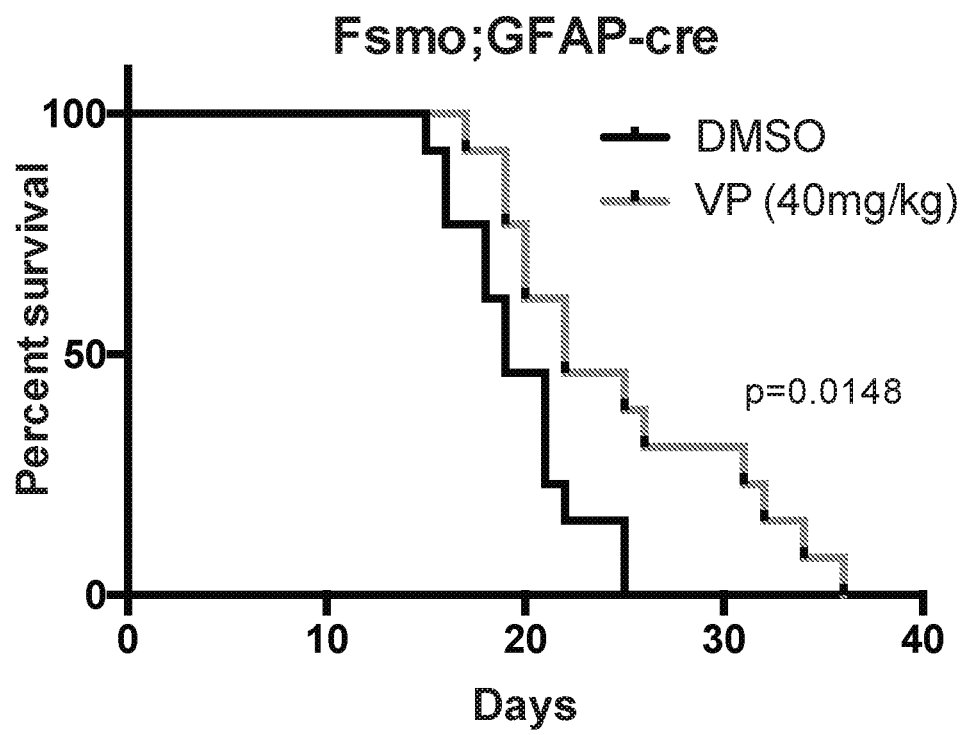
FIG. 11B shows an exemplary Kaplan-Meier survival curve for SMO-M2;GFAP-cre mice treated with vehicle (DMSO) or verteporfin, administered by intraperitoneal (IP) injection. N=8 each group.

While verteporfin (VP) is a FDA approved drug for treating macular degeneration, it has poor solubility, which may render it suboptimal for certain oncology application. In fact, previous studies showing in vivo efficacy of VP in mouse models report that VP crystals were present in large quantities at the site of injection. Nevertheless, VP treatment can increase survival in SMO-M2;GFAP-cre mice (FIG. 11B). Therefore, new inhibitors with better solubility and potency are greatly desired. To generate such compounds, verteporfin derivative compounds (T1-T30) were developed (Example 2 & FIG. 8).

Figures 9A, 9B:
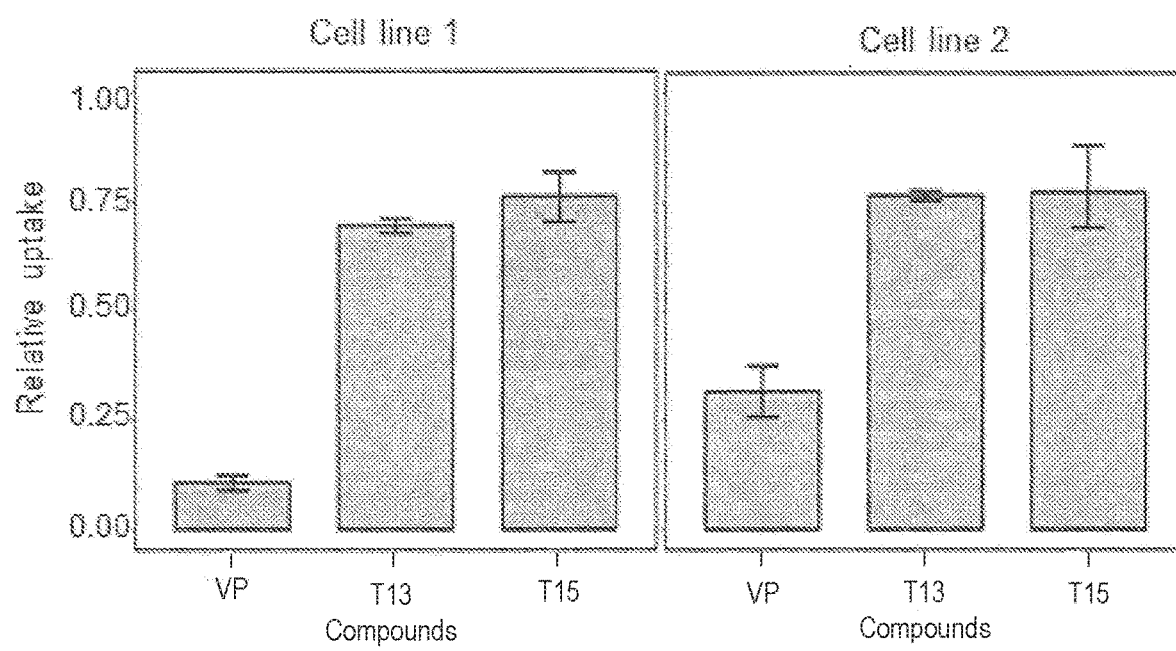
FIG. 9A) shows the results of a cellular uptake test. Uptake was calculated by measuring relative fluorescence in two different primary medulloblastoma cell lines. Absorbance measurements were normalized to t=0 with drugs in the well, the drugs were washed out 30 minutes later, and absorbance was measured again.
FIG. 9B) $IC_{50}$ in a mouse medulloblastoma tumorsphere cell line treated with verteporfin or a verteporfin derivative compound (T10, T11, T13, T14, or T15). DMSO was used as a control.

Cellular uptake (FIG. 9A), the concentration of an inhibitor where the response (or binding) is reduced by half ($IC_{50}$) (FIG. 9B), solubility (Table 2), and the effect on self-renewal (FIG. 11A) of selected verteporfin derivative compounds were tested.

Figure 10:
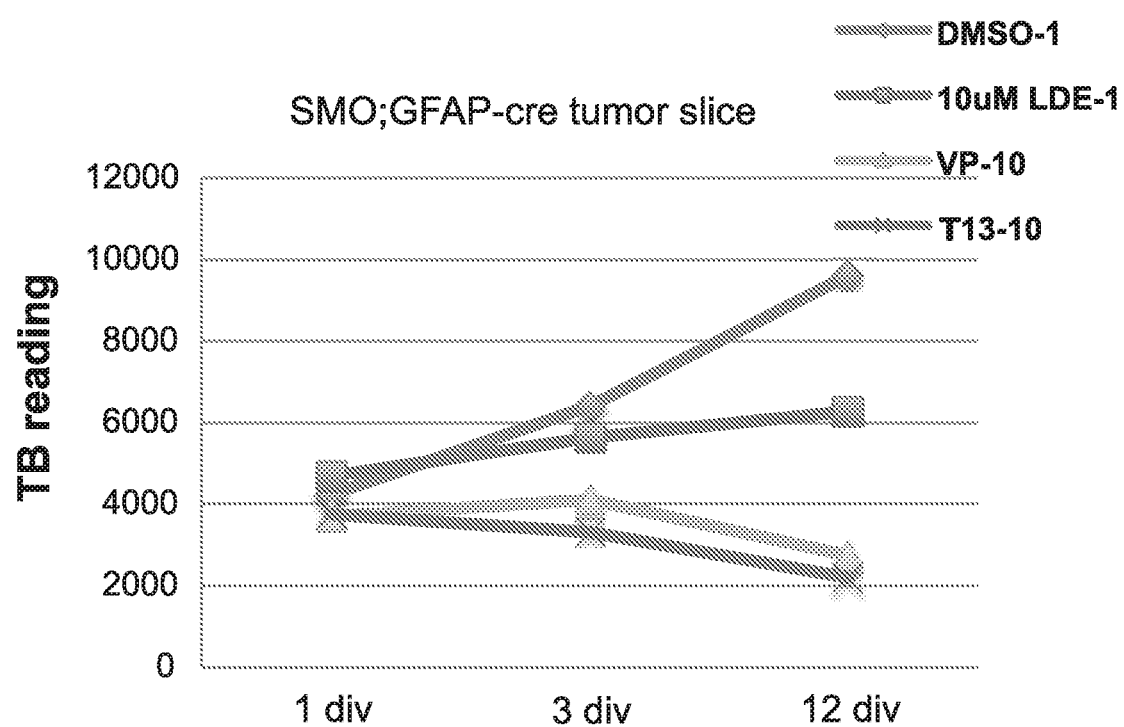
FIG. 10 shows the effect on SMO-M2;GFAP-cre tumor cells of treatment with DMSO (control), 10 μM of a verteporfin derivative compound (T13), 10 μM verteporfin, or 10 μM LDE-225 (LDE).

While decreased solubility and activity when compared to VP were observed for some compounds including, for example, T9, some compounds including, for example, T13, are both more soluble and potent than VP (FIGS. 9-11). The data show that the synthesized verteporfin derivative compounds are effective in inhibiting YAP1 activity and treating cancer.

TABLE 2

Solubility of verteporfin derivative compounds

| | Water | | Buffer (pH = 2) | |
|---|---|---|---|---|
| Compound | mg/mL | result | mg/mL | result |
| Verteporfin | 1 mg/3 mL | insoluble | 1 mg/3 mL | insoluble |
| T3 | 1 mg/3 mL | insoluble | 1 mg/3 mL | insoluble |
| T7 | 1 mg/0.5 mL | soluble dark green solution | 1 mg/0.5 mL | soluble dark green solution |

TABLE 2-continued

Solubility of verteporfin derivative compounds

| | Water | | Buffer (pH = 2) | |
|---|---|---|---|---|
| Compound | mg/mL | result | mg/mL | result |
| T15 | 1 mg/0.5 mL | soluble dark green solution | 1 mg/0.5 mL | soluble dark green solution |
| T1 | 1 mg/3 mL | insoluble | 1 mg/3 mL | ~20% dissolved |
| T4 | 0.5 mg/3 mL | insoluble | 0.6 mg/2 mL | ~80% dissolved |
| T5 | 1 mg/2 mL | soluble | 1 mg/1 mL | soluble |
| T8 | 1 mg/3 mL | insoluble | 1 mg/3 mL | insoluble |
| T10 | 1 mg/3 mL | insoluble | 1 mg/3 mL | insoluble |
| T11 | 1 mg/1 mL | insoluble | 1 mg/3 mL | ~70% dissolved green solution |
| T14 | 1 mg/1 mL | insoluble | 1 mg/3 mL | soluble dark green solution |

Preparation of Buffer (pH = 2):
1. 16.6 mL of $H_3PO_4$ (85.5%) solution was diluted to 1000 mL by adding water;
2. Take 72.5 mL of above solution and mix with 27.5 mL of $Na_2HPO_4$ (0.2M) solution.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A verteporfin derivative compound including at least one of:

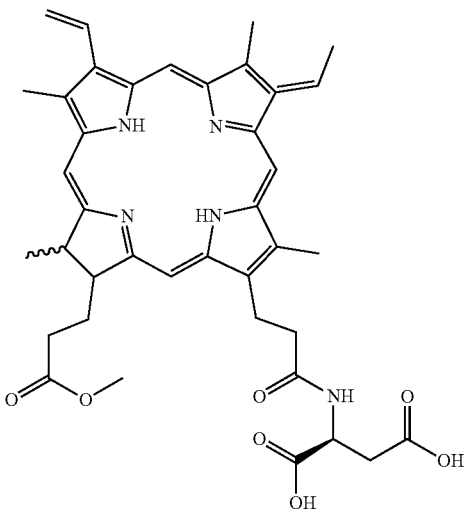

(3-(7-(3-methoxy-3-oxopropyl)-2,8,12,17-tetramethyl-13,18-divinyl-7H,8H-porphyrin-3-yl)propanoyl)-L-aspartic acid;

63
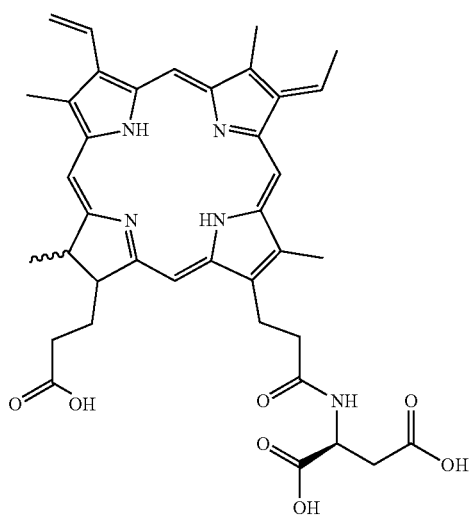
(3-(7-(2-carboxyethyl)-2,8,12,17-tetramethyl-13,18-divinyl-7H,8H-porphyrin-3-yl)propanoyl)-L-aspartic acid;
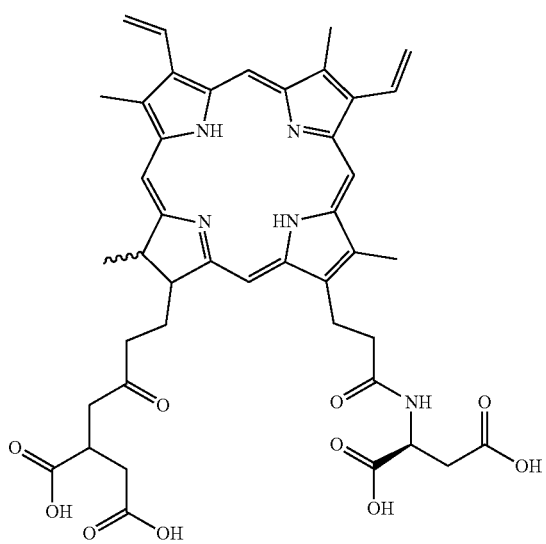 [SMILES: C=CC1=C(C)c2cc3[nH]c(cc4nc(cc5[nH]c(cc1n2)c(C)c5CCC(=O)N[C@@H](CC(=O)O)C(=O)O)C(CCC(=O)CC(CC(=O)O)C(=O)O)C4C)c(C)c3C=C]
(3-(7-(5,6-dicarboxy-3-oxohexyl)-2,8,12,17-tetramethyl-13,18-divinyl-7H,8H-porphyrin-3-yl)propanoyl)-L-aspartic acid;
64
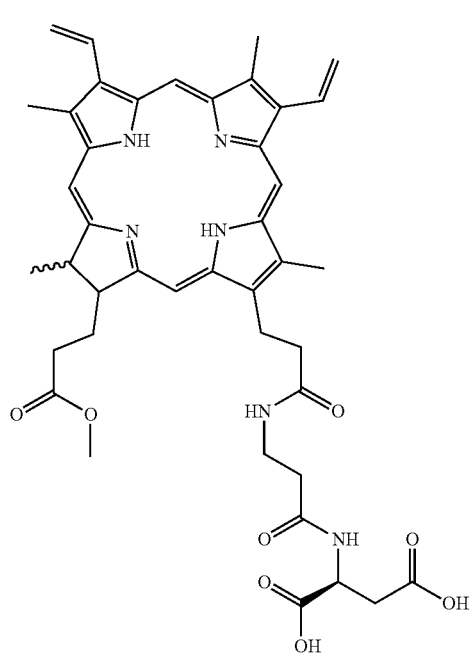 [SMILES: C=CC1=C(C)c2cc3[nH]c(cc4nc(cc5[nH]c(cc1n2)c(C)c5CCC(=O)NCCC(=O)N[C@@H](CC(=O)O)C(=O)O)C(CCC(=O)OC)C4C)c(C)c3C=C]
(3-(3-(7-(3-methoxy-3-oxopropyl)-2,8,12,17-tetramethyl-13,18-divinyl-7H,8H-porphyrin-3-yl)propanamido)propanoyl)-L-aspartic acid;
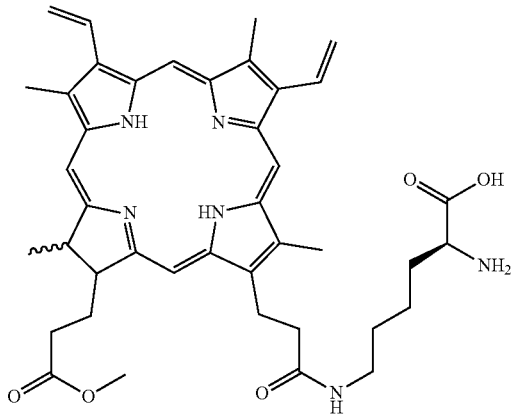 [SMILES: C=CC1=C(C)c2cc3[nH]c(cc4nc(cc5[nH]c(cc1n2)c(C)c5CCC(=O)NCCCC[C@H](N)C(=O)O)C(CCC(=O)OC)C4C)c(C)c3C=C]
$N^6$-(3-(7-(3-methoxy-3-oxopropyl)-2,8,12,17-tetramethyl-13,18-divinyl-7H,8H-porphyrin-3-yl)propanoyl)-L-lysine;

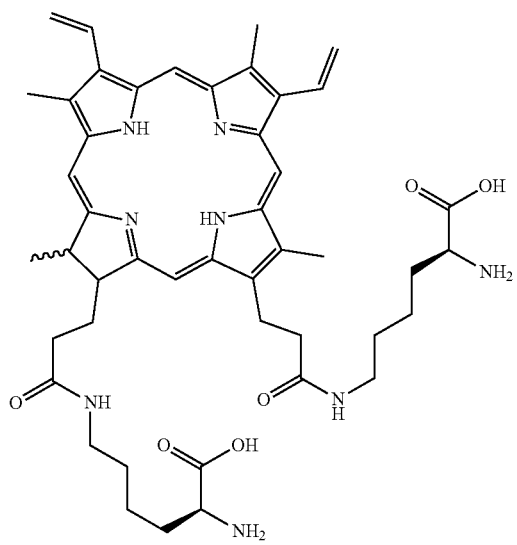 [SMILES: C=CC1=C(C)c2cc3[nH]c(cc4nc(cc5[nH]c(cc1n2)c(C)c5CCC(=O)NCCCC[C@H](N)C(=O)O)C(CCC(=O)NCCCC[C@H](N)C(=O)O)C4C)c(C)c3C=C]

(2S,2'S)-6,6'-((3,3'-(2,8,12,17-tetramethyl-13,18-divinyl-7H,8H-porphyrin-3,7-diyl)bis(propanoyl))bis(azanediyl))bis(2-aminohexanoic acid);

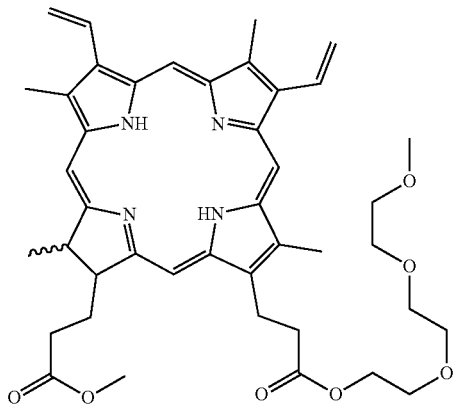 [SMILES: C=CC1=C(C)c2cc3[nH]c(cc4nc(cc5[nH]c(cc1n2)c(C)c5CCC(=O)OCCOCCOCCOC)C(CCC(=O)OC)C4C)c(C)c3C=C]

2-(2-(2-methoxyethoxy)ethoxy)ethyl 3-(7-(3-methoxy-3-oxopropyl)-2,8,12,17-tetramethyl-13,18-divinyl-7H,8H-porphyrin-3-yl)propanoate;

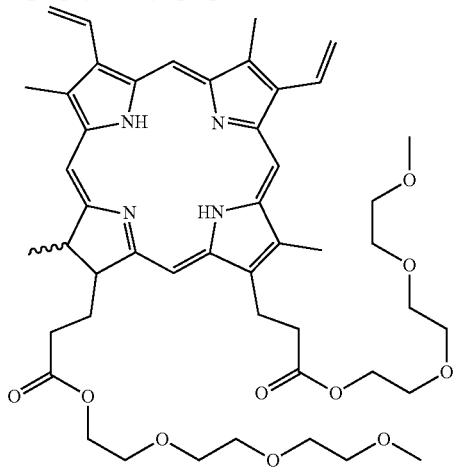 [SMILES: C=CC1=C(C)c2cc3[nH]c(cc4nc(cc5[nH]c(cc1n2)c(C)c5CCC(=O)OCCOCCOCCOC)C(CCC(=O)OCCOCCOCCOC)C4C)c(C)c3C=C]

bis(2-(2-(2-methoxyethoxy)ethoxy)ethyl) 3,3'-(2,8,12,17-tetramethyl-13,18-divinyl-7H,8H-porphyrin-3,7-diyl)dipropionate;

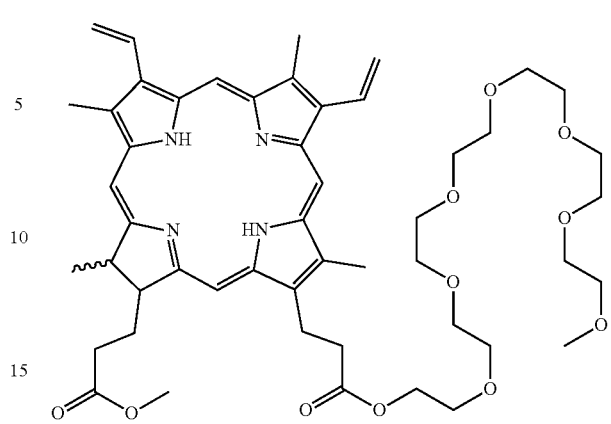

2,5,8,11,14,17,20-heptaoxadocosan-22-yl 3-(7-(3-methoxy-3-oxopropyl)-2,8,12,17-tetramethyl-13,18-divinyl-7H,8H-porphyrin-3-yl)propanoate;

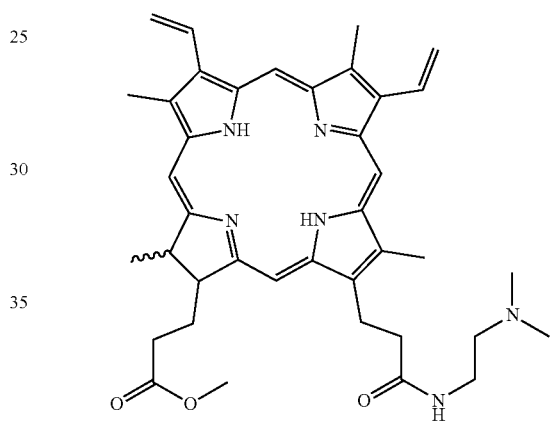

methyl 3-(3-(3-((2-(dimethylamino)ethyl)amino)-3-oxopropyl)-2,8,12,17-tetramethyl-13,18-divinyl-7H,8H-porphyrin-7-yl)propanoate;

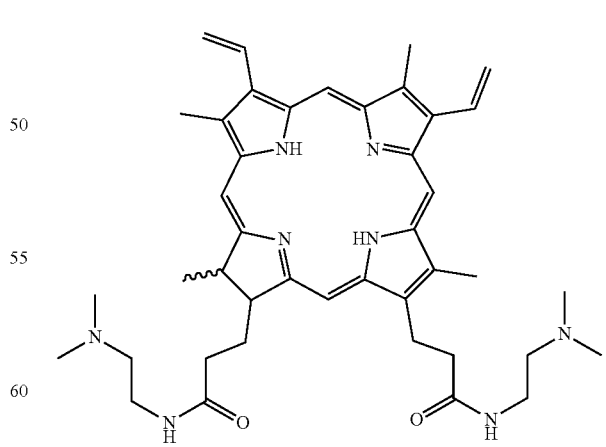

3,3'-(2,8,12,17-tetramethyl-13,18-divinyl-7H,8H-porphyrin-3,7-diyl)bis(N-(2-(dimethylamino)ethyl)propanamide);

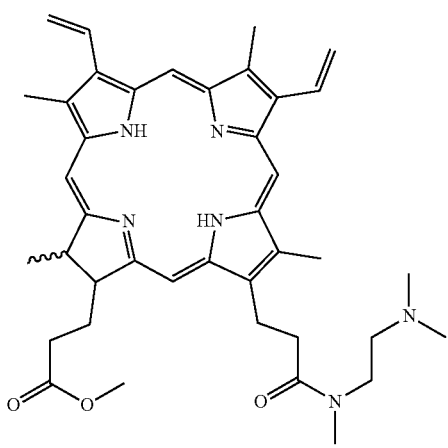 [SMILES: C=CC1=C(C)c2cc3[nH]c(cc4nc(cc5[nH]c(cc1n2)c(C)c5CCC(=O)N(C)CCN(C)C)C(CCC(=O)OC)C4C)c(C)c3C=C]

methyl 3-(3-(3-((2-(dimethylamino)ethyl)(methyl)amino)-3-oxopropyl)-2,8,12,17-tetramethyl-13,18-divinyl-7H,8H-porphyrin-7-yl)propanoate; and

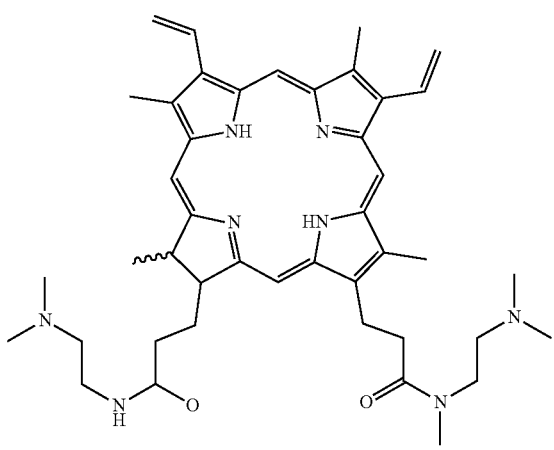

N-(2-(dimethylamino)ethyl)-3-(7-(2-(dimethylamino)ethyl)amino)-3-oxopropyl)-2,8,12,17-tetramethyl-13,18-divinyl-7H,8H-porphyrin-3-yl)-N-methylpropanamide.

2. A verteporfin derivative compound including at least one of:

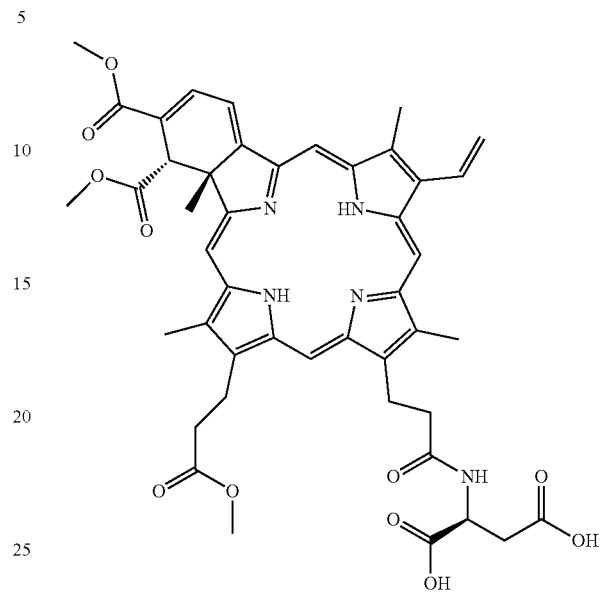

(2S)-2-[3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]butanedioic acid;

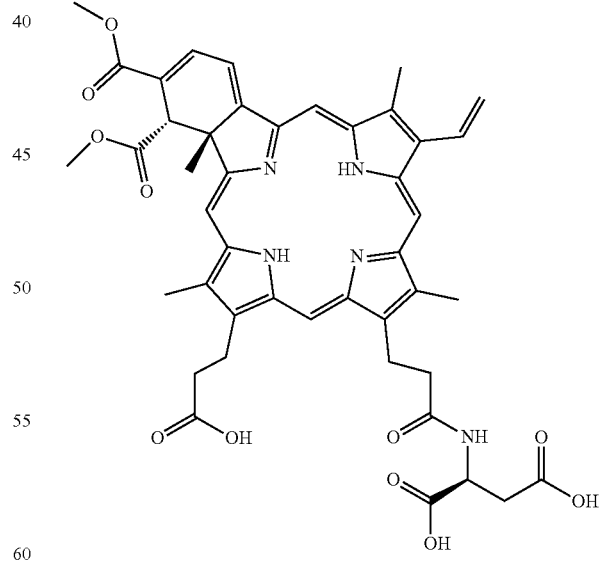

(2S)-2-[3-[(23S,24R)-14-ethenyl-5-(2-carboxyethyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]butanedioic acid;

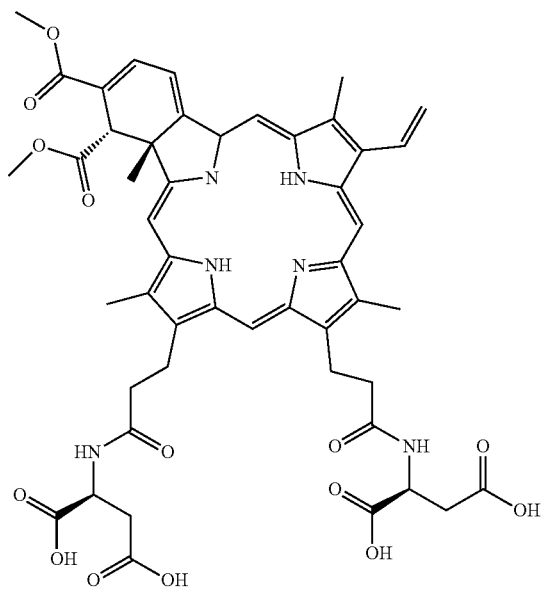 [SMILES: C=Cc1c(C)/c2[nH]/c1=C\C1=NC(=C\c3[nH]c(c(C)c3CCC(=O)N[C@@H](CC(=O)O)C(=O)O)/C=C3\NC(\C=2)C2=CC=C(C(=O)OC)[C@@H](C(=O)OC)[C@]23C)/C(CCC(=O)N[C@@H](CC(=O)O)C(=O)O)=C1C]

(2S)-2-[3-[(23S,24R)-14-ethenyl-5-[3-[[(1S)-1,2-dicarboxyethyl]amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]butanedioic acid;

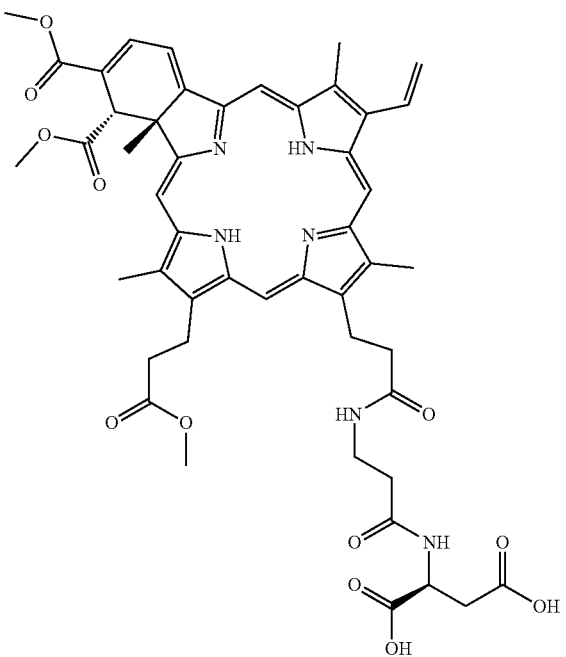 [SMILES: C=Cc1c(C)c2cc3nc(cc4[nH]c(cc5nc(cc1[nH]2)C(C)=C5CCC(=O)NCCC(=O)N[C@@H](CC(=O)O)C(=O)O)c(CCC(=O)OC)c4C)[C@@]1(C)C3=CC=C(C(=O)OC)[C@H]1C(=O)OC]

(2S)-2-[3-[3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13, 6.18,11.113,16.019,24]octacosa-1,3,5,7,9,11(27),12,14,16,18(25),19,21-dodecaen-9-yl]propanoylamino]propanoylamino]butanedioic acid;

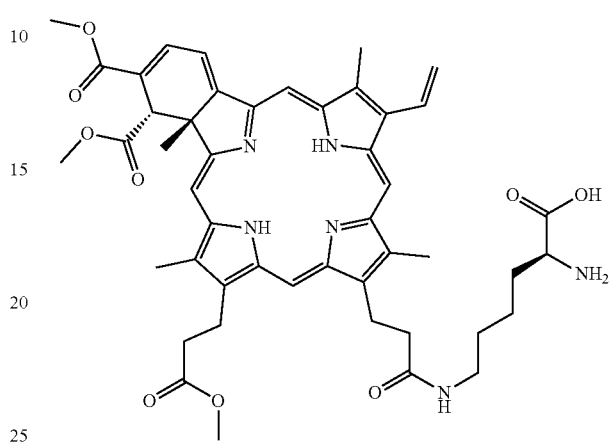

(2S)-2-amino-6-[3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13, 6.18,11.113,16.019,24]octacosa-1,3,5,7,9,11(27),12, 14,16,18(25),19,21-dodecaen-9-yl]propanoylamino] hexanoic acid;

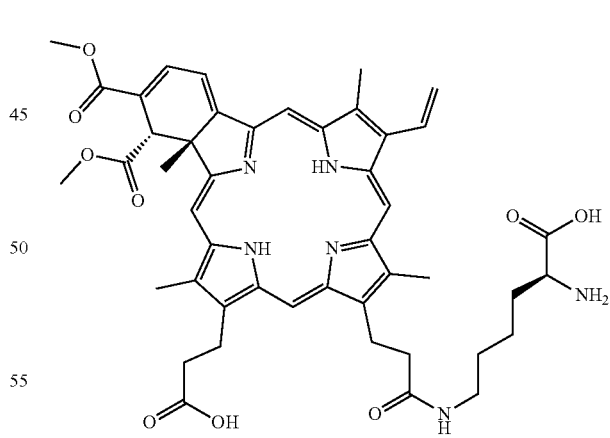

(2S)-2-amino-6-[3-[(23S,24R)-14-ethenyl-5-(2-carboxyethyl)-22,23-bis(methoxycarbonyl)-4,10,15,24-tetramethyl-25,26,27,28-tetraazahexacyclo[16.6.1.13,6.18, 11.113,16.019,24]octacosa-1,3,5,7,9,11(27),12,14,16, 18(25),19,21-dodecaen-9-yl]propanoylamino] hexanoic acid;

71

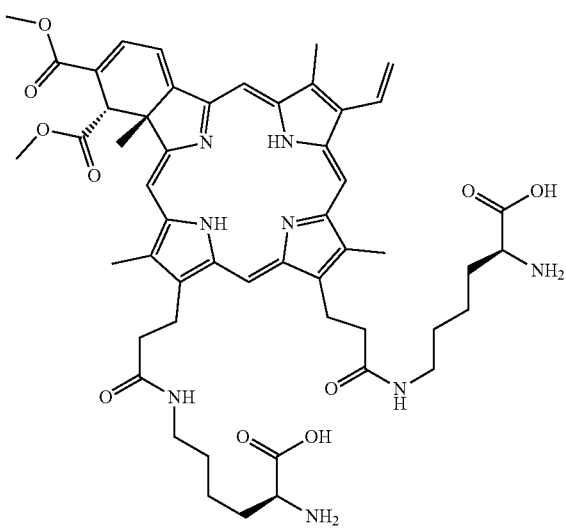 [SMILES: C=Cc1c(C)c2cc3nc(cc4[nH]c(cc5nc(cc1[nH]2)C(C)=C5CCC(=O)NCCCC[C@H](N)C(=O)O)c(CCC(=O)NCCCC[C@H](N)C(=O)O)c4C)[C@@]1(C)C3=CC=C(C(=O)OC)[C@H]1C(=O)OC]

(2S)-2-amino-6-[3-[(23S,24R)-14-ethenyl-5-[3-[[(5S)-5-amino-5-carboxy-pentyl]amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]hexanoic acid;

72

2-[2-(2-methoxyethoxy)ethoxy]ethyl 3-[(23S,24R)-14-ethenyl-5-[3-[2-[2-(2-methoxyethoxy)ethoxy]ethoxy]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoate;

Methyl 3-[(23S,24R)-14-ethenyl-9-[3-[2-[2-(2-methoxyethoxy)ethoxy]ethoxy]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoate;

Methyl 3-[(23S,24R)-14-ethenyl-9-[3-[2-[2-[2-[2[2-[2-(2-methoxyethoxy)ethoxy]ethoxy]ethoxy]ethoxy]ethoxy]ethoxy]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoate;

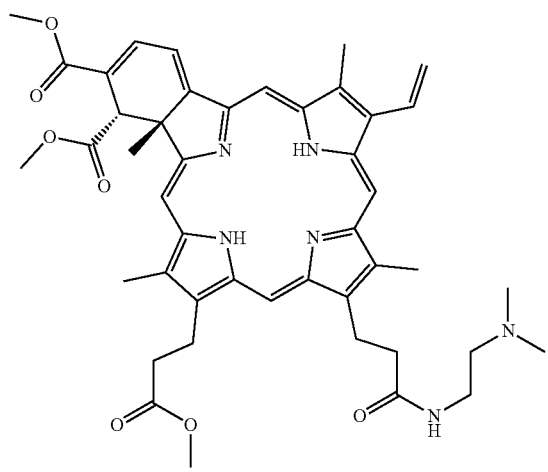

Methyl 3-[(23S,24R)-14-ethenyl-9-[3-[2-(dimethylamino)ethylamino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoate;

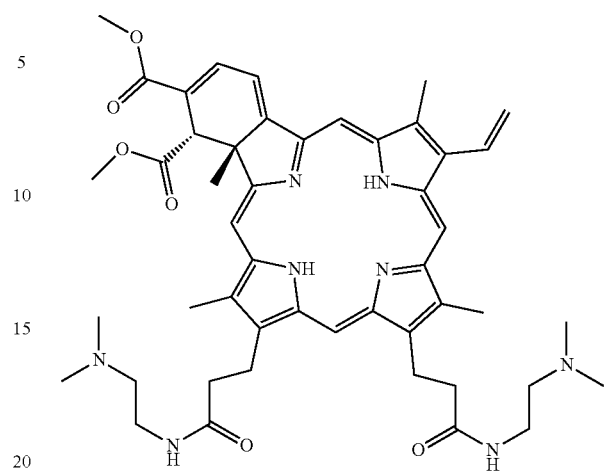

N-[2-(dimethylamino)ethyl]-3-[(23S,24R)-14-ethenyl-5-[3-[2-(dimethylamino)ethylamino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanamide;

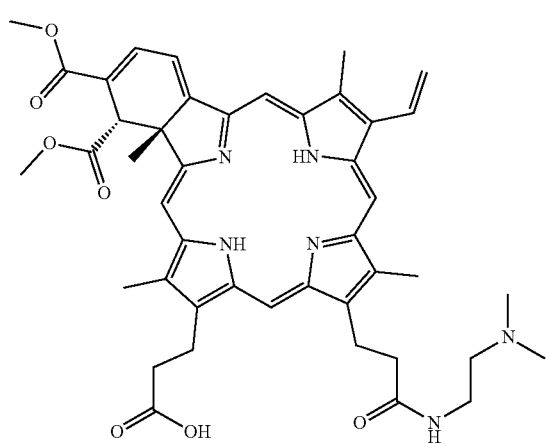

3-[(23S,24R)-14-ethenyl-9[3-[2-(dimethylamino)ethylamino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoic acid;

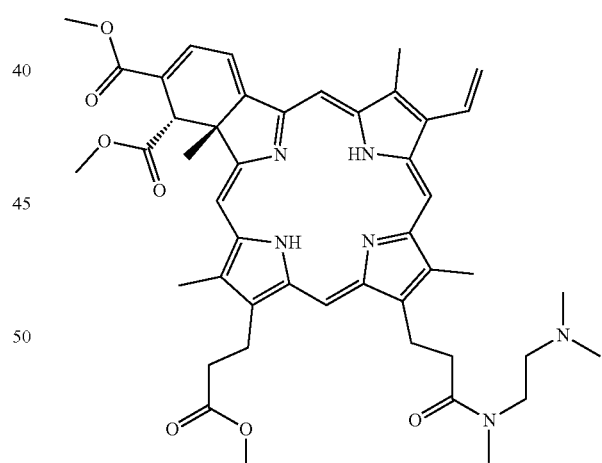

Methyl 3-[(23S,24R)-14-ethenyl-9-[3-[2-(dimethylamino)ethyl-methyl-amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoate; and

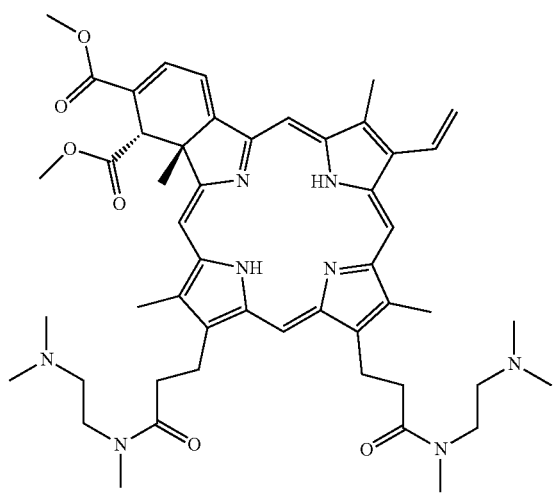

N-[2-(dimethylamino)ethyl]-3-[(23 S,24R)-14-ethenyl-5-[3-[2-(dimethylamino)ethyl-methyl-amino]-3-oxo-propy 1]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]-N-methyl-propanamide.

3. The verteporfin derivative compound of claim 2, wherein the verteporfin derivative compound is at least one of:

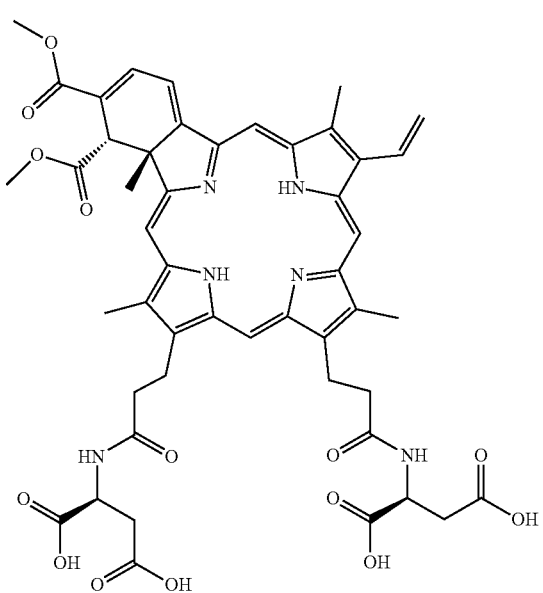 [SMILES: C=Cc1c(C)c2cc3nc(cc4[nH]c(cc5nc(cc1[nH]2)C(C)=C5CCC(=O)N[C@@H](CC(=O)O)C(=O)O)c(CCC(=O)N[C@@H](CC(=O)O)C(=O)O)c4C)[C@@]1(C)C3=CC=C(C(=O)OC)[C@H]1C(=O)OC]

(2 S)-2-[3-[(23 S,24R)-14-ethenyl-5-[3-[[(1S)-1,2-dicarboxyethyl]amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]butanedioic acid;

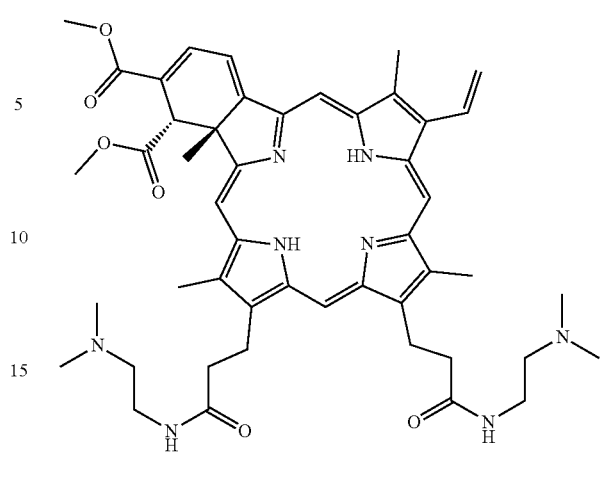

N-[2-(dimethylamino)ethyl]-3-[(23S,24R)-14-ethenyl-5-[3-[2-(dimethylamino)ethylamino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5, 7,9, 11 (27), 12, 14, 16, 18(25), 19,21-dodecaen-9-yl]propanamide; and

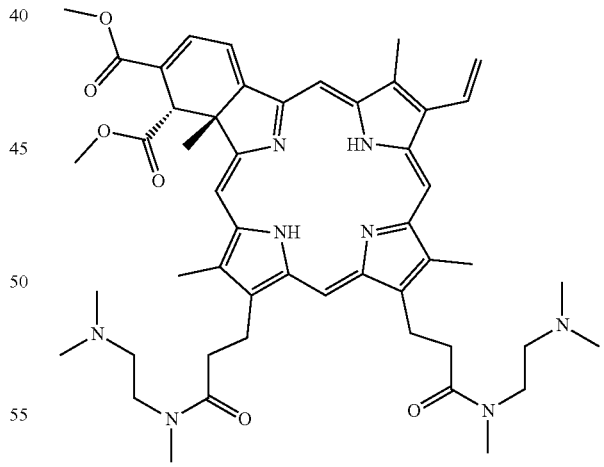

N-[2-(dimethylamino)ethyl]-3-[(23S,24R)-14-ethenyl-5-[3-[2-(dimethylamino)ethyl-methyl-amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]-N-methyl-propanamide.

4. A pharmaceutical composition comprising a verteporfin derivative compound and a pharmaceutically acceptable excipient, the verteporfin derivative compound including at least one of:

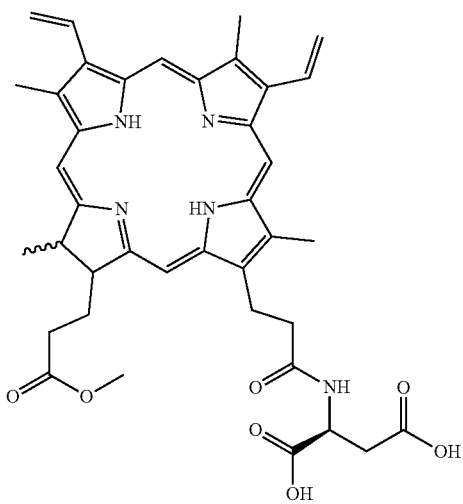 [SMILES: C=CC1=C(C)c2cc3[nH]c(cc4nc(cc5[nH]c(cc1n2)c(C)c5CCC(=O)N[C@@H](CC(=O)O)C(=O)O)C(CCC(=O)OC)C4C)c(C)c3C=C]

(3-(7-(3-methoxy-3-oxopropyl)-2,8,12,17-tetramethyl-13,18-divinyl-7H,8H-porphyrin-3-yl)propanoyl)-L-aspartic acid;

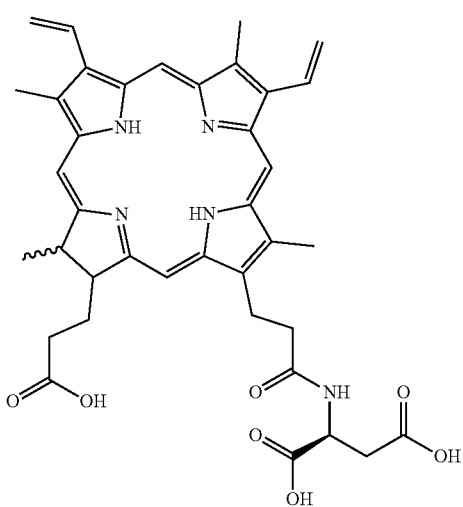 [SMILES: C=CC1=C(C)c2cc3[nH]c(cc4nc(cc5[nH]c(cc1n2)c(C)c5CCC(=O)N[C@@H](CC(=O)O)C(=O)O)C(CCC(=O)O)C4C)c(C)c3C=C]

(3-(7-(2-carboxyethyl)-2,8,12,17-tetramethyl-13,18-divinyl-7H,8H-porphyrin-3-yl)propanoyl)-L-aspartic acid;

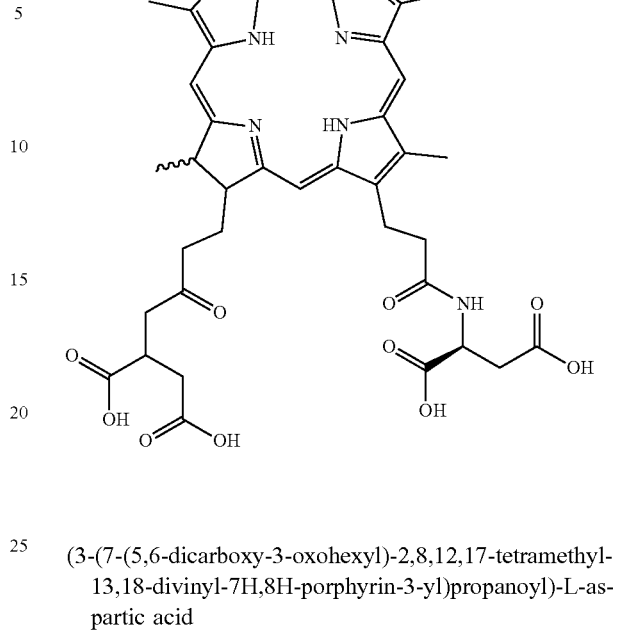

(3-(7-(5,6-dicarboxy-3-oxohexyl)-2,8,12,17-tetramethyl-13,18-divinyl-7H,8H-porphyrin-3-yl)propanoyl)-L-aspartic acid

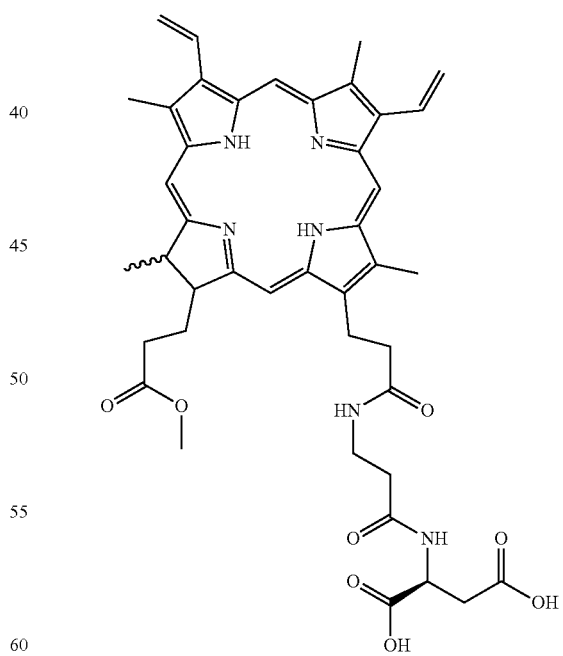

(3-(3-(7-(3-methoxy-3-oxopropyl)-2,8,12,17-tetramethyl-13,18-divinyl-7H,8H-porphyrin-3-yl)propanamido)propanoyl)-L-aspartic acid;

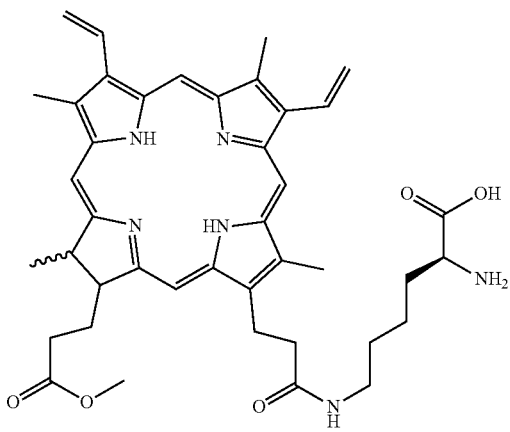 [SMILES: C=CC1=C(C)c2cc3[nH]c(cc4nc(cc5[nH]c(cc1n2)c(C)c5CCC(=O)NCCCC[C@H](N)C(=O)O)C(CCC(=O)OC)C4C)c(C)c3C=C]

N⁶-(3-(7-(3-methoxy-3-oxopropyl)-2,8,12,17-tetramethyl-13,18-divinyl-7H,8H-porphyrin-3-yl)propanoyl)-L-lysine;

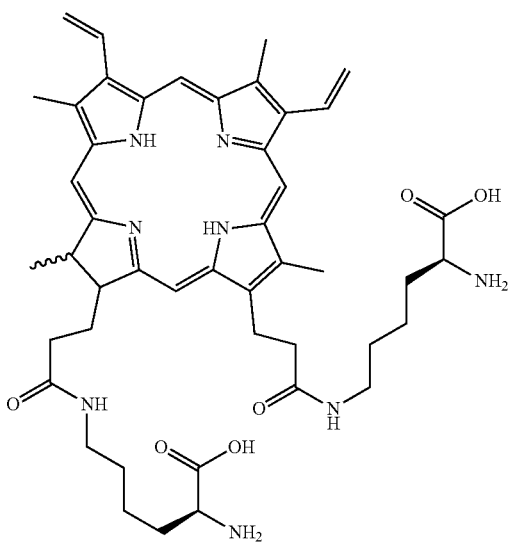 [SMILES: C=CC1=C(C)c2cc3[nH]c(cc4nc(cc5[nH]c(cc1n2)c(C)c5CCC(=O)NCCCC[C@H](N)C(=O)O)C(CCC(=O)NCCCC[C@H](N)C(=O)O)C4C)c(C)c3C=C]

(2S,2'S)-6,6'-((3,3'-(2,8,12,17-tetramethyl-13,18-divinyl-7H,8H-porphyrin-3,7-diyl)bis(propanoyl))bis(azanediyl))bis(2-aminohexanoic acid);

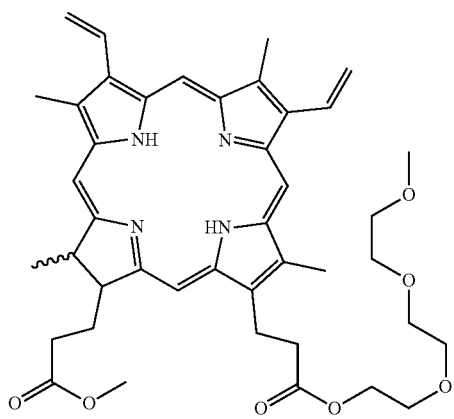 [SMILES: C=CC1=C(C)c2cc3[nH]c(cc4nc(cc5[nH]c(cc1n2)c(C)c5CCC(=O)OCCOCCOCCOC)C(CCC(=O)OC)C4C)c(C)c3C=C]

2-(2-(2-methoxyethoxy)ethoxy)ethyl 3-(7-(3-methoxy-3-oxopropyl)-2,8,12,17-tetramethyl-13,18-divinyl-7H,8H-porphyrin-3-yl)propanoate;

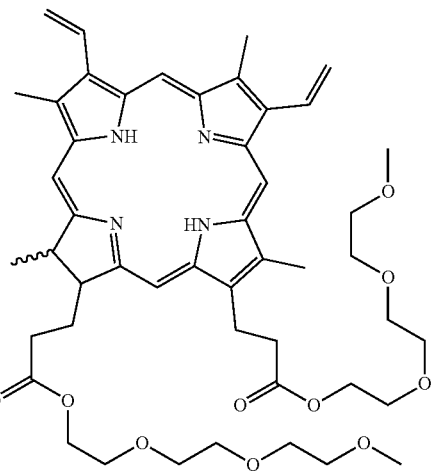

bis(2-(2-(2-methoxyethoxy)ethoxy)ethyl) 3,3'-(2,8,12,17-tetramethyl-13,18-divinyl-7H,8H-porphyrin-3,7-diyl)dipropionate;

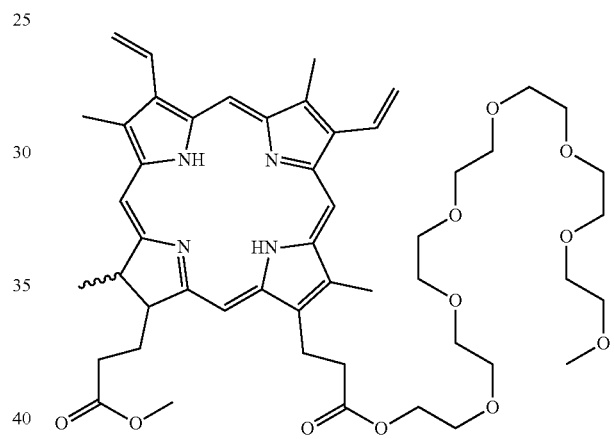

2,5,8,11,14,17,20-heptaoxadocosan-22-yl 3-(7-(3-methoxy-3-oxopropyl)-2,8,12,17-tetramethyl-13,18-divinyl-7H,8H-porphyrin-3-yl)propanoate;

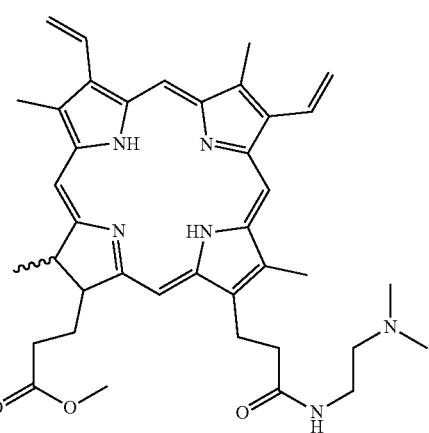

methyl 3-(3-(3-(((2-(dimethylamino)ethyl)amino)-3-oxopropyl)-2,8,12,17-tetramethyl-13,18-divinyl-7H,8H-porphyrin-7-yl)propanoate;

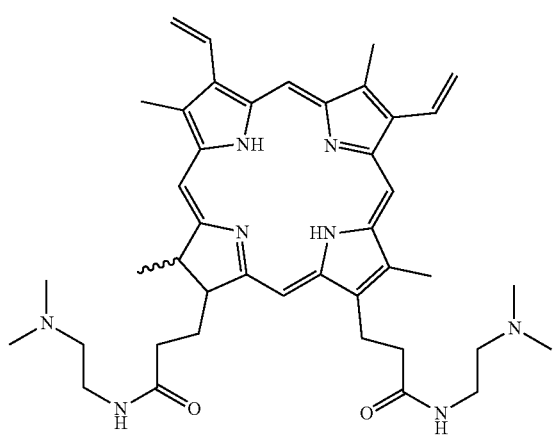

3,3'-(2,8,12,17-tetramethyl-13,18-divinyl-7H,8H-porphyrin-3,7-diyl)bis(N-(2-(dimethylamino)ethyl)propanamide);

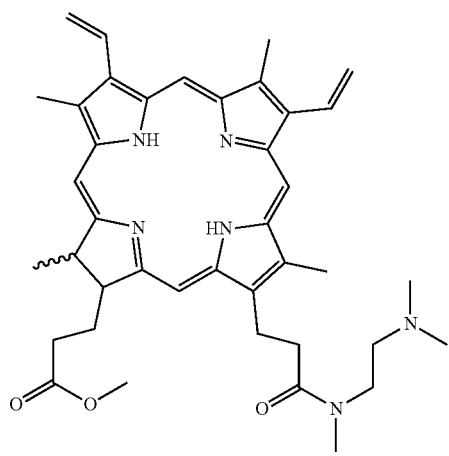 [SMILES: C=CC1=C(C)c2cc3[nH]c(cc4nc(cc5[nH]c(cc1n2)c(C)c5CCC(=O)N(C)CCN(C)C)C(CCC(=O)OC)C4C)c(C)c3C=C]

methyl 3-(3-(3-((2-(dimethylamino)ethyl)(methyl)amino)-3-oxopropyl)-2,8,12,17-tetramethyl-13,18-divinyl-7H,8H-porphyrin-7-yl)propanoate; and

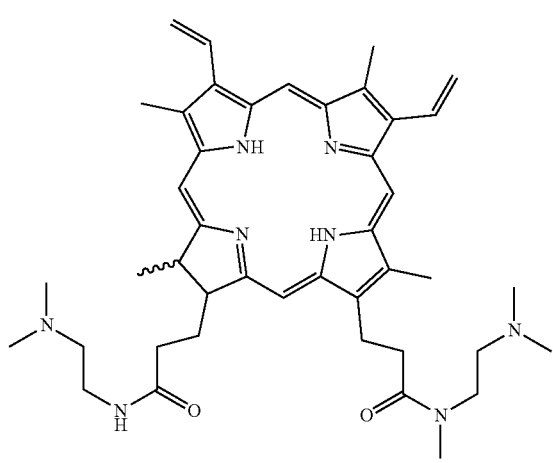

N-(2-(dimethylamino)ethyl)-3-(7-(3((2-(dimethylamino)ethyl)amino)-3-oxopropyl)-2,8,12,17-tetramethyl-13,18-divinyl-7H,8H-porphyrin-3-yl)-N-methylpropanamide.

5. The pharmaceutical composition of claim 4, wherein the verteporfin derivative compound is present in a therapeutically effective amount.

6. The pharmaceutical composition of claim 4, further comprising at least a second verteporfin derivative compound individually selected from:

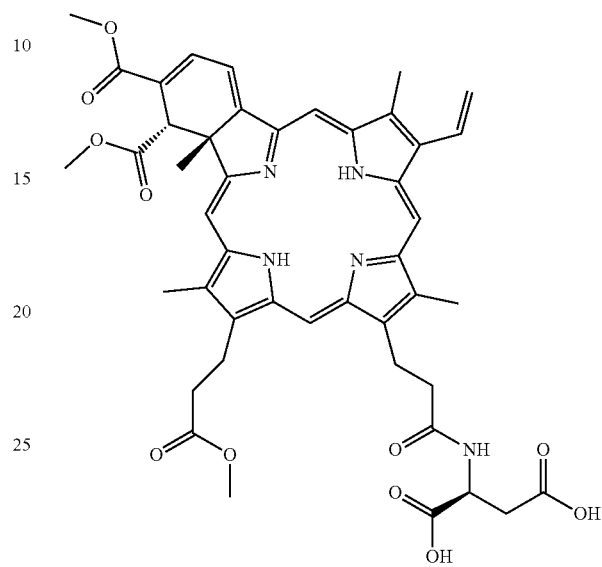

(2S)-2-[3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]butanedioic acid;

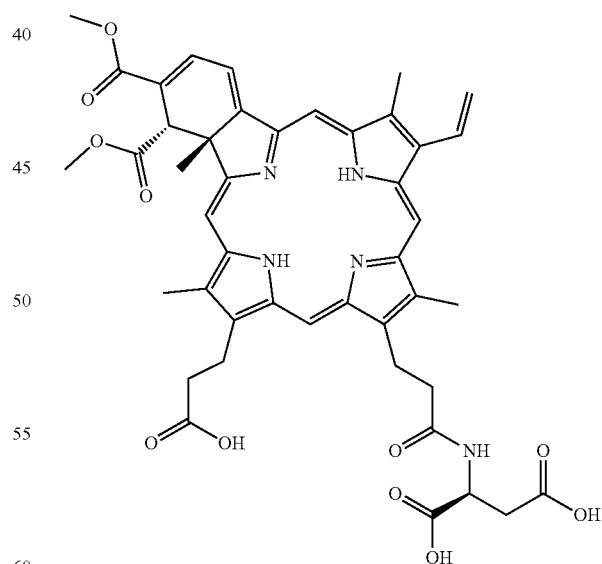

(2S)-2-[3-[(23S,24R)-14-ethenyl-5-(2-carboxyethyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]butanedioic acid;

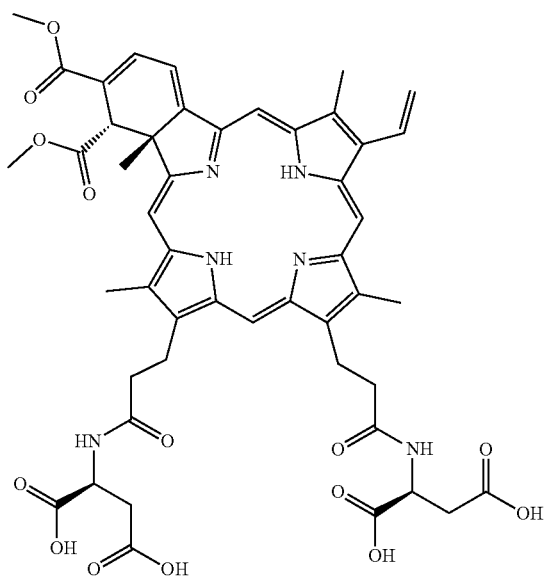 [SMILES: C=Cc1c(C)c2cc3nc(cc4[nH]c(cc5nc(cc1[nH]2)C(C)=C5CCC(=O)N[C@@H](CC(=O)O)C(=O)O)c(CCC(=O)N[C@@H](CC(=O)O)C(=O)O)c4C)[C@@]1(C)C3=CC=C(C(=O)OC)[C@H]1C(=O)OC]

(2S)-2-[3-[(23S,24R)-14-ethenyl-5-[3-[[(1S)-1,2-dicarboxyethyl]amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]butanedioic acid;

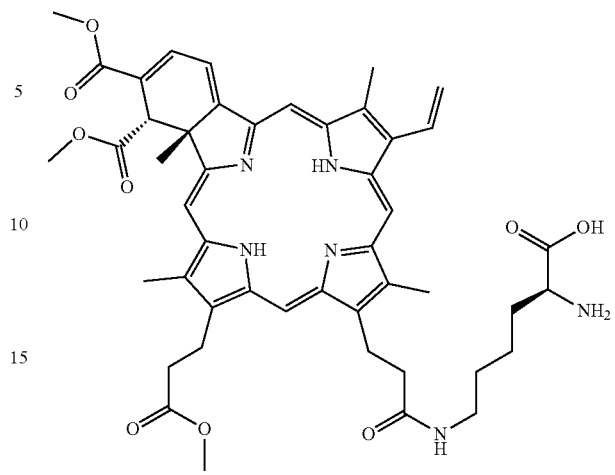

(2S)-2-amino-6-[3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]hexanoic acid;

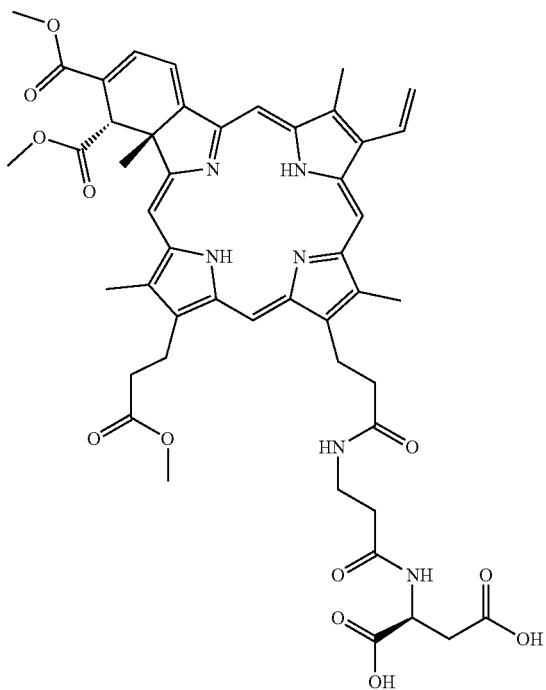 [SMILES: C=Cc1c(C)c2cc3nc(cc4[nH]c(cc5nc(cc1[nH]2)C(C)=C5CCC(=O)NCCC(=O)N[C@@H](CC(=O)O)C(=O)O)c(CCC(=O)OC)c4C)[C@@]1(C)C3=CC=C(C(=O)OC)[C@H]1C(=O)OC]

(2S)-2-[3-[3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]propanoylamino]butanedioic acid;

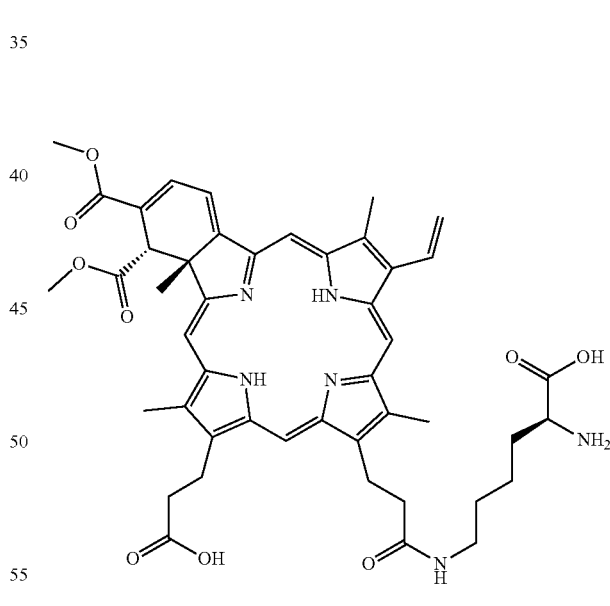

(2S)-2-amino-6-[3-[(23S,24R)-14-ethenyl-5-(2-carboxyethyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]hexanoic acid;

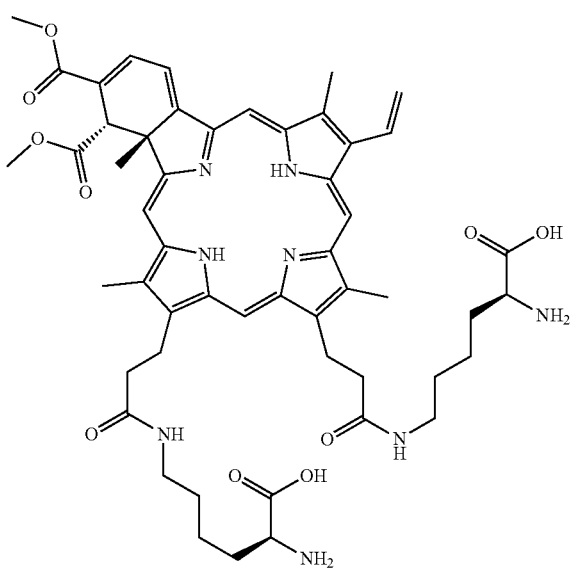 [SMILES: C=Cc1c(C)c2cc3nc(cc4[nH]c(cc5nc(cc1[nH]2)C(C)=C5CCC(=O)NCCCC[C@H](N)C(=O)O)c(CCC(=O)NCCCC[C@H](N)C(=O)O)c4C)[C@@]1(C)C3=CC=C(C(=O)OC)[C@H]1C(=O)OC]

(2S)-2-amino-6-[3-[(23S,24R)-14-ethenyl-5-[3-[[(5S)-5-amino-5-carboxy-pentyl]amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]hexanoic acid;

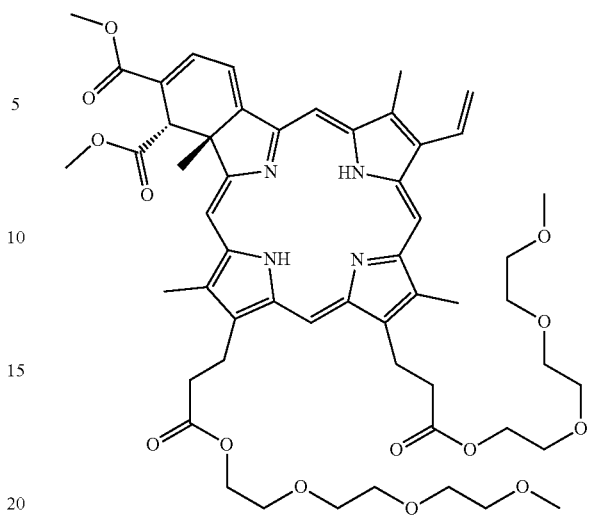

2-[2-(2-methoxyethoxy)ethoxy]ethyl 3-[(23S,24R)-14-ethenyl-5-[3-[2-[2-(2-methoxyethoxy)ethoxy]ethoxy]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoate;

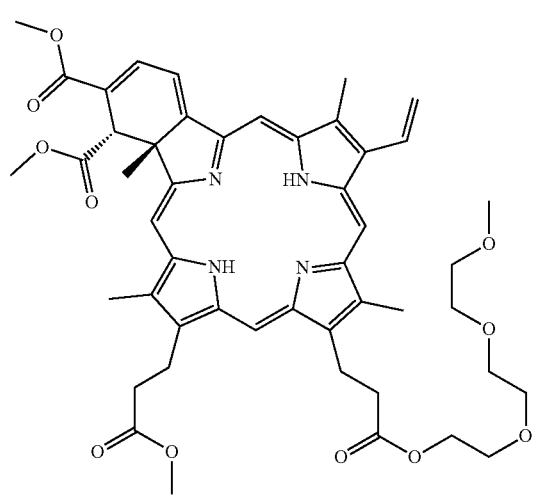 [SMILES: C=Cc1c(C)c2cc3nc(cc4[nH]c(cc5nc(cc1[nH]2)C(C)=C5CCC(=O)OCCOCCOCCOC)c(CCC(=O)OC)c4C)[C@@]1(C)C3=CC=C(C(=O)OC)[C@H]1C(=O)OC]

Methyl 3-[(23S,24R)-14-ethenyl-9-[3-[2-[2-(2-methoxyethoxy)ethoxy]ethoxy]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoate;

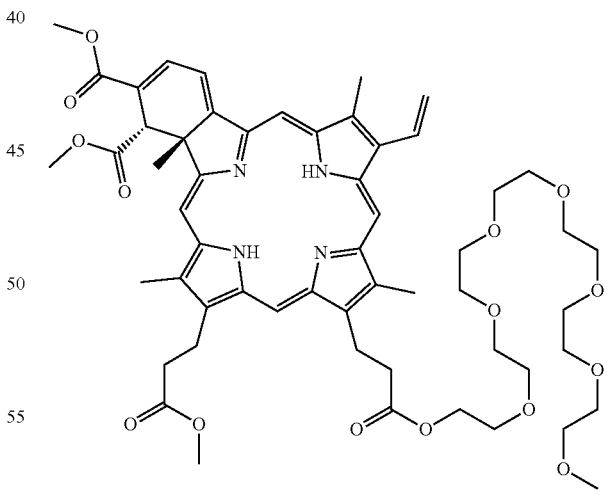

Methyl 3-[(23S,24R)-14-ethenyl-9-[3-[2-[2-[2-[2-[2-[2-(2-methoxyethoxy)ethoxy]ethoxy]ethoxy]ethoxy]ethoxy]ethoxy]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoate;

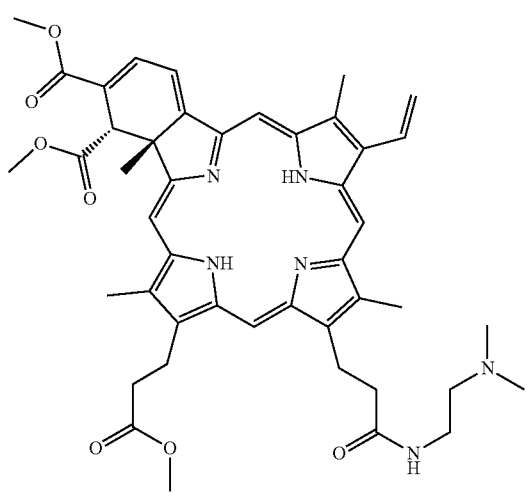

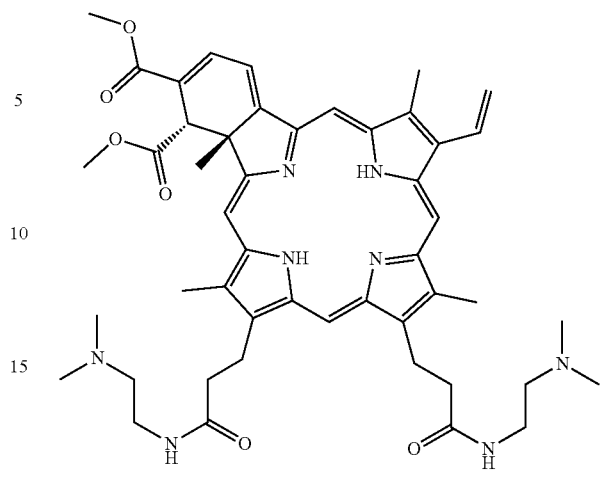

Methyl 3-[(23S,24R)-14-ethenyl-9-[3-[2-(dimethylamino)ethylamino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoate;

N-[2-(dimethylamino)ethyl]-3-[(23S,24R)-14-ethenyl-5-[3-[2-(dimethylamino)ethylamino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanamide;

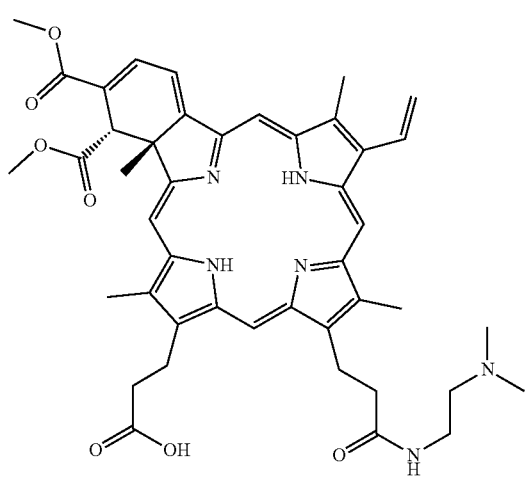

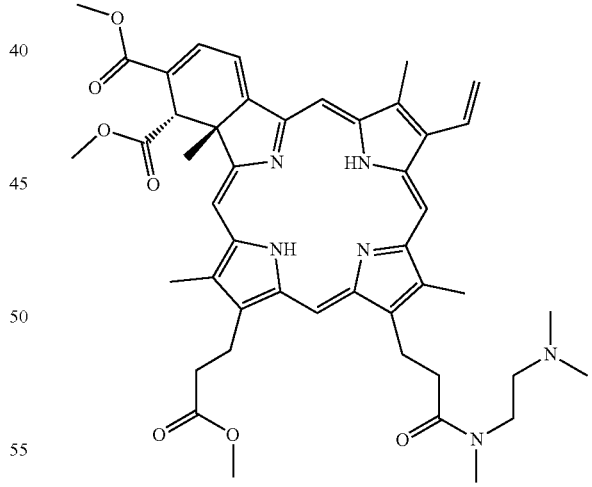

3-[(23S,24R)-14-ethenyl-9-[3-[2-(dimethylamino)ethylamino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoic acid;

Methyl 3-[(23S,24R)-14-ethenyl-9-[3-[2-(dimethylamino)ethyl-methyl-amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoate;

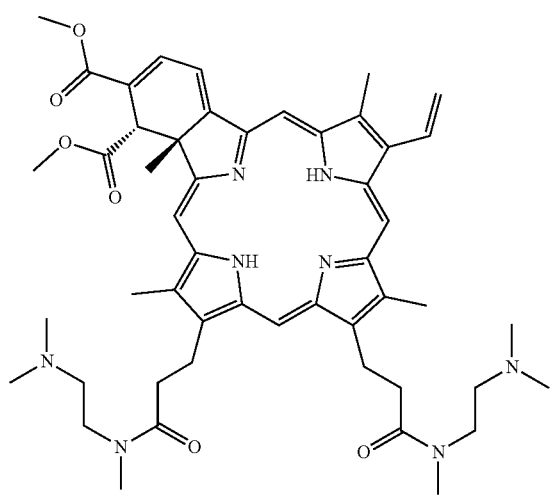

N-[2-(dimethylamino)ethyl]-3-[(23 S,24R)-14-ethenyl-5-[3-[2-(dimethylamino)ethyl-methyl-amino]-3-oxo-propy 1]-22,23-bis(methoxycarbonyl)-4,10,15,24-tetramethyl-25,26,27,28-tetraazahexacyclo[16.6.1.13, 6.18,11.113,16.019,24] octacosa-1,3,5,7,9, 11(27),12, 14,16,18(25),19,21-dodecaen-9-yl]-N-methyl-propanamide;

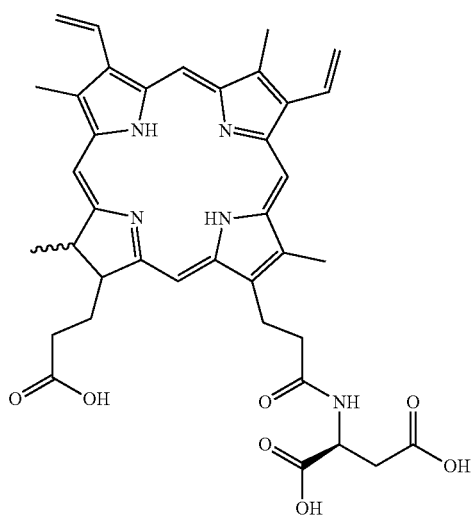

(3-(7-(2-carboxyethyl)-2,8,12,17-tetramethyl-13,18-divinyl-7H,8H-porphyrin-3-yl)propanoyl)-L-aspartic acid;

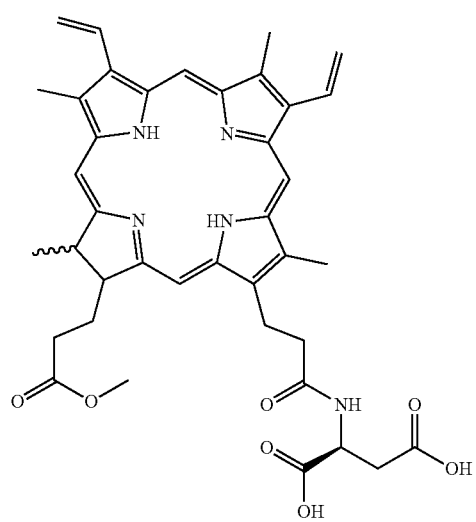 [SMILES: C=CC1=C(C)c2cc3[nH]c(cc4nc(cc5[nH]c(cc1n2)c(C)c5CCC(=O)N[C@@H](CC(=O)O)C(=O)O)C(CCC(=O)OC)C4C)c(C)c3C=C]

(3-(7-(3-methoxy-3-oxopropyl)-2,8,12,17-tetramethyl-13,18-divinyl-7H,8H-porphyrin-3-yl)propanoyl)-L-aspartic acid;

(3-(7-(5,6-dicarboxy-3-oxohexyl)-2,8,12,17-tetramethyl-13,18-divinyl-7H,8H-porphyrin-3-yl)propanoyl)-L-aspartic acid;

91

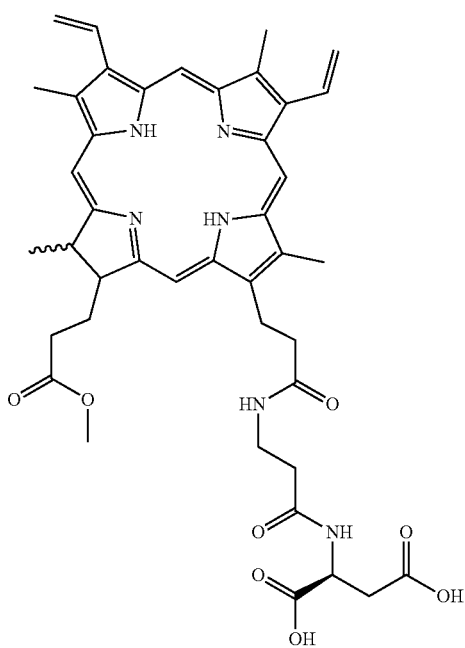 [SMILES: C=CC1=C(C)c2cc3[nH]c(cc4nc(cc5[nH]c(cc1n2)c(C)c5CCC(=O)NCCC(=O)N[C@@H](CC(=O)O)C(=O)O)C(CCC(=O)OC)C4C)c(C)c3C=C]

(3-(3-(7-(3-methoxy-3-oxopropyl)-2,8,12,17-tetramethyl-13,18-divinyl-7H, 8H-porphyrin-3-yl)propanamido)propanoyl)-L-aspartic acid;

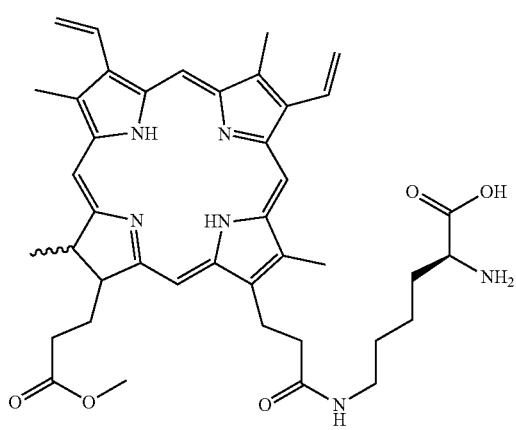 [SMILES: C=CC1=C(C)c2cc3[nH]c(cc4nc(cc5[nH]c(cc1n2)c(C)c5CCC(=O)NCCCC[C@H](N)C(=O)O)C(CCC(=O)OC)C4C)c(C)c3C=C]

N[6]-(3-(7-(3-methoxy-3-oxopropyl)-2,8,12,17-tetramethyl-13,18-divinyl-7H,8H-porphyrin-3-yl)propanoyl)-L-lysine;

92

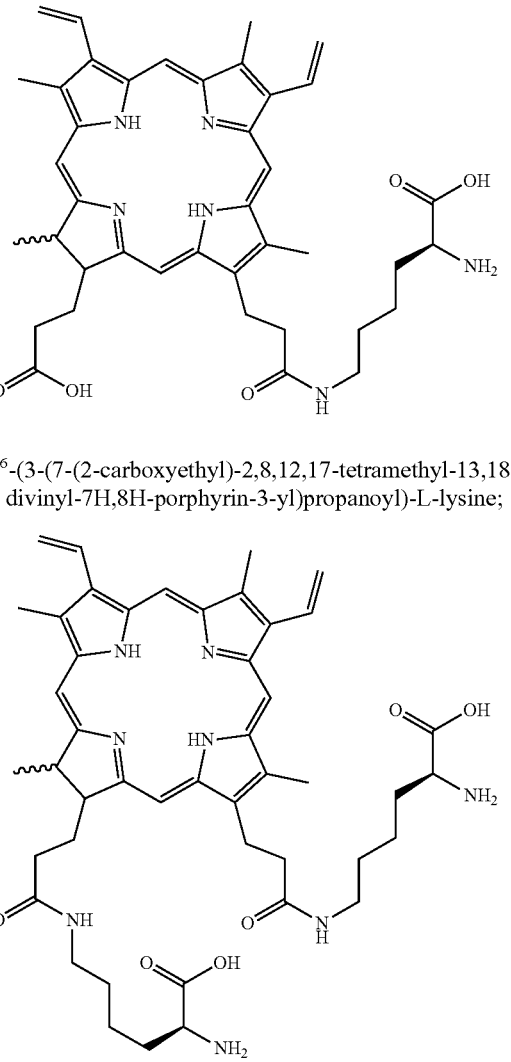

N[6]-(3-(7-(2-carboxyethyl)-2,8,12,17-tetramethyl-13,18-divinyl-7H,8H-porphyrin-3-yl)propanoyl)-L-lysine;

(2S,2'S)-6,6'-(((3,3'-(2,8,12,17-tetramethyl-13,18-divinyl-7H,8H-porphyrin-3,7-diyl)bis(propanoyl))bis(azanediyl))bis(2-aminohexanoic acid);

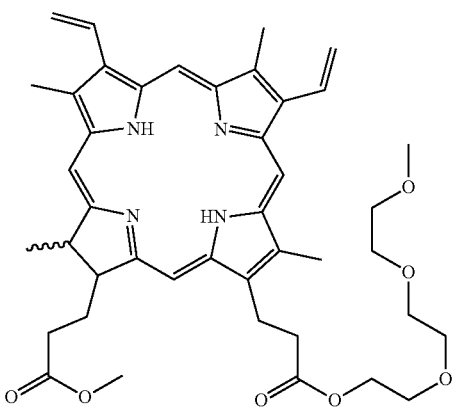 [SMILES: C=CC1=C(C)c2cc3[nH]c(cc4nc(cc5[nH]c(cc1n2)c(C)c5CCC(=O)OCCOCCOCCOC)C(CCC(=O)OC)C4C)c(C)c3C=C]

2-(2-(2-methoxyethoxy)ethoxy)ethyl 3-(7-(3-methoxy-3-oxopropyl)-2,8,12,17-tetramethyl-13,18-divinyl-7H, 8H-porphyrin-3-yl)propanoate;

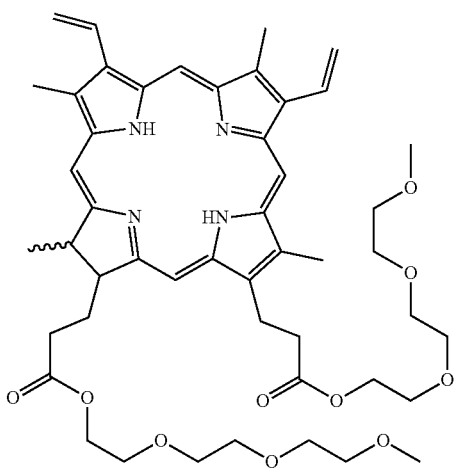 [SMILES: C=CC1=C(C)c2cc3[nH]c(cc4nc(cc5[nH]c(cc1n2)c(C)c5CCC(=O)OCCOCCOCCOC)C(CCC(=O)OCCOCCOCCOC)C4C)c(C)c3C=C]

bis(2-(2-(2-methoxyethoxy)ethoxy)ethyl) 3,3'-(2,8,12,17-tetramethyl-13,18-divinyl-7H,8H-porphyrin-3,7-diyl)dipropionate;

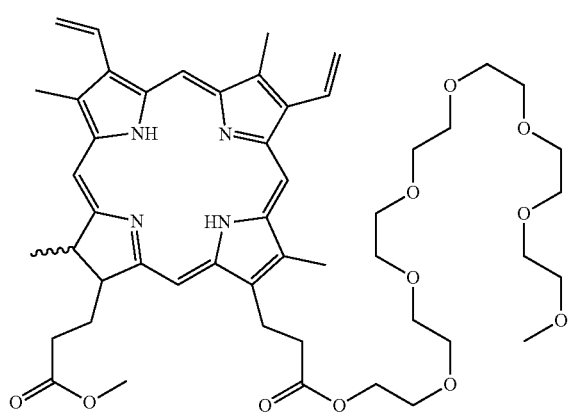 [SMILES: C=CC1=C(C)c2cc3[nH]c(cc4nc(cc5[nH]c(cc1n2)c(C)c5CCC(=O)OCCOCCOCCOCCOCCOCCOCCOC)C(CCC(=O)OC)C4C)c(C)c3C=C]

2,5,8,11,14,17,20-heptaoxadocosan-22-yl 3-(7-(3-methoxy-3-oxopropyl)-2,8,12,17-tetramethyl-13,18-divinyl-7H,8H-porphyrin-3-yl)propanoate;

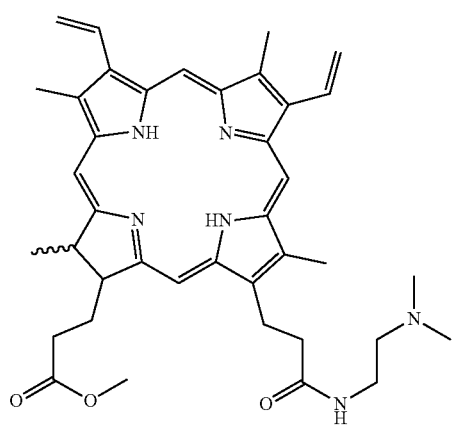 [SMILES: C=CC1=C(C)c2cc3[nH]c(cc4nc(cc5[nH]c(cc1n2)c(C)c5CCC(=O)NCCN(C)C)C(CCC(=O)OC)C4C)c(C)c3C=C]

methyl 3-(3-(3-((2-(dimethylamino)ethyl)amino)-3-oxopropyl)-2,8,12,17-tetramethyl-13,18-divinyl-7H,8H-porphyrin-7-yl)propanoate;

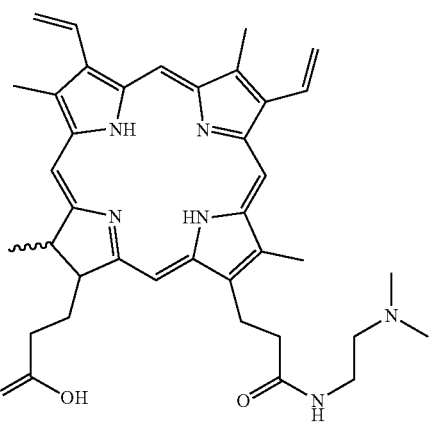

3-(3-(3-((2-(dimethylamino)ethyl)amino)-3-oxopropyl)-2,8,12,17-tetramethyl-13,18-divinyl-7H,8H-porphyrin-7-yl)propanoic acid;

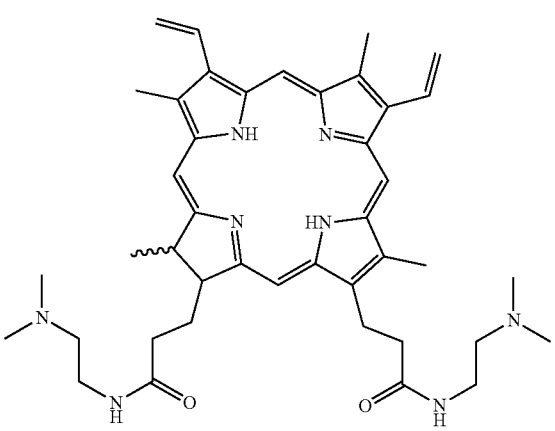

3,3'-(2,8,12,17-tetramethyl-13,18-divinyl-7H,8H-porphyrin-3,7-diyl)bis(N-(2-(dimethylamino)ethyl)propanamide);

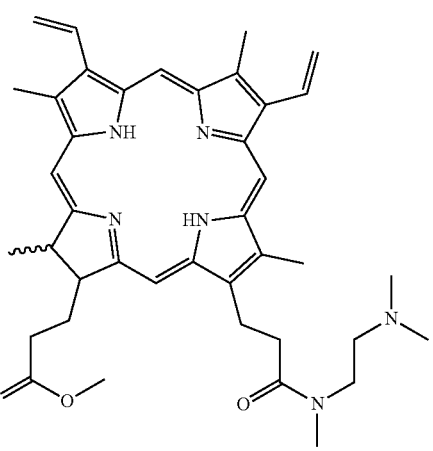

methyl 3-(3-(3-((2-(dimethylamino)ethyl)(methyl)amino)-3-oxopropyl)-2,8,12,17-tetramethyl-13,18-divinyl-7H,8H-porphyrin-7-yl)propanoate; and

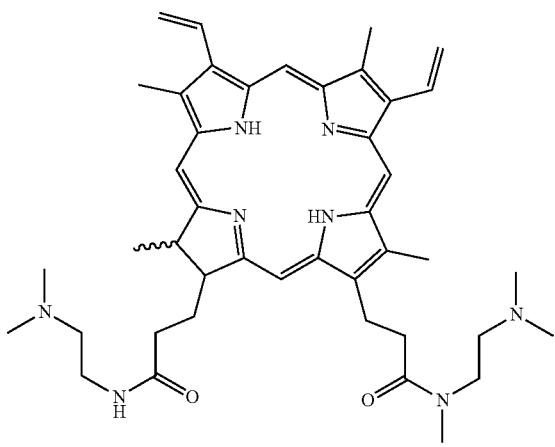

N-(2-(dimethylamino)ethyl)-3-(7-(3-((2-(dimethylamino)ethyl)amino)-3-oxopropyl)-2,8,12,17-tetramethyl-13,18-divinyl-7H,8H-porphyrin-3-yl)-N-methylpropanamide.

7. A method of therapeutically treating a subject diagnosed with a cancer, the cancer comprising a cell expressing YAP1, the method comprising:

administering, to the subject, a pharmaceutical composition comprising a verteporfin derivative compound selected from the group consisting of:

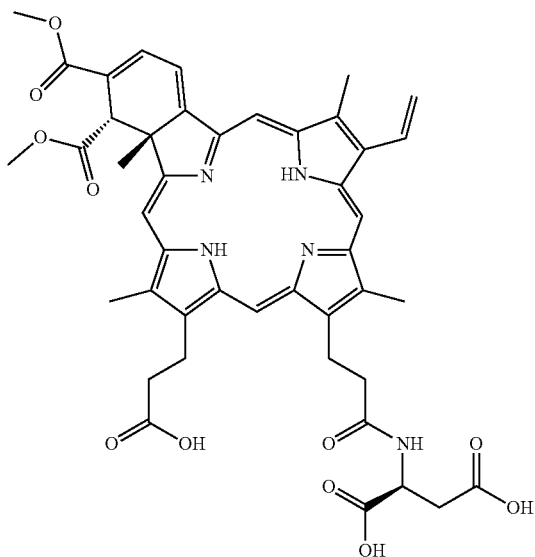

(2S)-2-[3-[(23S,24R)-14-ethenyl-5-(2-carboxyethyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]butanedioic acid;

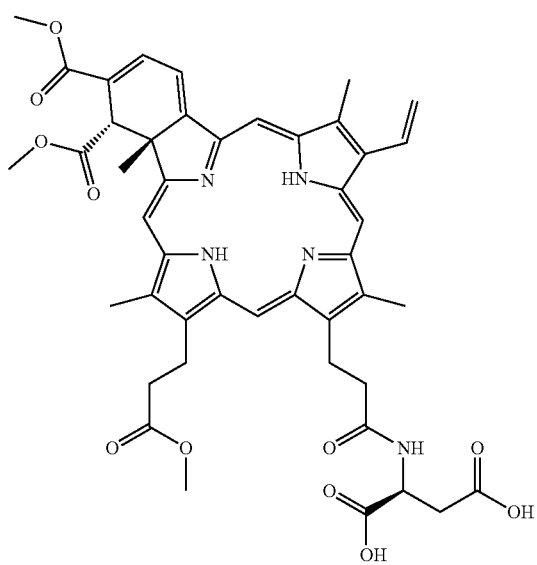 [SMILES: C=Cc1c(C)c2cc3nc(cc4[nH]c(cc5nc(cc1[nH]2)C(C)=C5CCC(=O)N[C@@H](CC(=O)O)C(=O)O)c(CCC(=O)OC)c4C)[C@@]1(C)C3=CC=C(C(=O)OC)[C@H]1C(=O)OC]

(2S)-2-[3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]butanedioic acid;

(2S)-2-[3-[(23S,24R)-14-ethenyl-5-[3-[[(1S)-1,2-dicarboxyethyl]amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]butanedioic acid;

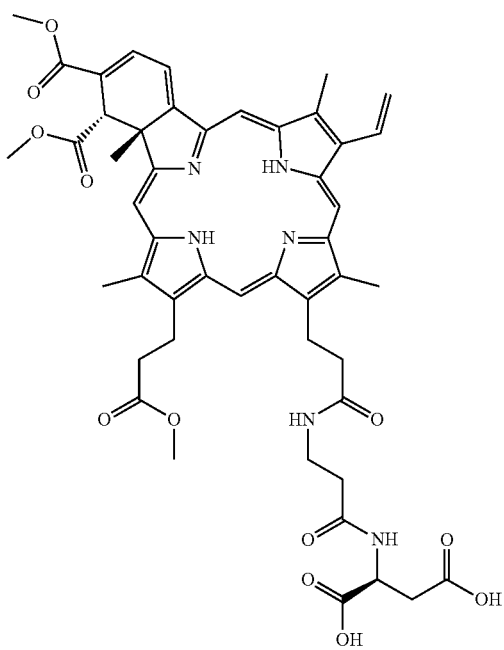 [SMILES: C=Cc1c(C)c2cc3nc(cc4[nH]c(cc5nc(cc1[nH]2)C(C)=C5CCC(=O)NCCC(=O)N[C@@H](CC(=O)O)C(=O)O)c(CCC(=O)OC)c4C)[C@@]1(C)C3=CC=C(C(=O)OC)[C@H]1C(=O)OC]

(2S)-2-[3-[3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]propanoylamino]butanedioic acid;

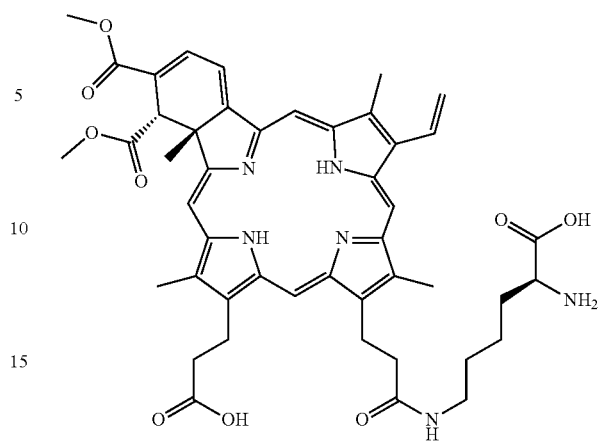

(2S)-2-amino-6-[3-[(23S,24R)-14-ethenyl-5-(2-carboxy-ethyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]hexanoic acid;

(2S)-2-amino-6-[3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]hexanoic acid;

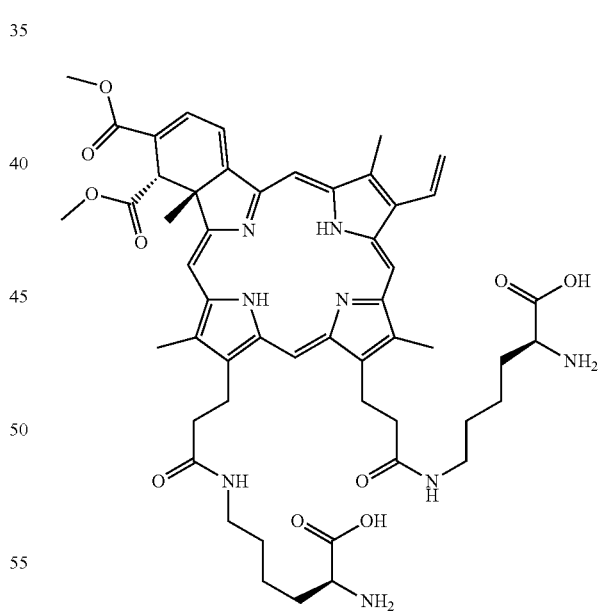

(2S)-2-amino-6-[3-[(23S,24R)-14-ethenyl-5-[3-[[(5S)-5-amino-5-carboxy-pentyl]amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]hexanoic acid;

99

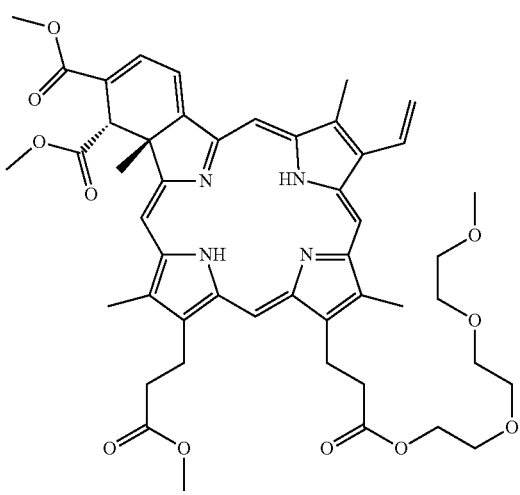 [SMILES: C=Cc1c(C)c2cc3nc(cc4[nH]c(cc5nc(cc1[nH]2)C(C)=C5CCC(=O)OCCOCCOCCOC)c(CCC(=O)OC)c4C)[C@@]1(C)C3=CC=C(C(=O)OC)[C@H]1C(=O)OC]

Methyl 3-[(23S,24R)-14-ethenyl-9-[3-[2-[2-(2-methoxyethoxy)ethoxy]ethoxy]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoate;

100

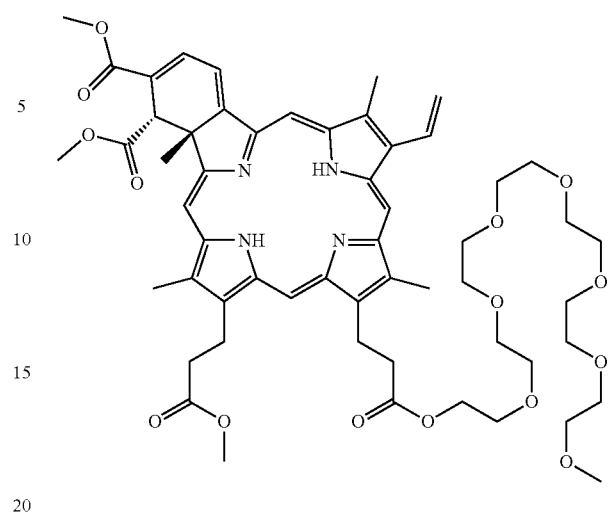

Methyl 3-[(23S,24R)-14-ethenyl-9-[3-[2-[2-[2-[2-[2-[2-(2-methoxyethoxy)ethoxy]ethoxy]ethoxy]ethoxy]ethoxy]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoate;

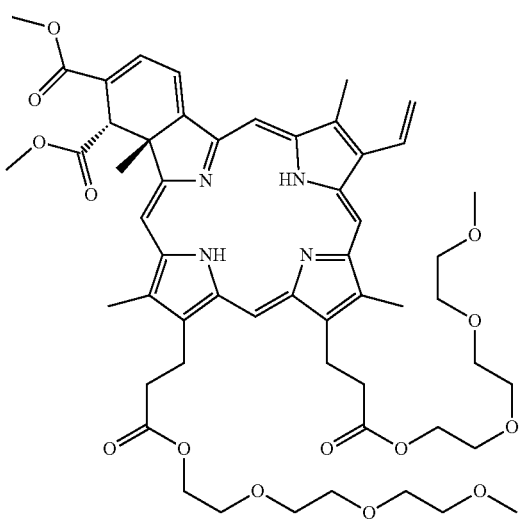

2-[2-(2-methoxyethoxy)ethoxy]ethyl 3-[(23S,24R)-14-ethenyl-5-[3-[2-[2-(2-methoxyethoxy)ethoxy]ethoxy]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoate;

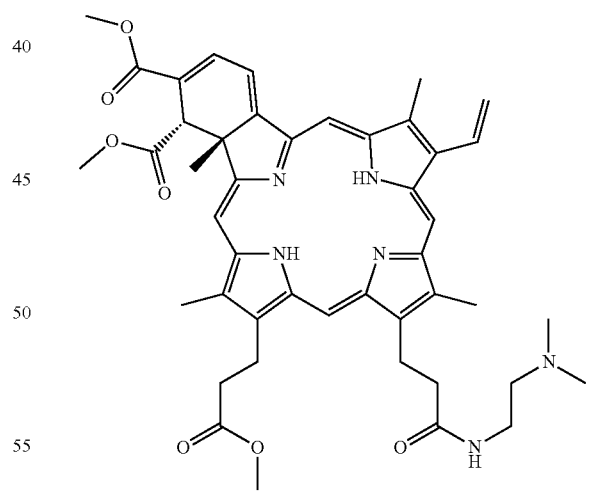

Methyl 3-[(23S,24R)-14-ethenyl-9-[3-[2-(dimethylamino)ethylamino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoate;

101

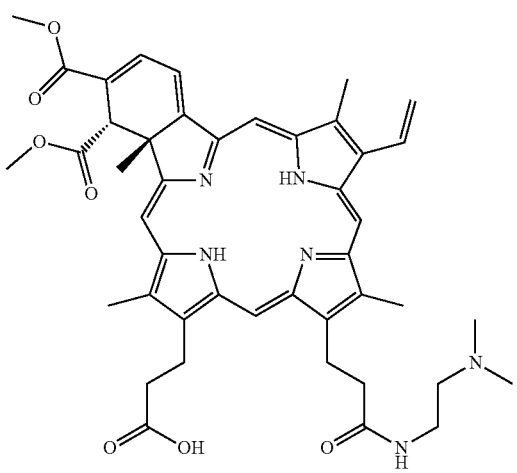

3-[(23S,24R)-14-ethenyl-9-[3-[2-(dimethylamino)ethyl-amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoic acid;

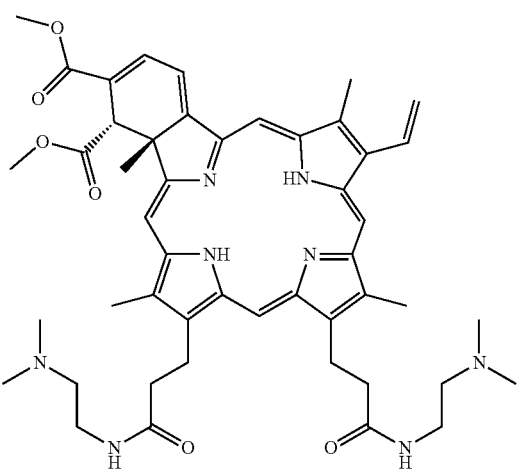

N-[2-(dimethylamino)ethyl]-3-[(23S,24R)-14-ethenyl-5-[3-[2-(dimethylamino)ethylamino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanamide;

102

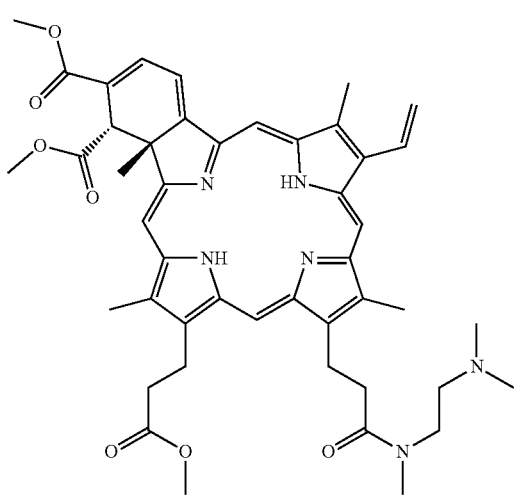

Methyl 3-[(23S,24R)-14-ethenyl-94342-(dimethylamino)ethyl-methyl-amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoate;

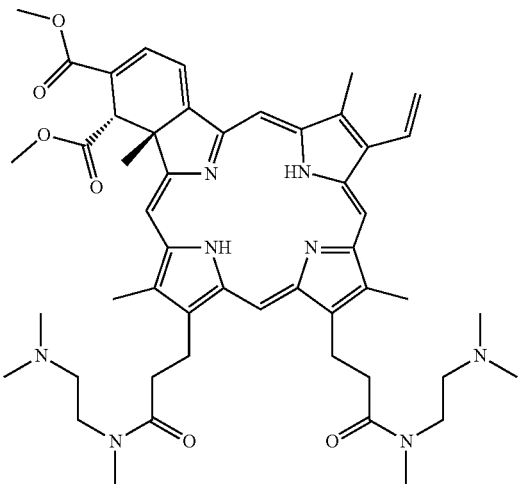

N-[2-(dimethylamino)ethyl]-3-[(23 S,24R)-14-ethenyl-5-[3 42-(dimethylamino)ethyl-methyl-amino]-3-oxo-propy 1]-22,23-bis(methoxycarbonyl)-4,10,15,24-tetramethyl-25,26,27,28-tetraazahexacyclo[16.6.1.13,6.18,11.113,16.019,24] octacosa-1,3,5,7,9, 11(27),12,14,16,18(25),19,21-dodecaen-9-yl]-N-methyl-propanamide;

103
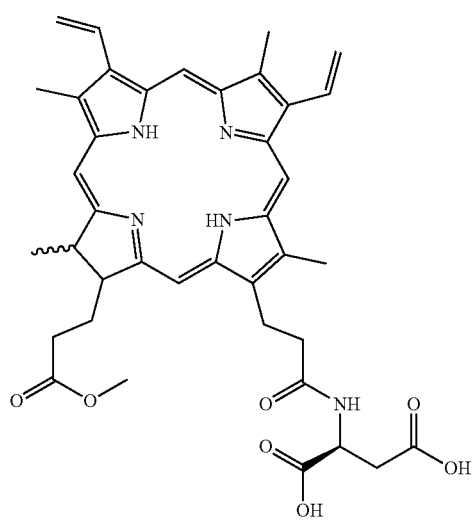 [SMILES: C=CC1=C(C)c2cc3[nH]c(cc4nc(cc5[nH]c(cc1n2)c(C)c5CCC(=O)N[C@@H](CC(=O)O)C(=O)O)C(CCC(=O)OC)C4C)c(C)c3C=C]
(3-(7-(3-methoxy-3-oxopropyl)-2,8,12,17-tetramethyl-13,18-divinyl-7H,8H-porphyrin-3-yl)propanoyl)-L-aspartic acid;
104
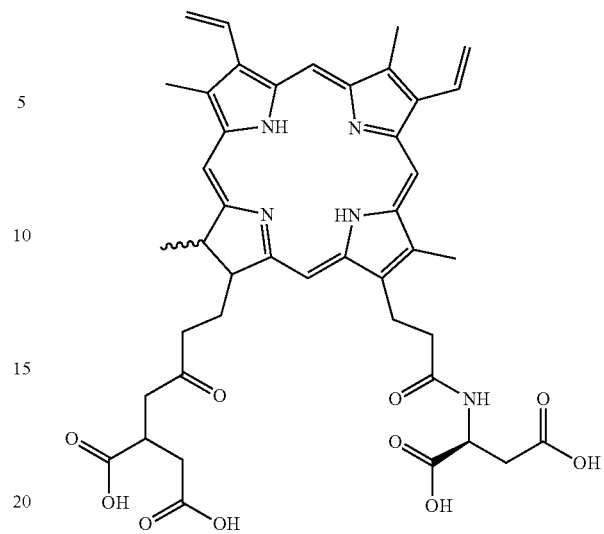
(3-(7-(5,6-dicarboxy-3-oxohexyl)-2,8,12,17-tetramethyl-13,18-divinyl-7H,8H-porphyrin-3-yl)propanoyl)-L-aspartic acid
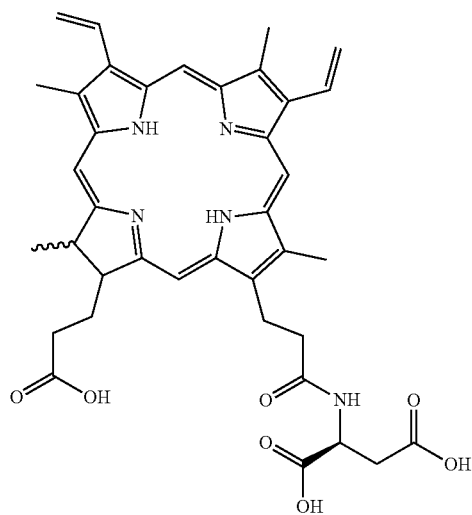 [SMILES: C=CC1=C(C)c2cc3[nH]c(cc4nc(cc5[nH]c(cc1n2)c(C)c5CCC(=O)N[C@@H](CC(=O)O)C(=O)O)C(CCC(=O)O)C4C)c(C)c3C=C]
(3-(7-(2-carboxyethyl)-2,8,12,17-tetramethyl-13,18-divinyl-7H,8H-porphyrin-3-yl)propanoyl)-L-aspartic acid;
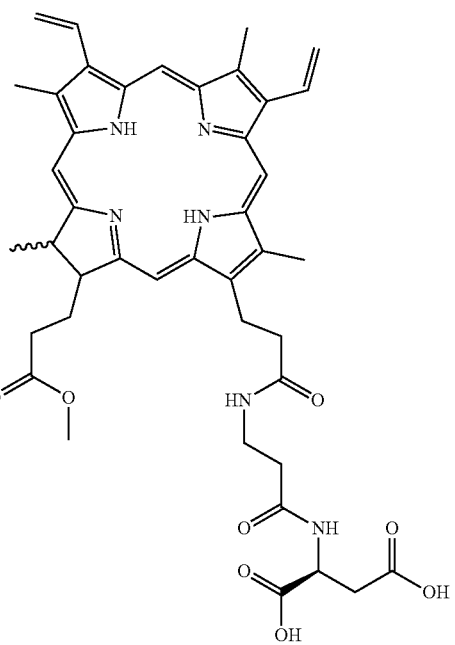
(3-(3-(7-(3-methoxy-3-oxopropyl)-2,8,12,17-tetramethyl-13,18-divinyl-7H,8H-porphyrin-3-yl)propanamido)propanoyl)-L-aspartic acid;

105

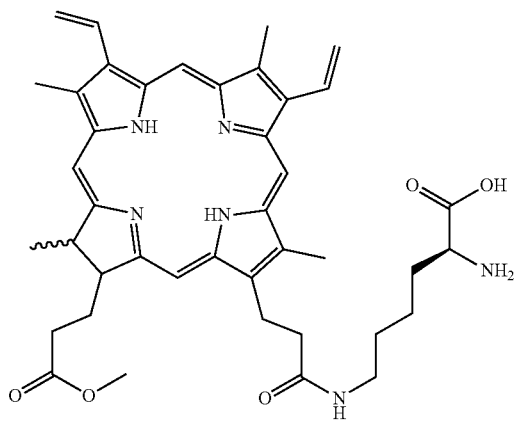 [SMILES: C=CC1=C(C)c2cc3[nH]c(cc4nc(cc5[nH]c(cc1n2)c(C)c5CCC(=O)NCCCC[C@H](N)C(=O)O)C(CCC(=O)OC)C4C)c(C)c3C=C]

N⁶-(3-(7-(3-methoxy-3-oxopropyl)-2,8,12,17-tetramethyl-13,18-divinyl-7H,8H-porphyrin-3-yl)propanoyl)-L-lysine;

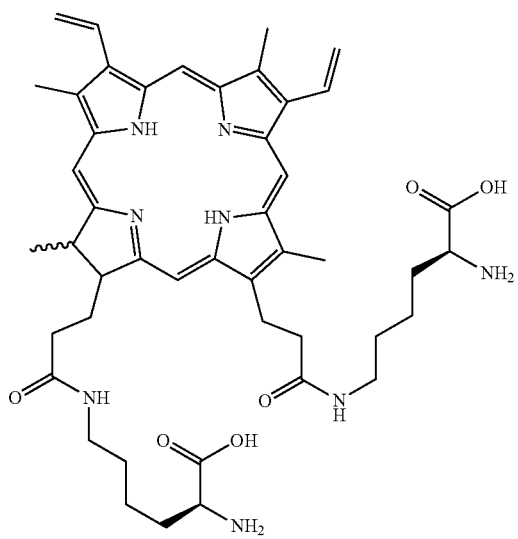 [SMILES: C=CC1=C(C)c2cc3[nH]c(cc4nc(cc5[nH]c(cc1n2)c(C)c5CCC(=O)NCCCC[C@H](N)C(=O)O)C(CCC(=O)NCCCC[C@H](N)C(=O)O)C4C)c(C)c3C=C]

(2S,2'S)-6,6'-(((3,3'-(2,8,12,17-tetramethyl-13,18-divinyl-7H,8H-porphyrin-3,7-diyl)bis(propanoyl))bis(azanediyl))bis(2-aminohexanoic acid);

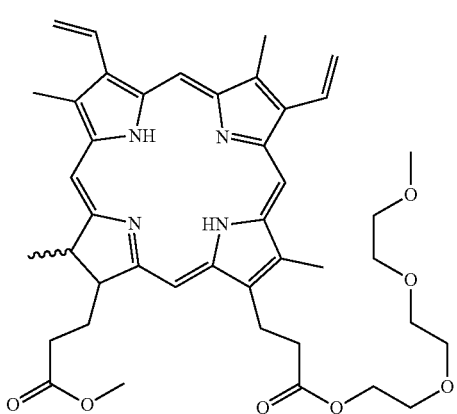 [SMILES: C=CC1=C(C)c2cc3[nH]c(cc4nc(cc5[nH]c(cc1n2)c(C)c5CCC(=O)OCCOCCOCCOC)C(CCC(=O)OC)C4C)c(C)c3C=C]

2-(2-(2-methoxyethoxy)ethoxy)ethyl 3-(7-(3-methoxy-3-oxopropyl)-2,8,12,17-tetramethyl-13,18-divinyl-7H,8H-porphyrin-3-yl)propanoate;

106

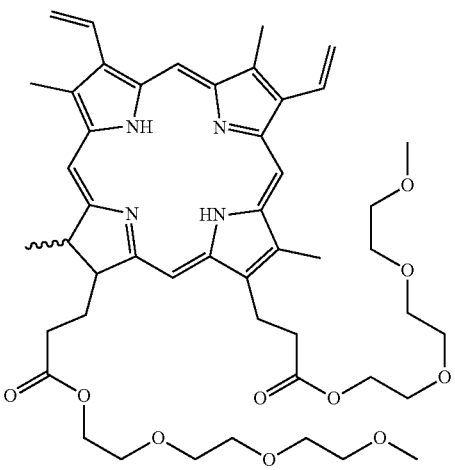 [SMILES: C=CC1=C(C)c2cc3[nH]c(cc4nc(cc5[nH]c(cc1n2)c(C)c5CCC(=O)OCCOCCOCCOC)C(CCC(=O)OCCOCCOCCOC)C4C)c(C)c3C=C]

bis(2-(2-(2-methoxyethoxy)ethoxy)ethyl) 3,3'-(2,8,12,17-tetramethyl-13,18-divinyl-7H,8H-porphyrin-3,7-diyl)dipropionate;

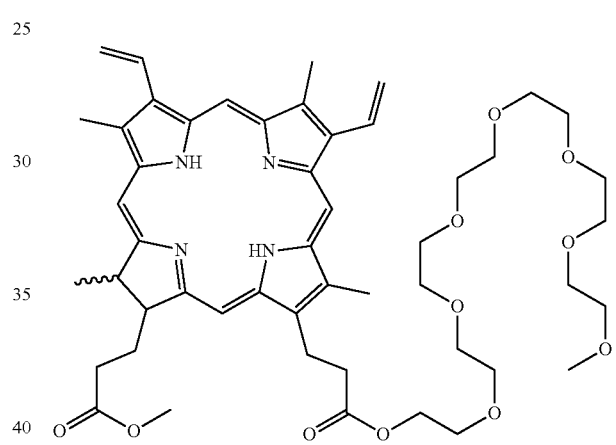

2,5,8,11,14,17,20-heptaoxadocosan-22-yl 3-(7-(3-methoxy-3-oxopropyl)-2,8,12,17-tetramethyl-13,18-divinyl-7H,8H-porphyrin-3-yl)propanoate;

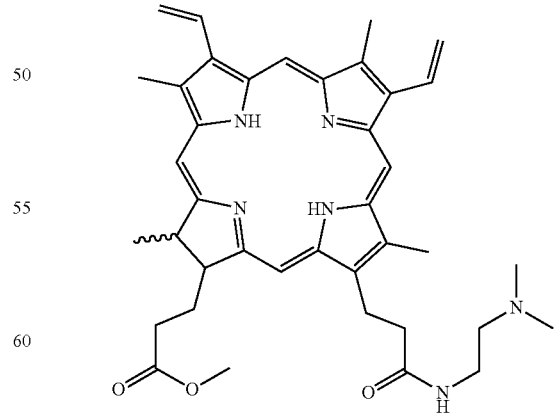

methyl 3-(3-(3-(((2-(dimethylamino)ethyl)amino)-3-oxopropyl)-2,8,12,17-tetramethyl-13,18-divinyl-7H,8H-porphyrin-7-yl)propanoate;

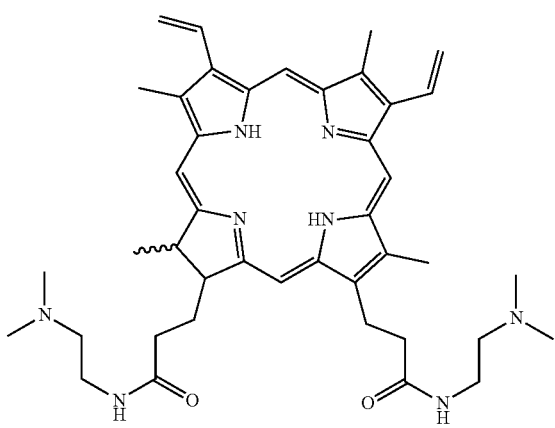

3,3'-(2,8,12,17-tetramethyl-13,18-divinyl-7H,8H-porphyrin-3,7-diyl)bis(N-(2-(dimethylamino)ethyl)propanamide);

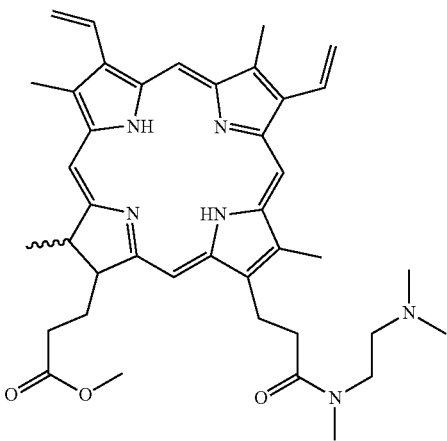 [SMILES: C=CC1=C(C)c2cc3[nH]c(cc4nc(cc5[nH]c(cc1n2)c(C)c5CCC(=O)N(C)CCN(C)C)C(CCC(=O)OC)C4C)c(C)c3C=C]

methyl 3-(3-(3-((2-(dimethylamino)ethyl)(methyl)amino)-3-oxopropyl)-2,8,12,17-tetramethyl-13,18-divinyl-7H,8H-porphyrin-7-yl)propanoate; and

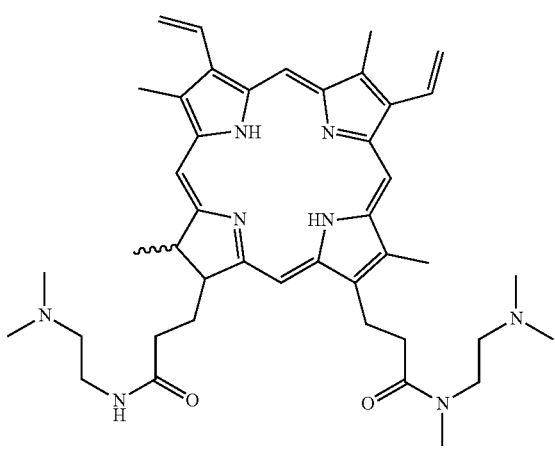

N-(2-(dimethylamino)ethyl)-3-(7-(3-((2-(dimethylamino)ethyl)amino)-3-oxopropyl)-2,8,12,17-tetramethyl-13,18-divinyl-7H,8H-porphyrin-3-yl)-N-methylpropanamide.

8. The method of claim 7, wherein the cancer comprises a brain tumor.

9. The method of claim 7, wherein the cancer comprises a pediatric tumor.

10. The method of claim 7, wherein the cancer comprises a medulloblastoma.

11. The method of claim 10, wherein the medulloblastoma is an SHH group medulloblastoma.

12. The method of claim 7, wherein the cancer further comprises a cell expressing Sonic Hedgehog (SHH).

13. The method of claim 7, wherein the cancer has been previously treated with at least one of a MAP Kinase inhibitor, a SMO inhibitor, and a SHH pathway inhibitor.

14. The method of claim 7, wherein the cancer comprises a cancer cell resistant to at least one of a MAP Kinase inhibitor, a SMO inhibitor, and a SHH pathway inhibitor.

15. The method of claim 7, wherein the administering step is performed via intravenous administration, intraperitoneal injection, or oral administration of the pharmaceutical composition.

16. The method of claim 7, wherein the administering step is performed via injection of the pharmaceutical composition into a spinal canal or ventricular compartment of the subject.

17. The method of claim 7, further comprising the step of treating the subject with at least one of surgery, radiation therapy, targeted therapy, and a chemotherapeutic agent.

18. The method of claim 7, further comprising administering, to the subject, a pharmaceutical composition comprising at least one of a SMO inhibitor, a MAP Kinase inhibitor, and a SHH pathway inhibitor.

19. The method of claim 7, wherein the subject is a human.

20. The method of claim 7, wherein the pharmaceutical composition comprises at least a second verteporfin derivative compound individually selected from the group.

21. A pharmaceutical composition comprising a verteporfin derivative compound and a pharmaceutically acceptable excipient, the verteporfin derivative compound including at least one of:

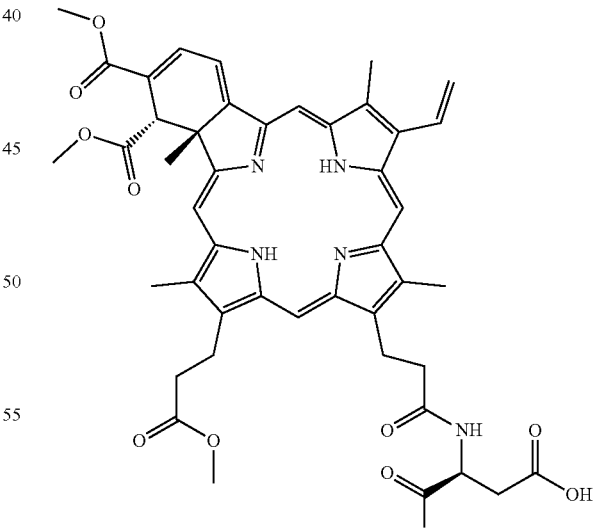

(2S)-2-[3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]butanedioic acid;

109

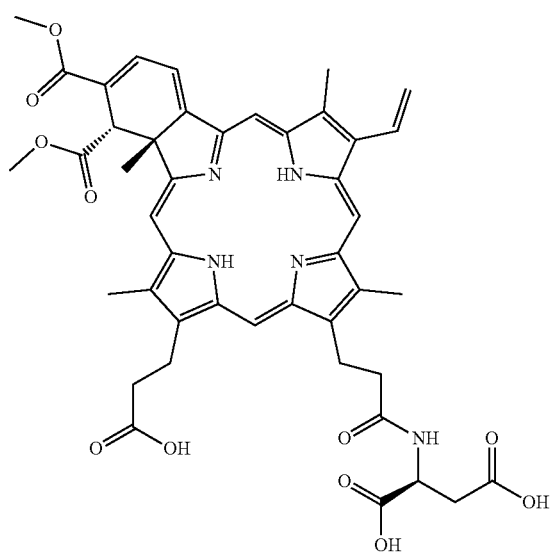 [SMILES: C=Cc1c(C)c2cc3nc(cc4[nH]c(cc5nc(cc1[nH]2)C(C)=C5CCC(=O)N[C@@H](CC(=O)O)C(=O)O)c(CCC(=O)O)c4C)[C@@]1(C)C3=CC=C(C(=O)OC)[C@H]1C(=O)OC]

(2S)-2-[3-[(23S,24R)-14-ethenyl-5-(2-carboxyethyl)-22,23-bis(methoxycarbonyl)-4,10,15,24-tetramethyl-25,26,27,28-tetraazahexacyclo[16.6.1.1³,⁶.1⁸,¹¹.1¹³,¹⁶.0¹⁹,²⁴]octacosa-1,3,5,7,9,11(27),12,14,16,18(25),19,21-dodecaen-9-yl]propanoylamino]butanedioic acid;

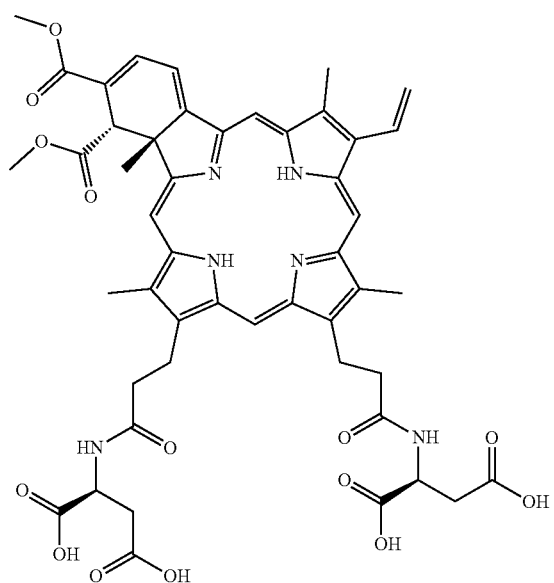 [SMILES: C=Cc1c(C)c2cc3nc(cc4[nH]c(cc5nc(cc1[nH]2)C(C)=C5CCC(=O)N[C@@H](CC(=O)O)C(=O)O)c(CCC(=O)N[C@@H](CC(=O)O)C(=O)O)c4C)[C@@]1(C)C3=CC=C(C(=O)OC)[C@H]1C(=O)OC]

(2S)-2-[3-[(23S,24R)-14-ethenyl-5-[3-[[(1S)-1,2-dicarboxyethyl]amino]-3-oxo-propyl]-22,23-bis(methoxycarbonyl)-4,10,15,24-tetramethyl-25,26,27,28-tetraazahexacyclo[16.6.1.1³,⁶.1⁸,¹¹.1¹³,¹⁶.0¹⁹,²⁴]octacosa-1,3,5,7,9,11(27),12,14,16,18(25),19,21-dodecaen-9-yl]propanoylamino]butanedioic acid;

110

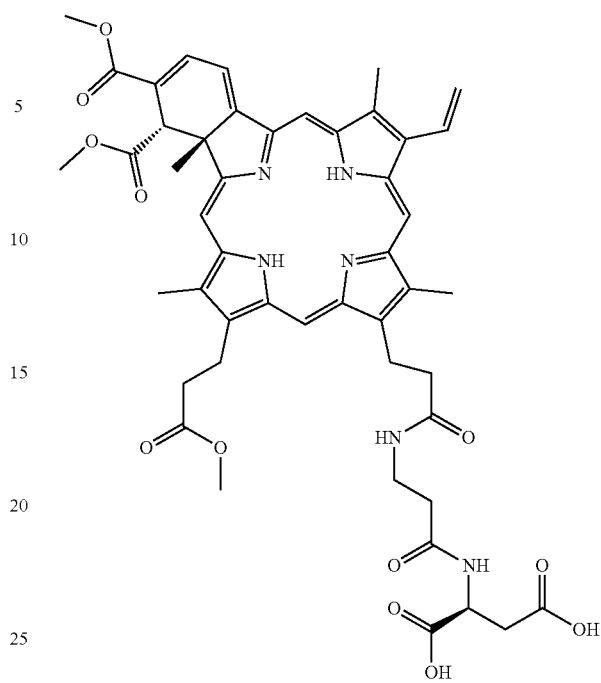

(2S)-2-[3-[3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.1³,⁶.1⁸,¹¹.1¹³,¹⁶.0¹⁹,²⁴]octacosa-1,3,5,7,9,11(27),12,14,16,18(25),19,21-dodecaen-9-yl]propanoylamino]propanoylamino]butanedioic acid;

(2S)-2-amino-6-[3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.1³,⁶.1⁸,¹¹.1¹³,¹⁶.0¹⁹,²⁴]octacosa-1,3,5,7,9,11(27),12,14,16,18(25),19,21-dodecaen-9-yl]propanoylamino]hexanoic acid;

111

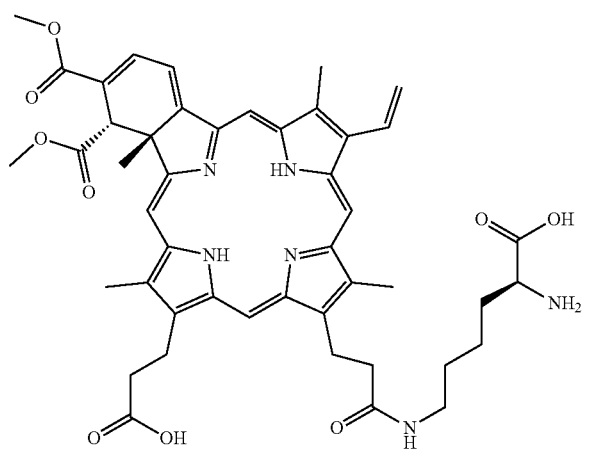 [SMILES: C=Cc1c(C)c2cc3nc(cc4[nH]c(cc5nc(cc1[nH]2)C(C)=C5CCC(=O)NCCCC[C@H](N)C(=O)O)c(CCC(=O)O)c4C)[C@@]1(C)C3=CC=C(C(=O)OC)[C@H]1C(=O)OC]

(2S)-2-amino-6-[3-[(23S,24R)-14-ethenyl-5-(2-carboxy-ethyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]hexanoic acid;

112

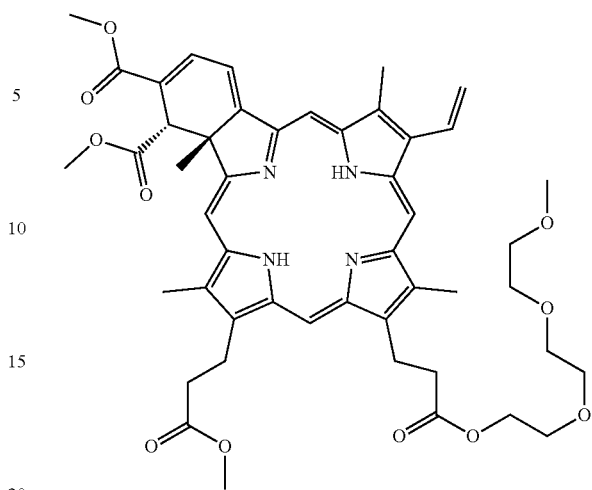

Methyl 3-[(23S,24R)-14-ethenyl-9-[3-[2-[2-(2-methoxyethoxy)ethoxy]ethoxy]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoate;

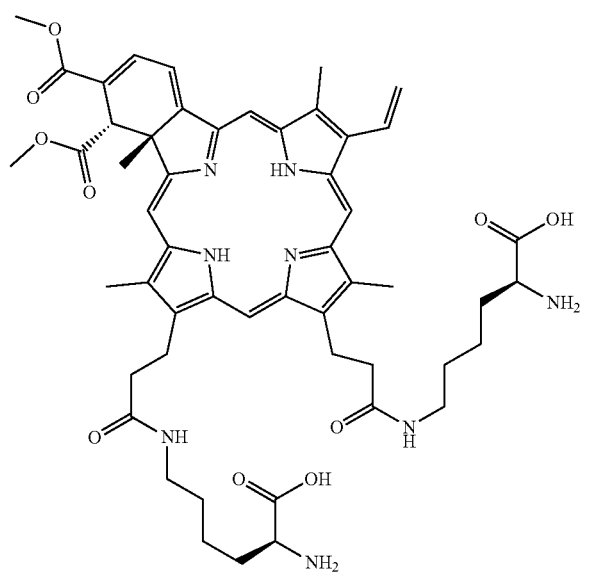 [SMILES: C=Cc1c(C)c2cc3nc(cc4[nH]c(cc5nc(cc1[nH]2)C(C)=C5CCC(=O)NCCCC[C@H](N)C(=O)O)c(CCC(=O)NCCCC[C@H](N)C(=O)O)c4C)[C@@]1(C)C3=CC=C(C(=O)OC)[C@H]1C(=O)OC]

(2S)-2-amino-6-[3-[(23S,24R)-14-ethenyl-5-[3-[[(5S)-5-amino-5-carboxy-pentyl]amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoylamino]hexanoic acid;

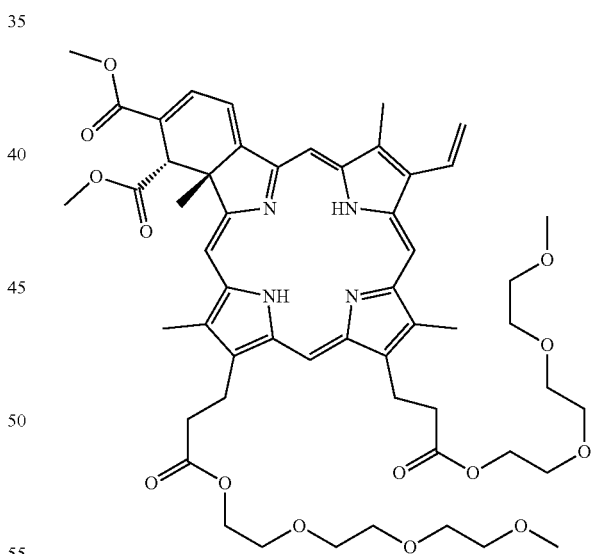

2-[2-(2-methoxyethoxy)ethoxy]ethyl 3-[(23S,24R)-14-ethenyl-5-[3-[2-[2-(2-methoxyethoxy)ethoxy]ethoxy]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoate;

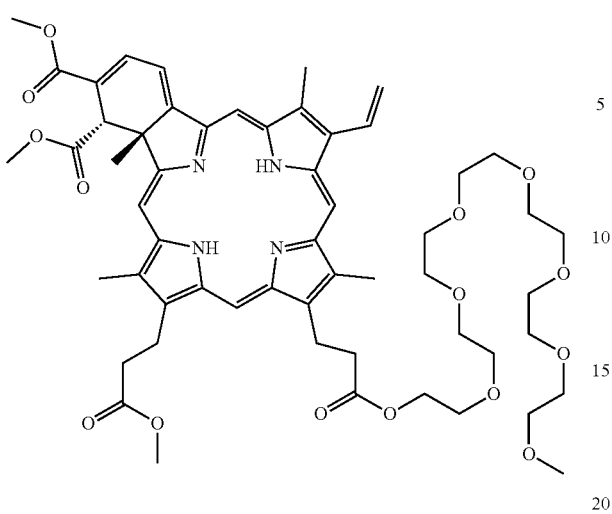

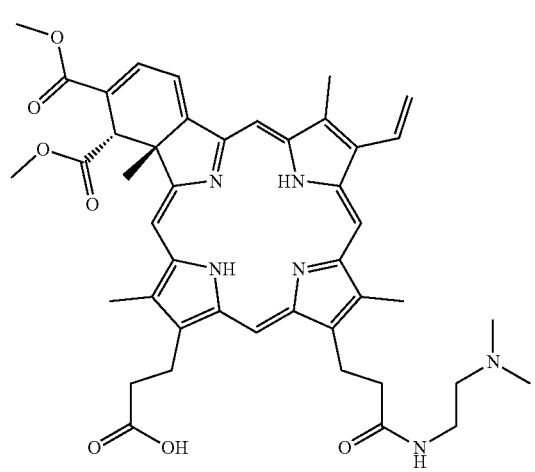

Methyl 3-[(23S,24R)-14-ethenyl-9-[3-[2-[2-[2-[2-[2-[2-(2-methoxyethoxy)ethoxy]ethoxy]ethoxy]ethoxy]ethoxy]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoate;

3-[(23S,24R)-14-ethenyl-9-[3-[2-(dimethylamino)ethylamino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoic acid;

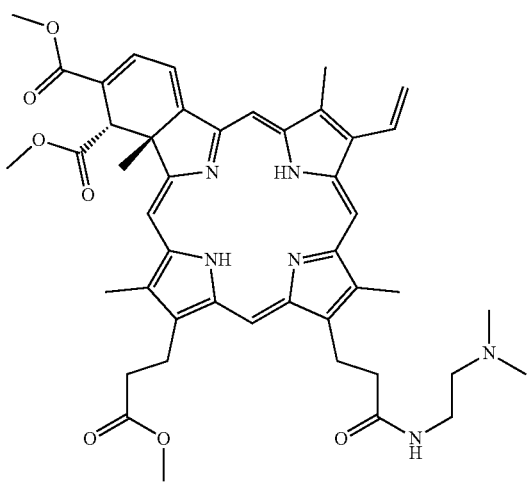

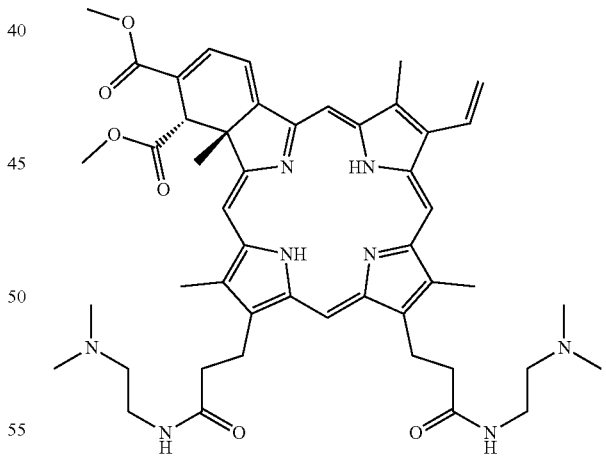

Methyl 3-[(23S,24R)-14-ethenyl-9-[3-[2-(dimethylamino)ethylamino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoate;

N-[2-(dimethylamino)ethyl]-3-[(23S,24R)-14-ethenyl-5-[3[2-(dimethylamino)ethylamino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanamide;

115

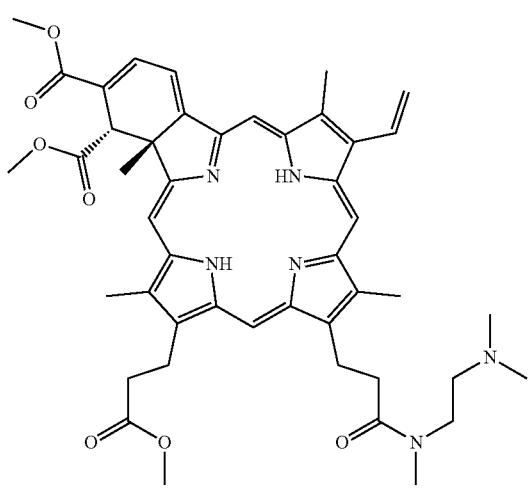

Methyl 3-[(23S,24R)-14-ethenyl-9-[3-[2-(dimethyl-amino)ethyl-methyl-amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-5-yl]propanoate; and

116

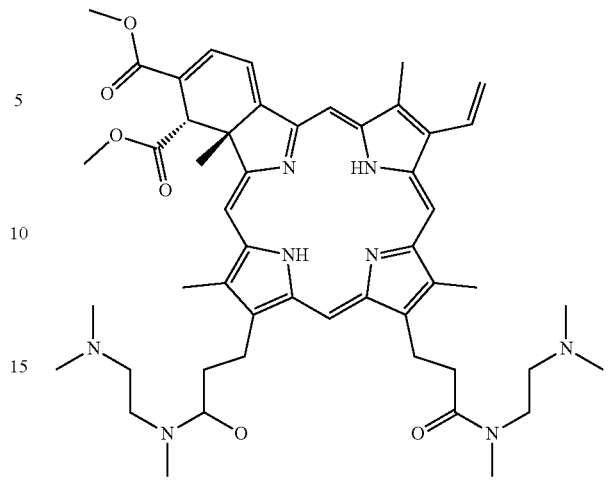

N-[2-(dimethylamino)ethyl]-3-[(23S,24R)-14-ethenyl-5-[3-[2-(dimethylamino)ethyl-methyl-amino]-3-oxo-propyl]-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]-N-methyl-propanamide.

22. The pharmaceutical composition of claim 21, wherein the verteporfin derivative compound is present in a therapeutically effective amount.

* * * * *